US010117974B2

(12) United States Patent
Li et al.

(10) Patent No.: US 10,117,974 B2
(45) Date of Patent: Nov. 6, 2018

(54) NON-FOULING, ANTI-MICROBIAL, ANTI-THROMBOGENIC GRAFT-FROM COMPOSITIONS

(71) Applicant: ARROW INTERNATIONAL, INC., Wayne, PA (US)

(72) Inventors: Jun Li, Brookline, MA (US); Zheng Zhang, Cambridge, MA (US); Chad C. Huval, Somerville, MA (US); Michael A. Bouchard, Wyomissing, PA (US); Christopher R. Loose, Cambridge, MA (US); Arthur J. Coury, Boston, MA (US)

(73) Assignee: ARROW INTERNATIONAL, INC., Wayne, PA (US)

( * ) Notice: Subject to any disclaimer, the term of this patent is extended or adjusted under 35 U.S.C. 154(b) by 663 days.

(21) Appl. No.: 14/531,383

(22) Filed: Nov. 3, 2014

(65) Prior Publication Data

US 2015/0045515 A1 Feb. 12, 2015

Related U.S. Application Data

(63) Continuation of application No. 13/156,677, filed on Jun. 9, 2011, now Pat. No. 9,096,703.

(60) Provisional application No. 61/353,059, filed on Jun. 9, 2010.

(51) Int. Cl.
| A61L 33/00 | (2006.01) |
| A61L 29/06 | (2006.01) |
| A61L 29/08 | (2006.01) |
| C08F 291/00 | (2006.01) |
| C08J 7/16 | (2006.01) |
| C08J 7/18 | (2006.01) |
| C08F 255/02 | (2006.01) |
| C08G 18/83 | (2006.01) |
| C08G 64/42 | (2006.01) |
| C08G 77/38 | (2006.01) |

(52) U.S. Cl.
CPC ........... A61L 33/0088 (2013.01); A61L 29/06 (2013.01); A61L 29/085 (2013.01); C08F 255/02 (2013.01); C08F 291/00 (2013.01); C08G 18/836 (2013.01); C08G 64/42 (2013.01); C08G 77/38 (2013.01); C08J 7/16 (2013.01); C08J 7/18 (2013.01); C08J 2323/12 (2013.01); C08J 2369/00 (2013.01); C08J 2383/04 (2013.01); C08J 2433/14 (2013.01); Y10T 428/24355 (2015.01); Y10T 428/265 (2015.01); Y10T 442/30 (2015.04); Y10T 442/60 (2015.04)

(58) Field of Classification Search
None
See application file for complete search history.

(56) References Cited

U.S. PATENT DOCUMENTS

| 4,098,728 | A | 7/1978 | Rosenblatt |
| 4,211,227 | A | 7/1980 | Anderson et al. |
| 4,636,208 | A | 1/1987 | Rath |
| 4,877,864 | A | 10/1989 | Wang et al. |
| 5,013,649 | A | 5/1991 | Wang et al. |
| 5,180,375 | A | 1/1993 | Feibus |
| 5,453,467 | A | 9/1995 | Bamford et al. |
| 5,661,007 | A | 8/1997 | Wozney et al. |
| 5,688,678 | A | 11/1997 | Hewick et al. |
| 5,739,236 | A | 4/1998 | Bowers et al. |
| 5,844,016 | A | 12/1998 | Sawhney et al. |
| 5,866,113 | A | 2/1999 | Hendriks et al. |
| 5,997,895 | A | 12/1999 | Narotam et al. |
| 6,054,504 | A | 4/2000 | Dalla Riva Toma |
| 6,150,459 | A | 11/2000 | Mayes et al. |
| 6,177,406 | B1 | 1/2001 | Wang et al. |
| 6,251,964 | B1 | 6/2001 | Porssa et al. |
| 6,358,557 | B1 | 3/2002 | Wang et al. |
| 6,395,800 | B1 | 5/2002 | Jones et al. |
| 6,432,919 | B1 | 8/2002 | Wang et al. |
| 6,489,382 | B1 | 12/2002 | Giesecke et al. |
| 6,534,268 | B1 | 3/2003 | Kawai et al. |
| 6,558,734 | B2 | 5/2003 | Koulik et al. |
| 6,559,242 | B1 | 5/2003 | Ball et al. |
| 6,589,665 | B2 | 7/2003 | Chabrecek et al. |
| 6,711,879 | B2 | 3/2004 | Korteweg et al. |

(Continued)

FOREIGN PATENT DOCUMENTS

| JP | H08-131536 A | 5/1996 |
| JP | H11-47263 A | 2/1999 |

(Continued)

OTHER PUBLICATIONS

Cheng, N. et al., Thickness-Dependent Properties of Polyzwitterionic Brushes, Macromolecules, 2008, 41(17), 6317-6321.

Weinstock, B.A., et al., Rapid, Nondestructive Estimation of Surface Polymer Layer Thickness Using Attenuated Total Relection Fourier Transform Infrared (ATR FT-IR) Spectroscopy and Synthetic Spectra Derived from Optical Principles, Applied Spectroscopy.

Feng et al., Atom-Transfer Radical Grafting Polymerization of 2-Methacryloyloxyethyl Phosphorycholine from Silicon Wafer Surfaces. Journal of Polymer Science Part A: Polymer Chemistry 2004, 42, 2931-2942.

(Continued)

Primary Examiner — Michael P Rodriguez
(74) Attorney, Agent, or Firm — Baker Hostetler LLP

(57) ABSTRACT

A method for preparing and resulting articles of manufacture comprising a substrate having a surface, a bulk beneath the surface, and a grafted polymer layer on the substrate surface, the substrate surface and the grafted polymer layer, in combination, constituting a modified surface having a fibrinogen adsorption of less than about 125 ng/cm$^2$ in a fibrinogen binding assay in which the modified surface is incubated for 60 minutes at 37° C. in 70 μg/mL fibrinogen derived from human plasma containing 1.4 μg/mL I-125 radiolabeled fibrinogen.

14 Claims, No Drawings

(56) References Cited

U.S. PATENT DOCUMENTS

| | | | |
|---|---|---|---|
| 7,087,658 | B2 | 8/2006 | Swan et al. |
| 7,220,491 | B2 | 5/2007 | Rouns et al. |
| 7,238,364 | B2 | 7/2007 | Sawhney et al. |
| 7,238,426 | B2 | 7/2007 | Jiang et al. |
| 7,276,286 | B2 | 10/2007 | Chapman et al. |
| 7,306,625 | B1 | 12/2007 | Stratford et al. |
| 7,431,888 | B2 | 10/2008 | Frechet et al. |
| 2001/0050749 | A1 | 12/2001 | Watanabe |
| 2003/0021823 | A1 | 1/2003 | Landers et al. |
| 2003/0143335 | A1 | 7/2003 | Qiu et al. |
| 2004/0253383 | A1 | 12/2004 | Belik et al. |
| 2004/0256232 | A1 | 12/2004 | Jiang et al. |
| 2006/0057180 | A1 | 3/2006 | Chilkoti et al. |
| 2006/0217285 | A1 | 9/2006 | Destarac |
| 2007/0048249 | A1 | 3/2007 | Youngblood et al. |
| 2007/0254006 | A1 | 11/2007 | Loose et al. |
| 2008/0181861 | A1 | 7/2008 | Jiang et al. |
| 2009/0155335 | A1 | 6/2009 | O'Shaughnessey et al. |
| 2009/0162662 | A1 | 6/2009 | Chang et al. |
| 2009/0197791 | A1 | 8/2009 | Balastre et al. |
| 2010/0072642 | A1 | 3/2010 | Broad et al. |
| 2010/0099160 | A1 | 4/2010 | Jiang et al. |
| 2011/0045200 | A1* | 2/2011 | Hsueh ................. C08J 7/18 427/489 |

FOREIGN PATENT DOCUMENTS

| | | |
|---|---|---|
| JP | 2004-121618 A | 4/2004 |
| JP | 2007-152097 A | 6/2007 |
| WO | 03000433 | 1/2003 |
| WO | 2007002493 | 1/2007 |
| WO | 2007/024393 A2 | 3/2007 |
| WO | 2007024393 | 3/2007 |
| WO | 2007095393 | 8/2007 |
| WO | 2008006911 | 1/2008 |
| WO | 2008019381 | 2/2008 |
| WO | 2008083390 | 7/2008 |
| WO | 2009085096 | 7/2009 |
| WO | 2010/065960 A2 | 6/2010 |

OTHER PUBLICATIONS

Goda et al., Biomimetic phosphoryl choline polymer grafting from polydimethylsiloxane surface using photo-induced polymerization. Biomaterials 2006, 27 (30), 5151-60.

Yuan et al., Improvement of blood compatibility on cellulose membrane surface by grafting betaines. Colloids and Surfaces B: Biointerfaces 30.

Jiang et al., Blood compatibility of polyurethane surface grafted copolymerization with sulfobetaine monomer. Colloids Surf B Biointerfaces 2004, 36 (1),27-33.

Jin et al., Protein-resistant polyurethane prepared by surface-initiated atom transfer radical graft polymerization (ATRgP) of water-soluble polymers: effects of main chain and side chain lengths of grafts. Colloids Surf B Biointerfaces 2009, 70 (1),53-9.

Jin et al., Protein-resistant polyurethane via surface-initiated atom transfer radical polymerization of oligo(ethylene glycol) methacrylate. J Biomed Mater Res A 2009, 91(4), 1189-201.

Zhang et al., Chemical modification of cellulose membranes with sulfo ammonium zwitterionic vinyl monomer to improve hemocompatibility. Colloids and Surfaces B: Biointerfaces 30.

Kang et al., Surface modification and functionalization of electroactive polymer films via grafting of polyelectrolyte, polyampholyte and polymeric acids. Journal to Materials Science 1996, 31, 1295-1301.

Fujimoto et al., Ozone-induced graft polymerization onto polymer surface. J Polym Sci A Polym Chem 1993, 31, 1035-1043.

Liu et al., Grafting of Zwitterion from Cellulose Membranes via ATRP for Improving Blood Compatibility. Biomacromolecules 2009,10 (10), 2809-2816.

Villa-Diaz et al., Synthetic polymer coatings for long-term growth of human embryonic stem cells. Nat Biotechnol 2010, 28(6),581-3.

Yuan et al., Polyurethane vascular catheter surface grafted with zwitlerionic sulfobetaine monomer activated by ozone. Colloids and Surfaces B: Biointerfaces 35.

Yuan et al., Chemical graft polymerization of sulfobetaine monomer on polyurethane surface for reduction in platelet adhesion. Colloids Surf B Biointerfaces 2004,39 (1-2), 87-94.

Yuan et al., Platelet adhesion onto segmented polyurethane surfaces modified by carboxybetaine. J Biomater Sci Polym Ed 2003,14 (12), 1339-49.

Yuan et al., Grafting Sulfobetaine monomer onto the segmented poly(ether-urethane) surface to improve hemocompatibility. J Biomaterial Sci Polym Ed 2002, 13, 1081-92.

Yuan et al., Surface modification of SPEC films by ozone induced graft copolymerization to improve hemocompatibility. Colloids and Surfaces B: Biointerfaces 2003, 29, 247-256.

Zhang et al., Nonfouling Behavior of Polycarboxybetaine-Grafted Surfaces: Structural and Environmental Effects—Biomacromolecules (ACS Publications). Biomacromolecules (Web): Sep. 12, 2008, 10, 2686-92.

Odian, G., Polymerization Mechanism, Types of Polymers and Polymerizations, p. 6-7.

Salim et al., Studies of electroosmotic flow and the effects of protein adsorptiion in plasma-polymerized microchannel surfaces, Electrophoresis 2009, 30, 1877-1887.

Patent Cooperation Treaty, International Search Report for PCT/US2011/039790, dated Mar. 12, 2012, 4 pages.

Patent Cooperation Treaty, International Search Report for PCT/US2011/039792, dated Mar. 12, 2012, 6 pages.

Bell et al., Biomedical membranes from hydrogels and interpolymer complexes. Biopolymers II, 1995,122, 125-175.

Chapman et al., Polymeric Thin Films That Resist the Adsorption of Proteins and the Adhesion of Bacteria. Langmuir 2001, 17 (4), 1225-1233.

Kildal et al., Peroxide-initiated granfling of acrylaminde on to polyethylene surfaces, Journal of Applied Polymer Science, 1992, 44, 1893-1898.

Cheng et al., Zwitterionic carboxybetaine polymer surfaces and their resistance to long-term biofilm formation. Biomaterials 2009, 30 (28), 5234-40.

Cheng et al., Inhibition of bacterial adhesion and biofilm formation on zwitterionic surfaces. Biomaterials 2007, 28 (29), 4192-9.

Du et al., Grafted poly-(ethylene glycol) on lipid surfaces inhibits protein adsorption and cell adhesion. Biochimica et Biophysica Acta (BBA)—Biomembranes 1997, 1326 (2), 236-248.

Harder et al., Molecular Conformation in Oligo(ethylene glycol)-Terminated Self-Assembled Monolayers on Gold and Silver Surfaces Determines Their Ability to Resist Protein Adsorption. The Journal of Physical Chemistry B 1998, 102 (2), 426-436.

Haynie et al., Antimicrobial activities of amphiphilic peptides covalently bonded to a water-insoluble resin. Antimicrobial Agents and Chemotherapy 1995, 39 (2), 301-307.

Ignatova et al., Combination of electrografting and atom-transfer radical polymerization for making the stainless steel surface antibacterial and protein antiadhesive, Langmuir, 2005, 22(1), 255-262.

Massia et al., Immobilized RGD peptides on surface-grafted dextran promote biospecific cell attachment. J Biomed Mater Res 2001, 56 (3), 390-399.

Michel et al., Influence of PEG Architecture on Protein Adsorption and Conformation. Langmuir 2005, 21 (26), 12327-12332.

Sakharov et al., Catalytic oxidative deformylation of polyethylene glycols with the participation of molecular oxygen. Kinet Catal 2001, 42, 662-668.

Wang et al., Antifouling ultrafiltration membrane composed of polyethersulfone and sulfobetaine copolymer. Journal of Membrane Science 2006, 280, 343-350.

West et al., The biocompatibility of crosslinkable copolymer coatings containing sulfobetaines and phosphobetaines. Biomaterials 2004, 25 (7-8), 1195-204.

Wozney et al., Novel regulators of bone formation: molecular clones and activities. Science 1988, 242 (4885), 1528-1534.

(56) References Cited

OTHER PUBLICATIONS

Zhang et al., Surface grafted sulfobetaine polymers via atom transfer radical polymerization as superlow fouling coatings. J Phys Chem B 2006, 110 (22), 10799-804.

Zhang et al., Blood compatibility of surfaces with superlow protein adsorption. Biomaterials 2008, 29 (32), 4285-91.

Zhang et al., Superlow Fouling Sulfobetaine and Carboxybetaine Polymers on Glass Slides. Langmuir 2006, 22 (24), 10072-10077.

Jiang, Zwitterionic Separation Materials for Liquid Chromatography and Capillary Electrophoresis Synthesis, Characterization and Application for Inorganic Ion and Biomolecule Separations, PhD Dissertation, Umea University, Umea, Sweden, 63 pages.

Jun et al., Surface modification of segmented poly(ether urethane) by grafting sulfo ammonium zwitterionic monomer to improve hemocompatibilities, Colloids and Surfaces B: Biointerfaces, 2003, 28(1), 1-9.

Patent Cooperation Treaty, International Search Report for PCT/US2009/67013, dated Jun. 4, 2010, 4 pages.

\* cited by examiner

NON-FOULING, ANTI-MICROBIAL, ANTI-THROMBOGENIC GRAFT-FROM COMPOSITIONS

CROSS-REFERENCE TO RELATED APPLICATIONS

This application is a continuation of and claims priority to U.S. application Ser. No. 13/156,677 filed Jun. 9, 2011, which issued as U.S. Pat. No. 9,096,703, and claims priority to U.S. Patent Application Ser. No. 61/353,059, filed Jun. 9, 2010, the disclosures of which are incorporated herein by reference in its their entirety.

FIELD OF THE INVENTION

The present invention generally relates to articles of manufacture, such as medical devices, having a non-fouling surface comprising a polymeric material that is grafted from the article. The surface resists the adhesion of biological material.

BACKGROUND OF THE INVENTION

Many different materials have been investigated to resist non-specific protein adsorption. Chemistries utilized for this purpose include, but are not limited to: polyethers (e.g., polyethylene glycol), polysaccharides such as dextran, hydrophilic polymers such as polyvinylpyrrolidone or hydroxyethyl-methacrylate, heparin, intramolecular zwitterions or mixed charge materials, and hydrogen bond accepting groups such as those described in U.S. Pat. No. 7,276,286. The ability of these materials in preventing protein adsorption varies greatly between the chemistries. Of these materials, only a few resist fouling to the degree required for short-term in vivo application. However, the few materials appropriate for short-term application, when used for longer periods of time in complex media or in vivo, exhibit significant fouling or other degradation, making them unsuitable for long-term applications. Furthermore, surfaces coated with materials that resist in vivo degradation are often susceptible to a noticeable decrease in fouling resistance over time.

WO 2007/02493 describes grafting sulfobetaine and carboxybetaine from self-assembled monolayers on gold substrates or from silyl groups on glass substrates using atom transfer radical polymerization (ATRP). Gold and glass are not appropriate substrates for many medical devices used in vivo. Self-assembled monolayers, such as thiol-based monolayers, may be unstable since the thiol group is not stably bound to the substrate.

U.S. Pat. No. 6,358,557 to Wang et al. describes the graft polymerization of substrate surfaces, but not with a high density of a highly non-fouling polymeric material. A thermal initiator is used to initiate polymerization, typically at temperatures greater than 85° C. Such temperatures are generally not suitable for many medical devices, such as thin-walled polyurethane catheters. Further, the "salt out" method described is generally not suitable for grafting polymers such as zwitterionic polymers.

Jian et al., Colloids and Surfaces B: Biointerfaces 28, 1-9 (2003) describes the surface modification of segmented poly(ether urethane) by grafting sulfobetaine zwitterionic monomer, but not with a high density of non-fouling material. The resulting materials are not sufficiently non-fouling to be useful in medical device applications.

SUMMARY OF THE INVENTION

Among the various aspects of the present invention is the provision of medical devices and other articles having a non-fouling polymeric material grafted therefrom. Advantageously, the polymeric material may possess a range of polymeric backbones and substituents while providing the articles with a highly efficient, biocompatible, and non-fouling surface. In another embodiment, bioactive compositions are attached to the modified surface.

One aspect of the present invention is the provision of non-fouling polymeric materials for various substrates, such as polymers and metal oxides, which retain their activity in the presence of blood proteins and/or in vivo due to improved molecular structures. In one embodiment, bioactive compositions are attached to the non-fouling material.

Another aspect of the present invention is the provision of non-fouling compositions containing a high density of non-fouling polymeric material and/or wherein the inter-polymer chain distance of the non-fouling polymeric materials decreases the penetration of fouling molecules into the non-fouling polymer layer.

A further aspect of the present invention is the provision of grafted polymer layers for medical devices or other articles that are hydrophilic, but possess somewhat limited swelling capacity in water.

A further aspect of the present invention is the provision of graft-from methods for modifying a surface of an article of manufacture wherein the grafting is initiated from the article itself to provide the article with a polymeric grafted polymer layer that is relatively thick and relatively uniformly distributed on the surface of the article. In general, the resulting polymeric grafted polymer layers are generally thicker than self-assembled monolayer-initiated coatings and thus more fully cover the defects and irregularities in commercial biomaterials, including polymers and metals, so that non-fouling grafted polymer layers are effective in complex media and/or in vivo.

Briefly, therefore, one aspect of the present invention is an article of manufacture comprising a polymeric substrate having a surface and a polymer layer on the substrate surface. The substrate surface and the polymer layer, in combination, constitute a modified surface having a fibrinogen adsorption of less than about 125 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen. In one embodiment, the substrate surface and the polymer layer, in combination, constitute a modified surface having a fibrinogen adsorption of less than about 90 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen. In another embodiment, the substrate surface and the polymer layer, in combination, constitute a modified surface having a fibrinogen adsorption of less than about 70 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen. In another embodiment, the substrate surface and the polymer layer, in combination, constitute a modified surface having a fibrinogen adsorption of less than about 50 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen.

The present invention is further directed to an article of manufacture comprising a polymeric substrate having a surface and a layer of a graft-from polymer on the substrate surface. The substrate surface and the graft-from polymer, in combination, constitute a modified surface having a static contact angle of less than 25 degrees.

The present invention is further directed to an article of manufacture comprising a substrate having a surface and a polymer layer on the substrate surface. The substrate surface and the polymer layer, in combination, constitute a modified surface having a fibrinogen adsorption of less than about 125 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen. The polymer layer has a global average dry thickness of at least about 50 nm and the magnitude of the difference between the global average dry thickness of the polymer layer as determined by scanning electron microscopy (SEM) and the global average humidified thickness of the polymer layer as determined by environmental scanning electron microscopy (ESEM) is less than 200% of the global average dry thickness. In one such embodiment, the substrate surface and the polymer layer, in combination, constitute a modified surface having a fibrinogen adsorption of less than about 90 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen. In another such embodiment, the substrate surface and the polymer layer, in combination, constitute a modified surface having a fibrinogen adsorption of less than about 70 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen. In another such embodiment, the substrate surface and the polymer layer, in combination, constitute a modified surface having a fibrinogen adsorption of less than about 50 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen.

The present invention is further directed to an article of manufacture comprising a substrate having a surface and a polymer layer on the substrate surface. The substrate surface and the polymer layer, in combination, constitute a modified surface having a fibrinogen adsorption of less than about 125 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen. The article further comprises a solvent extractable polymerization initiator or degradation product thereof. In one such embodiment, the substrate surface and the polymer layer, in combination, constitute a modified surface having a fibrinogen adsorption of less than about 90 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen. In another such embodiment, the substrate surface and the polymer layer, in combination, constitute a modified surface having a fibrinogen adsorption of less than about 70 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen. In another such embodiment, the substrate surface and the polymer layer, in combination, constitute a modified surface having a fibrinogen adsorption of less than about 50 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen.

The present invention is further directed to an article of manufacture comprising a substrate having a surface and a polymer layer on the substrate surface. The substrate surface and the polymer layer, in combination, constitute a modified surface having a fibrinogen adsorption of less than about 125 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen. The polymer layer has a global average dry thickness that is at least equal to the global average $R_{rms}$ surface roughness of the substrate surface. In one such embodiment, the substrate surface and the polymer layer, in combination, constitute a modified surface having a fibrinogen adsorption of less than about 90 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen. In another such embodiment, the substrate surface and the polymer layer, in combination, constitute a modified surface having a fibrinogen adsorption of less than about 70 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen. In another such embodiment, the substrate surface and the polymer layer, in combination, constitute a modified surface having a fibrinogen adsorption of less than about 50 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen.

The present invention is further directed to an article of manufacture comprising a substrate having a surface and a polymer layer on the substrate surface. The substrate surface and the polymer layer, in combination, constitute a modified surface having a fibrinogen adsorption of less than about 125 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen. In one embodiment, the polymer layer has a global average $R_{rms}$ surface roughness that is less than 300% of the global average $R_{rms}$ surface roughness of the substrate surface. In one embodiment, the polymer layer has a global average $R_{rms}$ surface roughness that is less than the 200% of the global average $R_{rms}$ surface roughness of the substrate surface. In another embodiment, the polymer layer has a global average $R_{rms}$ surface roughness that is less than 150% of the global average $R_{rms}$ surface roughness of the substrate surface. In another embodiment, the polymer layer has a global average $R_{rms}$ surface roughness that is less than the global average $R_{rms}$ surface roughness of the substrate surface. In each of the forgoing embodiments, the substrate surface and the polymer layer, in combination, may constitute a modified surface having a fibrinogen adsorption of less than about 90 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen. In each of the forgoing embodiments, the substrate surface and the polymer layer, in combination, constitute a modified surface having a fibrinogen adsorption of less than about 70 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen. In each of the forgoing embodiments, the substrate surface and the polymer layer, in combination, may constitute a modified surface having a fibrinogen adsorption of less than about 50 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen. For example, in one embodiment, the substrate surface and the polymer layer, in combination, constitute a modified surface having a fibrinogen adsorption of less than about 50 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen and the polymer layer has a global average $R_{rms}$ surface roughness that is less than the global average $R_{rms}$ surface roughness of the substrate surface.

The present invention is further directed to an article of manufacture comprising a substrate having a surface and a polymer layer on the substrate surface. The substrate surface and the polymer layer, in combination, constitute a modified surface having a fibrinogen adsorption of less than about 125 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen. The polymer layer has a global average dry thickness wherein the standard deviation of the global average dry thickness of the polymer layer does not exceed 100% of the global average dry thickness of the polymer layer. In one such embodiment, the substrate surface and the polymer layer, in combination, constitute a modified surface having a fibrinogen adsorption of less than about 90 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen. In another such embodiment, the substrate surface and the polymer layer, in combination, constitute a modified surface having a fibrinogen adsorption of less than about 70 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen. In another such embodiment, the substrate surface and the polymer layer, in combination, constitute a modified surface having a fibrinogen adsorption of less than about 50 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen.

The present invention is further directed to a process for grafting a polymer from an article of manufacture comprising a substrate having a surface, a bulk beneath the surface, a near-surface zone lying between the surface and the bulk. The process comprises incorporating a polymerization initiator into the near-surface zone and graft polymerizing a polymer from the article.

The present invention is further directed to a process for grafting a polymer from an article of manufacture comprising a substrate having a surface, a bulk beneath the surface, a near-surface zone lying between the surface and the bulk. The process comprises incorporating a polymerization initiator into the near-surface zone and graft polymerizing a polymer from the article wherein the substrate surface has a global average $R_{rms}$ surface roughness of at least 200 nm and graft polymerization is continued until the polymer has a global average dry thickness that exceeds the global average $R_{rms}$ surface roughness of the substrate surface. In one such embodiment, the substrate surface has a global average $R_{rms}$ surface roughness of at least 150 nm and graft polymerization is continued until the polymer has a global average dry thickness that exceeds the global average $R_{rms}$ surface roughness of the substrate surface. In another such embodiment, the substrate surface has a global average $R_{rms}$ surface roughness of at least 100 nm and graft polymerization is continued until the polymer has a global average dry thickness that exceeds the global average $R_{rms}$ surface roughness of the substrate surface. In another such embodiment, the substrate surface has a global average $R_{rms}$ surface roughness of at least 50 nm and graft polymerization is continued until the polymer has a global average dry thickness that exceeds the global average $R_{rms}$ surface roughness of the substrate surface.

For articles such as microfluidic devices and woven meshes which are designed to have channels or pores having a size (e.g., diameter or width) in the range of 100 nm to 1 millimeter, it may be desired to have a global average dry thickness of the graft polymer layer that is less than 10% of the channel or pore size of the device. Without being bound by any theory, having a global average dry thickness substantially smaller than the channel or pore size may reduce impact on the function of the device. In certain embodiments, it is desired to have a global average dry thickness of the graft polymer layer that is less than 5% of the channel or pore size of the device. In certain embodiments, it is desired to have a global average dry thickness of the graft polymer layer that is less than 3% of the channel or pore size of the device. In certain embodiments, it is desired to have a global average dry thickness of the graft polymer layer that is less than 1% of the channel or pore size of the device. In certain embodiments, it is desired to have a global average dry thickness of the graft polymer layer that is less than 0.1% of the channel or pore size of the device.

The present invention is further directed to a process for grafting a polymer from an article comprising a substrate having a surface, a bulk beneath the surface, and a near-surface zone lying between the surface and the bulk. The process comprises incorporating a polymerization initiator into the near-surface zone and graft polymerizing a polymer from the substrate surface to form a polymer layer comprising the grafted polymer, the polymer layer having a global average dry thickness of at least about 200 nm. The magnitude of the difference between the global average dry thickness of the polymer layer as determined by scanning electron microscopy (SEM) and the global average humidified thickness of the polymer layer as determined by environmental scanning electron microscopy (ESEM) is less than 200% of the global average dry thickness. In one such embodiment, the polymer layer has a global average dry thickness of at least about 150 nm and the magnitude of the difference between the global average dry thickness of the polymer layer as determined by scanning electron microscopy (SEM) and the global average humidified thickness of the polymer layer as determined by environmental scanning electron microscopy (ESEM) is less than 200% of the global average dry thickness. In another such embodiment, the polymer layer has a global average dry thickness of at least about 100 nm and the magnitude of the difference between the global average dry thickness of the polymer layer as determined by scanning electron microscopy (SEM) and the global average humidified thickness of the polymer layer as determined by environmental scanning electron microscopy (ESEM) is less than 200% of the global average dry thickness. In another such embodiment, the polymer layer has a global average dry thickness of at least about 50 nm and the magnitude of the difference between the global average dry thickness of the polymer layer as determined by scanning electron microscopy (SEM) and the global average humidified thickness of the polymer layer as determined by environmental scanning electron microscopy (ESEM) is less than 200% of the global average dry thickness.

The present invention is further directed to a process for grafting a polymer from an article comprising a substrate having a surface, a bulk beneath the surface, and a near-surface zone lying between the surface and the bulk. The process comprises incorporating a polymerization initiator and optionally other species such as ligands and/or catalysts into the near-surface zone and graft polymerizing a polymer from the substrate surface to form a polymer layer comprising the grafted polymer, the polymer layer having a global average dry thickness that is at least equal to the global average $R_{rms}$ surface roughness of the substrate surface.

Other objects and features will be in part apparent and in part pointed out hereinafter.

Abbreviations and Definitions

The following definitions and methods are provided to better define the present invention and to guide those of ordinary skill in the art in the practice of the present invention. Unless otherwise noted, terms are to be understood according to conventional usage by those of ordinary skill in the relevant art.

When introducing elements of the present invention or the preferred embodiment(s) thereof, the articles "a," "an," "the" and "said" are intended to mean that there are one or more of the elements. The terms "comprising," "including" and "having" are intended to be inclusive and mean that there may be additional elements other than the listed elements.

Aliphatic: unless otherwise indicated, "aliphatic" or "aliphatic group" means an optionally substituted, non-aromatic hydrocarbon moiety. The moiety may be, for example, linear, branched, or cyclic (e.g., mono or polycyclic such as fused, bridging, or spiro-fused polycyclic), or a combination thereof. Unless otherwise specified, aliphatic groups contain 1-20 carbon atoms.

Alkyl: unless otherwise indicated, the alkyl groups described herein are preferably lower alkyl containing from one to eight carbon atoms in the principal chain and up to 20 carbon atoms. They may be linear, branched or cyclic and include methyl, ethyl, propyl, butyl, hexyl and the like.

Amino: unless otherwise indicated, the term "amino" as used herein alone or as part of another group denotes the moiety —$NR^1R^2$ wherein $R^1$, and $R^2$ are independently hydrogen, hydrocarbyl, substituted hydrocarbyl or heterocyclo.

Ammonium: unless otherwise indicated, the term "ammonium" as used herein alone or as part of another group denotes the moiety —$N^+R^1R^2R^3$ wherein $R^1$, $R^2$ and $R^3$ are independently hydrogen, hydrocarbyl, substituted hydrocarbyl or heterocyclo.

Amide or Amido: unless otherwise indicated, the "amide" or "amido" moieties represent a group of the formula —$CONR^1R^2$ wherein $R^1$ and $R^2$ are as defined in connection with the term "amino." "Substituted amide," for example, refers to a group of the formula —$CONR^1R^2$ wherein at least one of $R^1$ and $R^2$ are other than hydrogen. "Unsubstituted amido," for example, refers to a group of the formula —$CONR^1R^2$, wherein $R^1$ and $R^2$ are each hydrogen.

Anionic Monomer, Anionic Monomeric Unit or Anionic Repeat Unit: unless otherwise indicated, an "anionic monomer," "anionic monomeric unit" or "anionic repeat unit" is a monomer or monomeric unit bearing an anion or other anionic species, e.g., a group that is present in a negatively charged state or in a non-charged state, but in the non-charged state is capable of becoming negatively charged, e.g., upon removal of an electrophile (e.g., a proton (H+), for example in a pH dependent manner) or a protecting group (e.g., a carboxylic acid ester), or the addition of a nucleophile. In certain instances, the group is substantially negatively charged at an approximately physiological pH but undergoes protonation and becomes substantially neutral at a weakly acidic pH. The non-limiting examples of such groups include carboxyl groups, barbituric acid and derivatives thereof, xanthine and derivatives thereof, boronic acids, phosphinic acids, phosphonic acids, sulfinic acids, sulfonic acids, phosphates, and sulfonamides.

Anionic species or Anionic moiety: unless otherwise indicated, an "Anionic species" or an "Anionic moiety" is a group, residue or molecule that is present in a negatively charged or non-charged state, but in the non-charged state is capable of becoming negatively charged, e.g., upon removal of an electrophile (e.g., a proton (H+), for example in a pH dependent manner) or other protecting group (e.g., a carboxylic acid ester), or the addition of a nucleophile. In certain instances, the group, residue or molecule is substantially negatively charged at an approximately physiological pH but undergoes protonation and becomes substantially neutral at a weakly acidic pH.

Antibiofilm activity: unless otherwise indicated, "antibiofilm activity" may be quantified, for example, using a standard continuous flow assay. In one such assay, samples may be pre-incubated with 50% fetal bovine serum for 18-20 hours at 120 RPM at 37° C. Following preincubation, samples are then exposed to a subculture of bacteria via a modified CDC (mCDC) to make a bacterial suspension of $10^6$ Cfu/mL in 1×PBS. The reactor is run in batch mode for 2 hours at 37° C. with agitation. Thereafter, the samples are transferred to a fresh reactor a suitable growth media for where flow of the sterile media (8 mL/min) runs 20-23 hours with agitation. In one preferred embodiment, the bacterial strain is Staphylococcus epidermidis (S. epidermidis, ATCC 35984), and the growth media used is 1:10 Tryptic soy broth (TSB)+0.25 wt % glucose. In an alternate preferred embodiment, the bacterial strain is Escherichia coli (E. coli, ATCC 25922) and the growth media is M63 media supplemented with 1 mM $MgSO_4$, 0.2% glucose, and 0.5% casamino acids. After incubation, the samples are rinsed five times in 100 mL of 1×PBS to remove bacteria not tightly attached. Then, accumulated bacteria on materials are macroscopically rated for biofilm surface coverage and are removed by sonication in a new solution of PBS and the total number of bacterial cells quantified through dilution plating. Preferably at least a 1, 2, 3 or 4 log reduction in bacterial count is found on the article with the non-fouling polymer layer relative to a reference substrate, that is, the same or an otherwise functionally equivalent substrate lacking the non-fouling polymer layer. An article that has a 1 log reduction in adhered bacteria relative to a reference substrate is said to have antibiofilm activity of 1 log. An article that has a 2 log reduction in adhered bacteria relative to a reference substrate is said to have antibiofilm activity of 2 log, and so forth.

Antimicrobial: unless otherwise indicated, "antimicrobial" refers to molecules and/or compositions that kill (i.e., microbicidal), inhibit the growth of (i.e., microbistatic), and/or prevent fouling by, microorganisms including bacteria, yeast, fungi, mycoplasma, viruses or virus infected cells, and/or protozoa. Antimicrobial activity with respect to bacteria may be quantified, for example, using a standard assay. In one such assay, samples may be pre-incubated with 50% fetal bovine serum for 18-20 hours at 120 RPM at 37° C. Following preincubation, samples are placed in *Staphylococcus aureus* (*S. aureus*, ATCC 25923) which has been diluted from an overnight culture to a planktonic concentration of $1-3\times10^5$ CFU/mL in 1% tryptone soy broth (TSB) diluted in 1×PBS or other suitable media. Samples are incubated with bacteria for 24-26 hrs with agitation (120 rpm) at 37° C. The concentration of TSB or other media can vary with the organism being used. After incubation, the samples are placed in 3 mL PBS for 5 min at 240 RPM at 37° C. to remove bacteria not tightly attached to the material. Then, accumulated bacteria on materials are removed by sonication in a new solution of PBS and the total number of bacterial cells are quantified through dilution plating. Preferably at least a 1, 2, 3 or 4 log reduction in bacterial count occurs relative to colonization on a reference substrate, that is, the same or an otherwise functionally equivalent substrate lacking the non-fouling polymer layer. A surface that has a lower bacterial count on it than the reference substrate may be said to reduce microbial colonization.

Antimicrobial peptide (AmP): unless otherwise indicated, "antimicrobial peptide" (or "AmP") refers to oligopeptides, polypeptides, or peptidomimetics that kill (i.e., are microbicidal) or inhibit the growth of (i.e., are microbistatic) microorganisms including bacteria, yeast, fungi, mycoplasma, viruses or virus infected cells, and/or protozoa.

Anti-thrombogenic: unless otherwise indicated, "anti-thrombogenic" refers to the ability of a composition to resist thrombus formation. Anti-thrombogenic activity can be evaluated using an ex-vivo flow loop model of thrombosis. Briefly, up to 10 liters of fresh blood are collected from a single animal (bovine). This blood is heparinized to prevent coagulation, filtered to remove particulates, and autologous radio-labeled platelets are added. Within eight hours after blood harvesting, coated and uncoated articles are placed in a flow loop circuit, which pumps blood from a bath over the article and then back into the bath. A second internal flow loop circuit can be established for an article containing a lumen by connecting the two ports of the article through a 2nd peristaltic pump. The size of tubing into which the article is placed and speed of the blood flow may be adjusted based on the size of the article being tested.

Aryl: unless otherwise indicated, the term "aryl" or "aryl group" refers to optionally substituted monocyclic, bicyclic, and tricyclic ring systems having a total of five to fourteen ring members, wherein at least one ring in the system is aromatic and wherein each ring in the system contains three to seven ring members. The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

Attached: unless otherwise indicated, two moieties or compounds are "attached" if they are held together by any interaction including, by way of example, one or more covalent bonds, one or more non-covalent interactions (e.g., hydrogen bonds, ionic bonds, static forces, van der Waals interactions, combinations thereof, or the like), or a combination thereof.

Bioactive Agent/Active Agent/Biomolecule: unless otherwise indicated, "bioactive agent" or "active agent" or "biomolecule," used herein synonymously, refers to any organic or inorganic therapeutic, prophylactic or diagnostic agent that actively or passively influences a biological system. For example, a bioactive agent can be an amino acid, antimicrobial peptide, immunoglobulin, an activating, signaling or signal amplifying molecule, including, but not limited to, a protein kinase, a cytokine, a chemokine, an interferon, tumor necrosis factor, growth factor, growth factor inhibitor, hormone, enzyme, receptor-targeting ligand, gene silencing agent, ambisense, antisense, an RNA, a living cell, cohesin, laminin, fibronectin, fibrinogen, osteocalcin, osteopontin, or osteoprotegerin. Bioactive agents can be aptamers, proteins, glycoproteins, peptides, oligliopeptides, polypeptides, polymers, inorganic compounds, organometallic compounds, organic compounds or any synthetic or natural, chemical or biological compound.

Biocompatibility: unless otherwise indicated, "biocompatibility" is the ability of a material to perform with an appropriate host response in a specific situation. This can be evaluated using International Standard ISO 10993. Biocompatible compositions described herein are preferably substantially non-toxic.

Biological fluids: unless otherwise indicated, "biological fluids" are fluids produced by organisms containing proteins and/or cells, as well as fluids and excretions from microbes. This includes, but is not limited to, blood, saliva, urine, cerebrospinal fluid, tears, semen, lymph, ascites, sputum, bone marrow, synovial fluid, aqueous humor, cerumen, broncheoalveolar lavage fluid, prostatic fluid, cowper's fluid or pre-ejaculatory fluid, sweat, fecal matter, cyst fluid, pleural and peritoneal fluid, chyme, chyle, bile, intestinal fluid, pus, sebum, vomit, mucosal secretion, stool water, pancreatic juice, lavage fluids from sinus cavities, bronchopulmonary aspirates, or any derivative thereof (e.g., serum, plasma).

Block Copolymer: unless otherwise indicated, a "block copolymer" comprises two or more homopolymer or copolymer subunits linked by covalent bonds. Block copolymers with two or three distinct blocks are called diblock copolymers and triblock copolymers, respectively. A schematic generalization of a diblock copolymer is represented by the formula $[A_aB_bC_c\ldots]_m-[X_xY_yZ_z\ldots]_n$ wherein each letter stands for a constitutional or monomeric unit, and wherein each subscript to a constitutional unit represents the mole fraction of that unit in the particular block, the three dots indicate that there may be more (there may also be fewer) constitutional units in each block and m and n indicate the molecular weight of each block in the diblock copolymer. As suggested by the schematic, in some instances, the number and the nature of each constitutional unit is separately controlled for each block. The schematic is not meant and should not be construed to infer any relationship whatsoever between the number of constitutional units or the number of different types of constitutional units in each of the blocks. Nor is the schematic meant to describe any particular number or arrangement of the constitutional units within a particular block. In each block the constitutional units may be disposed in a purely random, an alternating random, a regular alternating, a regular block or a random block configuration unless expressly stated to be otherwise. A purely random configuration, for example, may have the non-limiting form: X-X-Y-Z-X-Y-Y-Z-Y-Z-Z-Z . . . . A non-limiting, exemplary alternating random configuration may have the non-limiting form: X-Y-X-Z-Y-X-Y-Z-Y-X-Z . . . , and an exemplary regular alternating configuration may have the non-limiting form: X-Y-Z-X-Y-Z-X-Y-Z . . . . An exemplary regular block configuration may have the following non-limiting configuration: . . . X-X-X-Y-Y-Y-Z-Z-Z-X-X-X . . . , while an exemplary random block configuration may have the non-limiting configuration: . . . X-X-X-Z-Z-X-X-Y-Y-Y-Y-Z-Z-Z-X-X-Z-Z-Z- . . . . In a gradient polymer, the content of one or more monomeric units increases or decreases in a gradient manner from the α end of the polymer to the ω end. In none of the preceding generic examples is the particular juxtaposition of individual constitutional units or blocks or the number of constitutional units in a block or the number of blocks meant nor should they be construed as in any manner bearing on or limiting the actual structure of block copolymers forming a micelle described herein. As used herein, the brackets enclosing the constitutional units are not meant and are not to be construed to mean that the constitutional units themselves form blocks. That is, the constitutional units within the square brackets may combine in any manner with the other constitutional units within the block, i.e., purely random, alternating random, regular alternating, regular block or random block configurations. The block copolymers described herein are, optionally, alternate, gradient or random block copolymers. In some embodiments, the block copolymers are dendrimer, star or graft copolymers.

Branched: unless otherwise indicated, "branched" refers to a polymer structure in which a polymer chain divides into two or more polymer chains.

Brushes/Polymer Brushes: unless otherwise indicated, "brushes" or "polymer brushes" are used herein synonymously and refer to polymer chains that are bound to a surface generally through a single point of attachment using graft-from techniques. The polymers can be end-grafted (attached via a terminal group) or attached via a side chain or a position in the polymer chain other than a terminal position. The polymers can be linear or branched. For example, the polymer chains described herein can contain a plurality of side chains that contain zwitterionic groups. The side chains can consist of a single non-fouling moiety or monomer and/or a non-fouling oligomer (e.g., 2-10 monomeric residues) or polymer (e.g., >10 monomeric residues).

Carboxyammonium: unless otherwise indicated, a "carboxyammonium" moiety is a zwitterionic moiety comprising carboxylate and ammonium functionality and includes, for example, carboxyammonium monomers, carboxyammonium oligomers, carboxyammonium polymers, carboxyammonium repeat units, and other carboxyammonium-containing materials. Carboxybetaine monomers, oligomers, polymers, repeat units and other carboxybetaine materials are exemplary carboxyammonium moieties.

Cationic Monomer, Cationic Monomeric Unit or Cationic Repeat Unit: unless otherwise indicated, a "cationic monomer," "cationic monomeric unit" or "cationic repeat unit" is a monomer or a monomeric or repeat unit (the terms "monomeric unit" and "repeat unit" being used interchangeably) bearing a cation or other cationic species, e.g., a moiety capable of having a positive charge upon addition of an electrophile (e.g., a proton (H+) or an alkyl cation, for example in a pH dependent manner) or removal of a protecting group or a nucleophile).

Cationic species or Cationic Moiety: unless otherwise indicated, a "Cationic species" or a "Cationic Moiety" is a group, residue or molecule that is present in a positively charged or non-charged state, but in the non charged state is capable of becoming positively charged, e.g., upon addition of an electrophile (e.g., a proton (H+), for example in a pH dependent manner) or removal of a protecting group or a nucleophile. In certain instances, the group, residue or molecule is permanently charged, e.g., comprises a quaternary nitrogen atom.

Coating: unless otherwise indicated, "coating" refers to any temporary, semi-permanent or permanent layer, or layers, treating or covering a surface. The coating may be a chemical modification of the underlying substrate or may involve the addition of new materials to the surface of the substrate. It includes any increase in thickness to the substrate or change in surface chemical composition of the substrate.

Complex Media: unless otherwise indicated, "complex media" refers to biological fluids or solutions containing proteins or digests of biological materials. Examples include, but are not limited to, cation-adjusted Mueller Hinton broth, tryptic soy broth, brain heart infusion, or any number of complex media, as well as any biological fluid.

Copolymer: unless otherwise indicated, "copolymer" refers to a polymer derived from two, three or more monomeric species and includes alternating copolymers, periodic copolymers, random copolymers, statistical copolymers and block copolymers.

Cysteine: unless otherwise indicated, "cysteine" refers to the amino acid cysteine or a synthetic analogue thereof, wherein the analogue contains a free sulfhydryl group.

Degradation Products: unless otherwise indicated, "degradation products" are atoms, radicals, cations, anions, or molecules other than water formed as the result of hydrolytic, oxidative, enzymatic, or other chemical processes.

Dry Thickness: unless otherwise indicated, "Dry Thickness," as used herein in connection with a polymer layer, shall mean the thickness of the polymer layer using a scanning electron microscope (SEM). To measure dry thickness, the sample is freeze fractured for imaging by being submerged in liquid nitrogen then cracked with an ultra microtome blade. For metal substrates, they may be scored with a notch before a primer or the non-fouling polymer is applied to make freeze fracturing easier. The freeze fracturing should break the article at a plane approximately orthogonal to the polymer modified surface in order to measure the thickness of the polymer layer normal to the substrate. The samples are sputter coated in gold for 90 seconds using a sputter coater and then imaged under high vacuum at 5 kV using an SE2 detector under a Field Emission Scanning Electron Microscope (SEM). Exemplary microtome blades include the Leica Ultracut UCT Ultramicrotome, exemplary sputter coaters include the Cressington 208HR, exemplary SEMs include the Supra55VP FESEM, Zeiss. Dry thickness may be approximated by analyzing intensity of chemical signals in the grafted polymer, for instance, through the use of ATR-FTIR.

Fibrinogen Adsorption Assay: unless otherwise indicated, a "Fibrinogen Adsorption Assay" is an assay used to assess the capacity of a surface for fibrinogen. In the assay, test samples are placed in a suitable sized container, which may be a 96-well manifold, microcentrifuge tube, or other container. The volumes in the following are appropriate for a deep 96-well plate, but may be scaled to properly cover a device being tested. The samples are sterilized with 70% ethanol solution for thirty minutes and the test groups run with an n per run of 3-4. The sample container is blocked with 20 mg/mL Bovine Serum Albumin (BSA) in 1×PBS for 1 hour at 4° C., followed by three rinses with 1×PBS before samples are added. The sample is exposed to a solution containing 70 µg/mL unlabeled human fibrinogen, 1.4 µg/mL I-125 radiolabeled human fibrinogen, 35-55 µg/mL BSA in water, optionally tri-sodium citrate, and optionally sodium chloride. The BSA is a common agent co-lyophilized with the radiolabeled fibrinogen. Optionally, the BSA and radiolabeled fibrinogen may have been dissolved from a lyophilized form that contains tri-sodium citrate and sodium chloride. The samples are incubated for one hour at 37° C. on an orbital shaker at 150 RPM. The test solution is then removed and four 1-minute rinses with a 10 mM NaI and one 1-minute rinse with 1×PBS is performed. The samples are loaded into a gamma counter. The counter measures the radioactivity in I-125 counts per minute for each sample and this data is used to calculate the absolute fibrinogen adsorption or a percent reduction of the non-fouling polymer layer samples versus a reference substrate, that is, the same or an otherwise functionally equivalent substrate lacking the non-fouling polymer layer. The percent reduction is equal to: (1−non-fouling sample CPM/Average CPM of the reference substrate)*100%.

Global Average Dry Thickness: unless otherwise indicated, "Global Average Dry Thickness," as used herein in connection with a polymer layer, shall mean the mean calculated by averaging the Local Average Dry Thickness of at least 3, and preferably at least 5, representative locations spaced approximately evenly across the portion of the article carrying the polymer layer. For example, if a polymer layer is applied to the indwelling portion of a catheter, the representative locations are approximately evenly spaced across the indwelling portion of the catheter. It is preferred to measure the thickness at representative points across the longest dimension of the portion of the article that is covered with the polymer layer. The standard deviation of the Global Average Dry Thickness is found by calculating the standard deviation of the Local Average Dry Thickness across at least 5, and preferably at least 10, representative locations spaced approximately evenly across the portion of the article carrying the polymer layer.

Global Average Humidified Thickness: unless otherwise indicated, "Global Average Humidified Thickness," as used herein in connection with a polymer layer, shall mean the mean calculated by averaging the Local Average Humidified Thickness of at least 3, and preferably at least 5, representative locations spaced approximately evenly across the portion of the article carrying the polymer layer. For example, if a polymer layer is applied to the indwelling portion of a catheter, the representative locations are approximately evenly spaced across the indwelling portion of the catheter. It is preferred to measure the thickness at representative points across the longest dimension of the portion of the article that is covered with the polymer layer. The standard deviation of the Global Average Humidified Thickness is found by calculating the standard deviation of the Local Average Humidified Thickness across at least 5, and preferably at least 10, representative locations spaced approximately evenly across the portion of the article carrying the polymer layer.

Global Average $R_{rms}$ Surface Roughness: unless otherwise indicated, "Global Average $R_{rms}$ Surface Roughness," as used herein in connection with a polymer layer, shall mean the mean calculated by averaging the $R_{rms}$ surface roughness of at least 5, and preferably at least 10, representative locations spaced approximately evenly across the portion of the article carrying the polymer layer. For example, if a polymer layer is applied to the indwelling portion of a catheter, the representative locations are approximately evenly spaced across the indwelling portion of the catheter. It is preferred to measure the thickness at representative points across the longest dimension of the portion of the article that is covered with the polymer layer. The standard deviation of the Global Average $R_{rms}$ Surface Rroughness is found by calculating the standard deviation of the Local Average $R_{rms}$ Surface Roughness across at least 5, and preferably at least 10, representative locations spaced approximately evenly across the portion of the article carrying the polymer layer.

Graft: unless otherwise indicated, the term "graft," as used herein in connection with a polymer, means the modification of the surface of a material with a polymer by a "graft-from", "graft-through", or a "graft-to" approach, or a combination thereof to form a grafted polymer.

Graft-from method: unless otherwise indicated, the term "graft-from," as used herein in connection with a method for the modification of a material with a polymer, shall mean the in situ polymerization and growth of a polymer at the surface of, or within a material.

Graft-from polymer: unless otherwise indicated, the term "graft-from polymer," as used herein, shall mean a polymer formed by a graft-from method.

Graft-through method: unless otherwise indicated, the term "graft-through," as used herein in connection with a method for the modification of a material with a polymer, shall mean the in situ polymerization of monomers in the neighborhood of the material that may polymerize through functional groups presented from the material surface. For example, the material may have vinyl groups presented from the surface through which polymerization occurs.

Graft-through polymer: unless otherwise indicated, the term "graft-through polymer," as used herein, shall mean a polymer formed by a graft-through method.

Graft-to method: unless otherwise indicated, the term "graft-to," as used herein in connection with a method for the modification of a material with a polymer shall mean the modification of the surface of a material with a presynthesized polymer Graft-to polymer: unless otherwise indicated, the term "graft-to polymer," as used herein, shall mean a grafted polymer formed by a graft-to method.

Heteroalkyl: unless otherwise indicated, the term "heteroalkyl" means an alkyl group wherein at least one of the backbone carbon atoms is replaced with a heteroatom.

Heteroaryl: unless otherwise indicated, the term "heteroaryl" means an aryl group wherein at least one of the ring members is a heteroatom, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto (i.e., =O), hydroxy, protected hydroxy, acyl, acyloxy, alkoxy, alkenoxy, alkynoxy, aryloxy, halogen, amido, amino, nitro, cyano, thiol, ketals, acetals, esters and ethers.

Heteroatom: unless otherwise indicated, the term "heteroatom" means an atom other than hydrogen or carbon, such as a chlorine, iodine, bromine, oxygen, sulfur, nitrogen, phosphorus, boron, arsenic, selenium or silicon atom.

Heterocyclo: unless otherwise indicated, the terms "heterocyclo" and "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

Heterohydrocarbyl: unless otherwise indicated, the term "heterohydrocarbyl" means a hydrocarbyl group wherein at least one of the chain carbon atoms is replaced with a heteroatom.

Humidified Thickness: unless otherwise indicated, "humidified thickness," as used herein in connection with a polymer layer, shall mean the thickness of the polymer layer using an environmental scanning electron microscope (ESEM and approximately 26% relative humidity). To measure humidified thickness, the sample is freeze fractured for imaging by being submerged in liquid nitrogen then cracked with an ultra microtome blade. The freeze fracturing should break the article at a plane orthogonal to the polymer modified surface in order to measure the thickness of the polymer layer normal to the substrate. After fracturing, the samples are soaked in water for at least one hour and then submerged in liquid nitrogen and fixed to a cold stage at $-8°$ C. to $-12°$ C. The samples are then imaged using a VPSE detector at the highest resolvable humidity (approximately 26% or 81 Pa) under a Scanning Electron Microscope (SEM) with an Environmental Scanning Electron Microscope (E-SEM). Exemplary microtome blades include the Leica Ultracut UCT Ultramicrotome, exemplary SEMs include the Supra55VP FESEM, Zeiss, and exemplary E-SEMs include the Zeiss EVO 55.

Hydrocarbon or Hydrocarbyl: unless otherwise indicated, the terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms Hydrophilic: unless otherwise indicated, "hydrophilic" refers to solvents, molecules, compounds, polymers, mixtures, materials, or functional groups which have an affinity for water. Such materials typically include one or more hydrophilic functional groups, such as hydroxyl, zwitterionic, carboxy, amino, amide, phosphate, sulfonyl, hydrogen bond forming, and/or ether groups.

Hydrophobic: unless otherwise indicated, "hydrophobic" refers to solvents, molecules, compounds, polymers, mixtures, materials, or functional groups that are repelled by water. Such materials typically contain non-polar functional groups.

Immobilization/Immobilized: unless otherwise indicated, "immobilization" or "immobilized" refers to a material or bioactive agent that is covalently or non-covalently attached directly or indirectly to a substrate. "Co-immobilization" refers to immobilization of two or more agents.

Initiator: unless otherwise indicated, "initiator" refers to a substance or a combination of substances that can produce a radical or other species under relatively mild conditions and promote polymerization reactions. For example, redox pairs as described elsewhere herein may be an initiator.

Local Average Dry Thickness: unless otherwise indicated, "Local Average Dry Thickness" is the mean Dry Thickness calculated by averaging Dry Thickness measurements of at least 3, and preferably at least 5, representative locations spaced approximately evenly across a cross section of the article that spans approximately 10-40 micrometers. The standard deviation of the Local Average Dry Thickness is determined by calculating the standard deviation of the Dry Thickness across at least 5, and more preferably at least 10, representative locations spaced approximately evenly across a cross section of article that spans approximately 10-40 micrometers.

Local Average Humidified Thickness: unless otherwise indicated, "Local Average Humidified Thickness" is the mean Humidified Thickness calculated by averaging Humidified Thickness measurements of at least 3, and preferably at least 5, representative locations spaced approximately evenly across a cross section of the article that spans approximately 10-40 micrometers. The standard deviation of the Local Average Humidified Thickness may be determined by calculating the standard deviation of the Humidified Thickness across of at least 5, and preferably at least 10, representative locations spaced approximately evenly across a cross section of article that spans approximately 10-40 micrometers.

Membrane-Targeting Antimicrobial Agent: unless otherwise indicated, "membrane-targeting antimicrobial agent" refers to any antimicrobial agent that retains its bactericidal or bacteriostatic activity when immobilized on a substrate and can therefore be used to create an immobilized antimicrobial surface. In one embodiment, the membrane-targeting antimicrobial agent is an antimicrobial peptide, and in another embodiment it is a quaternary ammonium compound or polymer.

Non-Degradable: unless otherwise indicated, "non-degradable" refers to material compositions that do not react significantly within a biological environment either hydrolytically, reductively, enzymatically or oxidatively to cleave into smaller or simpler components.

Non-Fouling Composition/Non-Fouling Material/Non-Fouling Polymer/Non-Fouling Polymer Layer: unless otherwise indicated, a "non-fouling composition" or "non-fouling material" or "non-fouling polymer" or "Non-fouling polymer layer" as used interchangeably herein, is a composition that provides or increases the protein resistance of a surface of an article to which the composition is attached. For example, when attached to a substrate such a composition may resist the adhesion of proteins, including blood proteins, plasma, cells, tissue and/or microbes to the substrate relative to the amount of adhesion to a reference substrate, that is, the same or an otherwise functionally equivalent substrate lacking the composition. Preferably, a substrate surface will be substantially non-fouling in the presence of human blood. Preferably the amount of adhesion will be decreased 20%, 30%, 40%, 50%, 60%, 70%, 80%, or more, for example, 85%, 90%, 95%, 99%, 99.5%, 99.9%, or more, relative to the reference substrate. One particularly preferred measure of the non-fouling character or protein resistance of a surface is the amount of fibrinogen adsorbed in a Fibrinogen Adsorption Assay as described herein.

Preferably, the amount of adsorbed fibrinogen using the Fibrinogen Adsorption Assay described herein is <125 ng/cm$^2$, <90 ng/cm$^2$, <70 ng/cm$^2$, <50 ng/cm$^2$, <30 ng/cm$^2$, <20 ng/cm$^2$, <15 ng/cm$^2$, <12 ng/cm$^2$, <10 ng/cm$^2$, <8 ng/cm$^2$, <6 ng/cm$^2$, <4 ng/cm$^2$, <2 ng/cm$^2$, <1 ng/cm$^2$, <0.5 ng/cm$^2$, or <0.25 ng/cm$^2$.

Non-Naturally Occurring Amino Acid: unless otherwise indicated, "non-naturally occurring amino acid" refers to any amino acid that is not found in nature. Non-natural amino acids include any D-amino acids, amino acids with side chains that are not found in nature, and peptidomimetics. Examples of peptidomimetics include, but are not limited to, b-peptides, g-peptides, and d-peptides; oligomers having backbones which can adopt helical or sheet conformations, such as compounds having backbones utilizing bipyridine segments, compounds having backbones utilizing solvophobic interactions, compounds having backbones utilizing side chain interactions, compounds having backbones utilizing hydrogen bonding interactions, and compounds having backbones utilizing metal coordination. All of the amino acids in the human body, except glycine, exist as the D and L forms. Nearly all of the amino acids occurring in nature are the L-forms. D-forms of the amino acids are not found in the proteins of higher organisms, but are present in some lower forms of life, such as in the cell walls of bacteria. They also are found in some antibiotics, among them, streptomycin, actinomycin, bacitracin, and tetracycline. These antibiotics can kill bacterial cells by interfering with the formation of proteins necessary for viability and reproduction. Non-naturally occurring amino acids also include residues, which have side chains that resist non-specific protein adsorption, which may be designed to enhance the presentation of the antimicrobial peptide in biological fluids, and/or polymerizable side chains, which enable the synthesis of polymer brushes using the non-natural amino acid residues within the peptides as monomeric units.

Polymer: unless otherwise indicated, "polymer" includes natural and synthetic, homopolymers and copolymers comprising multiple repeat units and, unless otherwise indicated, may be linear, branched, or dendritic. Examples of copolymers include, but are not limited to, random copolymers and block copolymers, smart polymers, temperature responsive (e.g., NIPAM), and pH responsive (e.g., pyridyl based) polymers.

Polypeptide/Peptide/Oligopeptide: unless otherwise indicated, "polypeptide," "peptide," and "oligopeptide" encompass organic compounds composed of amino acids, whether natural, synthetic or mixtures thereof, that are linked together chemically by peptide bonds. Peptides typically contain 3 or more amino acids, preferably more than 9 and less than 150, more preferably less than 100, and most preferably between 9 and 51 amino acids. The polypeptides can be "exogenous," or "heterologous," i.e., production of peptides within an organism or cell that are not native to that organism or cell, such as human polypeptide produced by a bacterial cell. Exogenous also refers to substances that are not native to the cells and are added to the cells, as compared to endogenous materials, which are produced by the cells. The peptide bond involves a single covalent link between the carboxyl group (oxygen-bearing carbon) of one amino acid and the amino nitrogen of a second amino acid. Small peptides with fewer than about ten constituent amino acids are typically called oligopeptides, and peptides with more than ten amino acids are termed polypeptides. Compounds with molecular weights of more than 10,000 Daltons (50-100 amino acids) are usually termed proteins.

Quaternary Nitrogen: unless otherwise indicated, "quaternary nitrogen," as used herein, refers to a nitrogen atom that is a member of a quaternary ammonium cation.

$R_{rms}$ Surface Roughness: unless otherwise indicated, "$R_{rms}$ Surface Roughness" refers to root mean squared roughness of a surface, which measures the vertical deviations of a real surface from its ideal form. The roughness refers to surface micro-roughness which may be different than measurements of large scale surface variations. Preferably, this may be measured using atomic force microscopy (MFP-3D, Aslyum) across a field of approximately 1-30 μm by 1-30 μm, preferably 20 μm by 20 μm. The sample is washed with purified water to remove surface salts and then air dried. Standard silicon cantilever (Olympus AC160TS, spring constant 42 N/m) is employed for the measurement with an AC/Tapping mode. The $R_{rms}$ surface roughness is calculated by the software (IGOR Pro) attached with the AFM machine. Alternatively the roughness can be measured using a stylus profilometer. For example, the sample surface roughness can be measured by a Tencor P-16+ profilometer with a 60 degree, 2 μm diamond tip stylus. Preferably, an 800 μm scan length is chosen with 20 μm/second scan rate, 50 Hz scan frequency, and 2 μg loading force. At least three different sites are measured for the same sample, and the surface roughness is averaged from at least three samples. Alternatively, the $R_{rms}$ surface roughness can be measured preferably by non-contact methods, including using optical profilometers. For example, the sample surface roughness is measured by a optical profilometer (Zeta Z20 or Olympus Lext OLS4000). Preferably a 3-D image is taken by the optical profilometer under a 50× objective lens, and the sample's surface roughness is then measured along at least three different lines cross the image. At least three different spots are measured and the surface roughness is averaged from at least three samples. In a preferred example an Olympus LEXT OLS4000 3D Laser Measuring Microscope is employed for roughness measurements and 3D imaging. A LEXT microscope utilizes low wavelength optical technology with a 408 nm laser in combination with confocal scanning can be used for the measurement. Samples to be measured are mounted on a glass slide by double-sided tape. Digital 3-D images are taken with the Olympus LEXT OLS4000 laser confocal microscope ("LEXT") under an Olympus MPLAPON 50× objective lens. The digital images taken in this way have a 256×256 μm field area. The Z-direction repeatability for this LEXT machine has been certified by Olympus to be less than 0.012 μm. To measure the roughness, at least three images have been taken from each sample and the $R_{rms}$ roughness is calculated by using a 9 μm cut-off length.

Solvent Extractable Polymerization Initiator: unless otherwise indicated, "Solvent Extractable Polymerization Initiator" refers to any compound capable of starting radical polymerization that has been incorporated within the article, wherein either the initiator or its degradation products may be extracted from the article using a suitable solvent. In general, extractions can use nonpolar or polar solvents. For example, extraction solvents such as water, acetone or ethanol; and/or other extraction solvents in which the solubility of the initiator and/or its degradation products is at least 1 mg/L. The extraction should be carried out for a sufficient time such that the change in concentration of the extract is not increasing more than 5% per hour. Alternatively, extraction until the amount of extracted material in a subsequent extraction is less than 10% of that detected in the initial extraction, or until there is no analytically significant increase in the cumulative extracted material levels detected.

Extraction conditions include: 37° C. for 72 h; 50° C. for 72 h; 70° C. for 24 h; 121° C. for 1 h. Extraction ratio includes 6 cm$^2$/mL surface area/volume and/or 0.2 g sample/mL. In some instances, complete dissolution of the substrate may be appropriate. Materials shall be cut into small pieces before extraction to enhance submersion in the extract media, for example, for polymeric substrates approximately 10 mm×50 mm or 5 mm×25 mm are appropriate. The instrumentation used includes high-performance liquid chromatography-photo-diode array detection-mass spectrometry (HPLC-PDA-MS) for organics analysis; gas chromatography-mass spectrometry (GC-MS) for organics analysis; inductively coupled plasma-optical emission spectroscopy or mass spectrometry (ICP-OES or ICP-MS) for metals analysis; and sometimes ion chromatography (IC) for inorganics and ion analysis. Sometimes more advanced MS detectors such as time-of-flight (TOF) are used to obtain accurate mass information. Hexane and alcohol extractions are analyzed by GC-MS. Water and alcohol extractions are analyzed by HPLC. The initiator or its degradation products may be quantified and/or detected in the substrate or grafted polymer by the previously described methods. These include FTIR-ATR, electron spectroscopy for chemical analysis (ESCA, also called X-ray photoelectron spectroscopy, XPS), Secondary Ion Mass Spectrometry (SIMS), and surface-enhanced Raman spectroscopy (SERS). For example, peroxide may be detected spectrophotometrically using any of the following three methods: the iodide method (oxidation of sodium iodide by peroxides in the presence of ferric chloride), the DPPH method (treatment with 1,1-diphenyl-2-picrylhydrazyl, a radical scavenger, to decompose the peroxides), or the peroxidase method (reduction with glutathione, catalyzed by glutathione peroxidase, followed by measuring the coupled oxidation of NADPH in the presence of glutathione reductase). See, for example, Fujimoto et al., Journal of Polymer Science Part A: Polymer Chemistry, Vol. 31, 1035-1043 (1993).

Stable: unless otherwise indicated, "stable," as used herein in reference to a material, means that the material retains functionality over extended periods of time. In one embodiment, the referenced material retains at least 90% of a referenced activity (or property) for at least 30 days at 37° C. in at least one of phosphate buffered saline containing protein, media, or serum, or in vivo. In one embodiment, the reference material retains at least 80% of a referenced activity (or property) for at least 90 days at 37° C. in at least one of phosphate buffered saline containing protein, media, or serum, or in vivo. In one embodiment, the referenced material retains at least 90% of the referenced activity (or property) for at least 30 days at 37° C. and at least 80% of the referenced activity (or property) for at least 90 days at 37° C. The referenced activity or property may include surface contact angle, non-fouling, anti-thrombogenic, and/or antimicrobial activity.

Static Contact Angle: unless otherwise indicated, "Static Contact Angle" is the angle at which a water/vapor interface meets a substrate surface at or near equilibrium conditions. The contact angle is measured by first soaking the samples with pure ethanol for 5 minutes and washing with PBS three times. The samples are then soaked within PBS (150 mM, pH 7.4) for 24 hours and washed three times with purified water. Then the samples are dried under a flow of air for 5 min before testing. A drop of purified water (e.g., 1 µL) is deposited on the test surface, the shape of the droplet is photographed by a microscope with a CCD camera using a video contact angle system (e.g., VCA 2000, AST Inc.), and the contact angle is then determined (using, for example, a VCA Optima XE). The size of the water droplet used to determine the contact angle may vary depending upon the substrate type and composition. For a 5 French device, for instance, an 0.1 µL drop of purified water may be used.

Substantially Hemocompatible: unless otherwise indicated, "substantially hemocompatible" means that the composition is substantially non-hemolytic, in addition to being non-thrombogenic and non-immunogenic, as tested by appropriately selected assays for thrombosis, coagulation, and complement activation as described in ISO 10993-4.

Substantially Non-Cytotoxic: unless otherwise indicated, "substantially non-cytotoxic" refers to a composition that does not substantially change the metabolism, proliferation, or viability of mammalian cells that contact the surface of the composition. These may be quantified by the International Standard ISO 10993-5 which defines three main tests to assess the cytotoxicity of materials including the extract test, the direct contact test and the indirect contact test.

Substantially Non-Hemolytic Surface: unless otherwise indicated, "substantially non-hemolytic surface" means that the composition does not lyse 50%, preferably 20%, more preferably 10%, even more preferably 5%, most preferably 1')/0, of human red blood cells when the following assay is applied: a stock of 10% washed pooled red blood cells (Rockland Immunochemicals Inc, Gilbertsville, Pa.) is diluted to 0.25% with a hemolysis buffer of 150 mM NaCl and 10 mM Tris at pH 7.0. A 0.5 cm$^2$ antimicrobial sample is incubated with 0.75 mL of 0.25% red blood cell suspension for 1 hour at 37° C. The solid sample is removed and cells are spun down at 6000 g, the supernatant is removed, and the OD414 measured on a spectrophotometer. Total hemolysis is defined by diluting 10% of washed pooled red blood cells to 0.25% in sterile deionized (DI) water and incubating for 1 hour at 37° C., and 0% hemolysis is defined using a suspension of 0.25% red blood cells in hemolysis buffer without a solid sample.

Substantially Non-Toxic: unless otherwise indicated, "substantially non-toxic" means a surface that is substantially hemocompatible and substantially non-cytotoxic.

Substituted/Optionally Substituted: unless otherwise indicated, the term "substituted" and "optionally substituted" means that the referenced group is or may be substituted with one or more additional suitable group(s), which may be individually and independently selected, for example, from acetals, acyl, acyloxy, alkenoxy, alkoxy, alkylthio, alkynoxy, amido, amino, aryl, aryloxy, arylthio, azido, carbonyl, carboxamido, carboxyl, cyano, esters, ethers, hydrocarbyl, substituted hydrocarbyl, heterohydrocarbyl, substituted heterohydroalkyl, cycloalkyl, halogen, heteroalicyclic, heteroaryl, hydroxy, isocyanato, isothiocyanato, ketals, keto, mercapto, nitro, perhaloalkyl, silyl, sulfamoyl, sulfate, sulfhydryl, sulfonamido, sulfonate, sulfonyl, sulfoxido, thiocarbonyl, thiocyanato, thiol, and/or the protected derivatives thereof. It will be understood that "substitution" or "substituted" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

Substrate: unless otherwise indicated, "substrate" refers to the material from which a non-fouling polymer is grafted.

Sulfoammonium: unless otherwise indicated, a "sulfoammonium" moiety is a zwitterionic moiety comprising sulfate and ammonium functionality and includes, for example, sulfoammonium monomers, sulfoammonium oligomers, sulfoammonium polymers, sulfoammonium repeat units, and other sulfoammonium-containing materials. Sulfobetaine monomers, oligomers, polymers, repeat units, and other sulfobetaine materials are exemplary sulfoammonium moieties.

Tether/Tethering Agent/Linker: unless otherwise indicated, "tether" or "tethering agent" or "linker," as used herein synonymously, refers to any molecule, or set of molecules, or polymer used to covalently or non-covalently immobilize one or more non-fouling materials, one or more bioactive agents, or combinations thereof on a material where the molecule remains as part of the final chemical composition. The tether can be either linear or branched with one or more sites for immobilizing bioactive agents. The tether can be any length. However, in one embodiment, the tether is greater than 3 angstroms in length. The tether may be non-fouling, such as a monomer, oligomer, or polymer or a non-fouling non-zwitterionic material. The tether may be immobilized directly on the substrate or on a polymer, either of which may be non-fouling.

Undercoating Layer: unless otherwise indicated, "undercoating layer" refers to any coating, or combination of coatings, incorporated into a substrate from which a non-fouling polymer is grafted.

Zwitterion/Zwitterionic Material: unless otherwise indicated, "zwitterion" or "zwitterionic material" refers to a macromolecule, material, or moiety possessing both cationic and anionic groups. In most cases, these charged groups are balanced, resulting in a material with zero net charge.

Zwitterionic Polymers: unless otherwise indicated, "zwitterionic polymers" may be homopolymers or copolymers and include both polyampholytes (e.g., polymers with the charged groups on different monomer units) and polybetaine (polymers with the anionic and cationic groups on the same monomer unit). Exemplary zwitterionic polymers include alternating copolymers, statistical copolymers, random copolymers and block copolymers of two, three or more monomers.

DETAILED DESCRIPTION OF THE INVENTION

Among the various aspects of the present invention may be noted the provision of articles, such as medical devices, having a non-fouling grafted polymer layer. In general, therefore, the article comprises a substrate and a polymeric material grafted from the substrate. Surprisingly, it has been found that non-fouling grafted polymer layers can be provided by incorporating one or more polymerization initiator(s) into the substrate, for example, by imbibing the substrate with the initiator(s) or depositing a layer onto the substrate that comprises the initiator(s), and grafting a polymer from the substrate. In a particularly preferred embodiment, the polymeric material is grafted from the substrate in a polymerization mixture comprising monomer and a solvent system wherein the substrate is not significantly swelled by the solvent system and the incorporated initiator has limited solubility in the solvent system. Stated differently, the initiator(s) incorporated into the substrate have reversed phase properties compared to the solvent system especially in terms of hydrophilicity. Without being bound to any particular theory, it is believed that this method provides a relatively high local concentration of initiator(s) at or near the substrate surface/polymerization mixture interface, and favors grafting from the substrate and the grafted polymer to form a branched polymer.

Regardless of the theory, the grafted polymers of the present invention comprise a relatively dense, branched and hydrophilic structure that uniformly covers substrate surface defects and enhances performance. As a result, articles having a surface modified by the grafted polymers possess improved anti-fouling, and/or antithrombotic characteristics and, in certain embodiments, improved antimicrobial characteristics.

Generally speaking, small initiator molecules can be concentrated at or near the substrate surface, where polymerization is initiated and propagated, more readily than larger polymer molecules synthesized in solution. As a result, and as compared to graft-to coatings, greater surface densities can be achieved which, in turn, tends to improve non-fouling performance. Additionally, longer polymer chains and/or branched non-fouling chains may further improve performance.

Medical devices and other articles comprise any of a wide range of materials. Certain of these materials, by virtue of their intrinsic characteristics, exhibit a greater resistance to protein adsorption and cell/microorganism adhesion; for example, hydrophilic materials tend to exhibit less protein adsorption than hydrophobic materials. In addition, methods of manufacture can greatly affect the surface characteristics of such materials; for example, manufacturing methods may affect the porosity of a material, its roughness (microroughness and macro-roughness), incorporation of foreign-body inclusions that project from the surface of the material, and similar surface characteristics. Each of these, and other factors, may contribute to a material's resistance (or lack thereof) to protein adsorption and/or cell/microorganism adhesion.

Without being bound to any particular theory, it is presently believed that the graft-from polymerization methods of the present invention provide a surface modification, that is, a non-fouling polymer layer, having a branched structure which disfavors protein adsorption and/or cell/microorganism adhesion and which may, in addition, conceal or otherwise alter the sites in a substrate that favor the adhesion of cells, bacteria or other microorganisms. Thus, for example, and relative to the (unmodified) surface of the article, the grafted polymer layer may cover or even, partially or completely fill, scratches, pinholes, voids or other defects in the surface of the article that could potentially otherwise serve as a site for a performance failure. By way of further example, grafted polymer layers having a thickness that is at least as great as the surface roughness of the (unmodified) surface of the article, that are relatively uniform, that are sufficiently dense, and/or are significantly hydrophilic can significantly increase a material's resistance to protein adsorption and/or cell/microorganism adhesion.

In one aspect of the present invention, a non-fouling layer is applied onto only a portion or portions of a substrate or object, including in a 2 or 3-dimensional pattern or patterns at discrete locations on a substrate or object. In some embodiments the non-fouling layer is applied onto a substrate or object in such a way as to have discrete and/or blended geometrical features and/or designs at many scales ranging from nanometers to micrometers to millimeters. Preferred embodiments include controllably forming a discrete non-fouling feature(s) involves the selective masking or blocking of the desired portions of the substrate from imbibing and/or application of the initiator and/or from the graft polymerization. In one embodiment a portion of the substrate article is masked during initiator application. In one preferred embodiment a portion of the substrate article is masked during polymerization. The masking technique may be applied to any of the substrates described herein, including metals, ceramics, glasses, polymers, biological tissues, living or dead, woven and non-woven fibers, semimetals such as silicon.

Among the various aspects of the present invention is controllably placing a non-fouling polymer at discrete locations on a substrate or object by several means. For locations, patterns, geometric features/designs greater than or equal to millimeter scale controllably placing a non-fouling polymer may be accomplished by physically masking areas where the non-fouling polymer will not form, for example, by using techniques such as applying tape, screens, resists, or other blocking materials that inhibit access of the polymerization solution to the substrate or object surface, therefore inhibiting polymer formation. For locations, patterns, geometric features/designs less than millimeter scale controllably placing a non-fouling polymer may be accomplished by physically masking areas where the non-fouling polymer will not form using techniques such as photolithographic procedures (such as stereolithography, laser-chemical three-dimensional writing, and modular assembly), microcontact printing, or microstamping of blocking materials that inhibit access of the polymerization solution to the substrate or object surface, therefore inhibiting polymer formation. In addition, masking materials can be applied at any scale by means of digital application methods such as spray jet, valve jet, and inkjet printing methods.

In some embodiments, masking during polymerization permits the ability to apply a mix of different polymers over different areas of a substrate or object. By means of selectively removing portions or types of masking materials or agents from discrete locations followed by subsequent polymerization steps with different monomers or monomer mixtures a non-fouling surface can be constructed consisting of any number of different polymers with similar or different non-fouling, dimensional, mechanical, physical, and/or chemical properties.

One embodiment includes techniques that remove initiator imbibed portions and/or non-fouling polymer portions from the substrate or object in a controlled fashion and thus create locations, patterns, geometric features/designs of non-fouling polymer at any scale, including laser ablation, abrasive media stream/spray, or direct contact physical abrasion/scraping.

The presence or absence of a non-fouling polymer in a controlled design/pattern can be used to control and/or modulate the interaction, adsorption, desorption, of proteins and other biomolecules as well as control and/or modulate, interaction, adsorption, desorption, proliferation of cells (eukaryotes, prokaryotes). Structures which may influence these processes including creating columns perpendicular to the article surface, channels along the surface, or a number of other geometrical patterns. The feature size or space between features may be smaller, approximately the same size as, or larger than the protein or cell being influenced. Structures that reduce adsorption may be synergistic with non-fouling polymer surface modifications to enhance non-fouling ability.

Independent of any theory, articles of the present invention having a modified surface comprising a grafted polymer exhibit low fibrinogen adsorption in a fibrinogen adsorption assay. In general, the modified surface exhibits a fibrinogen adsorption of less than 125 ng/cm$^2$ in a fibrinogen adsorption assay in which samples are incubated for 60 minutes at 37° C. in 70 μg/mL fibrinogen derived from human plasma, and the amount of adsorbed fibrinogen is determined using a standard protocol, preferably by using radiolabeled fibrinogen. In one embodiment, the modified surface exhibits a fibrinogen adsorption of less than 90 ng/cm$^2$ in a fibrinogen adsorption assay in which samples are incubated for 60 minutes at 37° C. in 70 μg/mL fibrinogen derived from human plasma, and the amount of adsorbed fibrinogen is determined using a standard protocol, preferably by using radiolabeled fibrinogen. In one embodiment, the modified surface exhibits a fibrinogen adsorption of less than 70 ng/cm$^2$ in a fibrinogen adsorption assay in which samples are incubated for 60 minutes at 37° C. in 70 μg/mL fibrinogen derived from human plasma, and the amount of adsorbed fibrinogen is determined using a standard protocol, preferably by using radiolabeled fibrinogen. In one embodiment, the modified surface exhibits a fibrinogen adsorption of less than 50 ng/cm$^2$ in a fibrinogen adsorption assay in which samples are incubated for 60 minutes at 37° C. in 70 μg/mL fibrinogen derived from human plasma, and the amount of adsorbed fibrinogen is determined using a standard protocol, preferably by using radiolabeled fibrinogen. Preferably, the modified surface exhibits a fibrinogen adsorption of less than 30 ng/cm$^2$ in such an assay. More preferably, in certain embodiments the modified surface exhibits a fibrinogen adsorption of less than 20 ng/cm$^2$ in such an assay. Still more preferably, in certain embodiments the modified surface exhibits a fibrinogen adsorption of less than 15 ng/cm$^2$ in such an assay. In some embodiments, the modified surface exhibits a fibrinogen adsorption of less than 12 ng/cm$^2$ in such an assay. In some embodiments, the modified surface exhibits a fibrinogen adsorption of less than 10 ng/cm$^2$ in such an assay. In some embodiments, the modified surface exhibits a fibrinogen adsorption of less than 8 ng/cm$^2$ in such an assay. In some embodiments, the modified surface exhibits a fibrinogen adsorption of less than 6 ng/cm$^2$ in such an assay. In some embodiments, the modified surface exhibits a fibrinogen adsorption of less than 4 ng/cm$^2$ in such an assay. In some embodiments, the modified surface exhibits a fibrinogen adsorption of less than 2 ng/cm$^2$ in such an assay. In some embodiments, the modified surface exhibits a fibrinogen adsorption of less than 1 ng/cm$^2$ in such an assay. In some embodiments, the modified surface exhibits a fibrinogen adsorption of less than 0.5 ng/cm$^2$ in such an assay. In some embodiments, the modified surface exhibits a fibrinogen adsorption of less than 0.25 ng/cm$^2$ in such an assay. In one embodiment, the grafted polymer in each of the foregoing examples recited in this paragraph is a zwitterionic polymer. In one embodiment, the grafted polymer in each of the foregoing examples and embodiments recited in this paragraph is a polymer containing carboxyammonium or sulfoammonium repeat units. In one embodiment, the grafted polymer in each of the foregoing examples and embodiments recited in this paragraph is a polymer containing sulfobetaine or carboxybetaine repeat units. In one embodiment, the grafted polymer in each of the foregoing examples and embodiments recited in this paragraph is a zwitterionic polymer and the zwitterionic polymer is grafted from a polyurethane polymer. In one embodiment, the grafted polymer in each of the foregoing examples and embodiments recited in this paragraph is a carboxyammonium or sulfoammonium polymer and the carboxyammonium or sulfoammonium polymer is grafted from a polyurethane polymer. In one embodiment, the grafted polymer in each of the foregoing examples and embodiments recited in this paragraph is a polymer containing sulfobetaine or carboxybetaine repeat units and the polymer containing sulfobetaine or carboxybetaine repeat units is grafted from a polyurethane polymer.

Preferred embodiments also show reduction in thrombus for substrates having a grafted polymer layer of the present invention. For example, thrombus reduction of modified substrates, i.e., substrates having a grafted polymer layer can be assessed relative to a reference substrate, i.e., the same or an otherwise functionally equivalent substrate lacking the grafted polymer layer, by exposing them to freshly harvested bovine blood, heparinized, with radiolabeled platelets, in a flow loop for 2 hours. As an assessment of anti-thrombogenic performance, samples are placed in an ex-vivo flow loop model of thrombosis. Anti-thrombogenic activity can be evaluated using ex-vivo flow loop model of thrombosis. Briefly, up to 10 liters of fresh blood are collected from a single animal (bovine). This blood is heparinized to prevent coagulation, filtered to remove particulates, and autologous radio-labeled platelets are added. Within eight hours after blood harvesting, coated and uncoated articles are placed in a flow loop circuit, which pumps blood from a bath over the article and then back into the bath. A second internal flow loop circuit can be established for substrate containing a lumen by connecting the two ports of the substrate through a 2nd peristaltic pump. The size of tubing into which the article is placed and speed of the blood flow may be adjusted based on the size of the article being tested. Preferably, when the articles are 14-15.5 French dialysis catheters, they are placed in a flow loop circuit with tubing diameter of approximately 12.5-25.4 mm inner diameter. Blood is pumped in the outer circuit at a rate of approximately 2.5 L/min, while blood in the inner circuit is pumped at a rate of approximately ~200-400 ml/min. When the articles are 5 French PICC catheter shafts, they are placed in a flow loop circuit of approximately 6.4 mm inner diameter and blood flow rate is approximately 200 mL/min. The lumens may be locked with a solution, for example saline, during evaluation. Alternatively, the distal tip may be sealed, for example with epoxy, during evaluation. When the articles are 10 French rods, they are placed in a flow loop circuit of approximately 6.4 mm inner diameter and blood flow rate is approximately 200 ml/min. After 60-120 minutes, the articles are removed, inspected visually for thrombus formation, and adhered platelets are quantified using a Gamma counter. For samples not containing a lumen, only an outer circuit may be used to measure thrombus on the outside of the device. In this assay, preferred embodiments show at least an 80% reduction relative to reference substrate in adsorbed platelets and substantial visual reduction of thrombus. For example, in certain embodiments there is at least a 90% reduction in adsorbed platelets for modified substrates relative to reference substrates. Preferred embodiments show at least a 98% reduction in adsorbed platelets for modified substrates relative to reference substrates. Alternatively, in a preferred embodiment, the thrombogenecity of a modified substrate is reduced relative to the non-modified substrate, after exposure to a 47% (w/v) sodium citrate solution in DI water for greater than 3 days. Embodiments show a visual reduction of thrombus relative to for modified substrates relative to reference substrates. Preferred embodiments show at least an 80% reduction of a modified substrate relative to a reference substrate in adsorbed platelets and substantial visual reduction of thrombus. Preferred embodiments show at least a 90% reduction in adsorbed platelets for modified substrates relative to reference substrates. Preferred embodiments show at least a 98% reduction in adsorbed platelets for modified substrates relative to reference substrates. Alternatively, the thrombogenecity of preferred embodiments are reduced relative to the non-modified substrate after exposure to animal serum and/or plasma. For example, the thrombogenecity of preferred embodiments are reduced after 55 day exposure to citrated human plasma at 37° C. for modified substrates relative to reference substrates. Embodiments show a visual reduction of thrombus for modified substrates relative to reference substrates. Preferred embodiments show at least an 80% reduction for modified substrates relative to reference substrates in adsorbed platelets and substantial visual reduction of thrombus. Preferred embodiments show at least a 90% reduction in adsorbed platelets for modified substrates relative to reference substrates. Preferred embodiments show at least a 98% reduction in adsorbed platelets for modified substrates relative to reference substrates.

Preferred embodiments show antibiofilm activity for modified substrates of at least 0.5 log, 1 log, 1.5 log, 2 log, 2.5 log, 3 log, or 4 log. More preferred embodiments have antibiofilm activity after extended exposures to PBS, serum, or plasma products. In one preferred embodiment, antibiofilm activity of 1 log is achieved after 30 days storage in PBS at 37° C. In a further preferred embodiment, antibiofilm activity of 1 log is achieved after 90 days storage in PBS at 37° C. In one preferred embodiment, antibiofilm activity of 2 log is achieved after 30 days storage in PBS at 37° C. In a further preferred embodiment, antibiofilm activity of 2 log is achieved after 90 days storage in PBS at 37° C. In one preferred embodiment, antibiofilm activity of 1 log is achieved after 30 days storage in citrated human plasma at 37° C. In a further preferred embodiment, antibiofilm activity of 1 log is achieved after 90 days storage in citrated human plasma at 37° C. In one preferred embodiment, antibiofilm activity of 2 log is achieved after 30 days storage in citrated human plasma at 37° C. In a further preferred embodiment, antibiofilm activity of 2 log is achieved after 90 days storage in citrated human plasma at 37° C.

Preferred embodiments show resistance to protein adsorption after extended exposure to PBS, which may indicate hydrolytic stability. In some embodiments, the modified surface exhibits a fibrinogen adsorption of less than 125 ng/cm$^2$ in a fibrinogen adsorption assay in which samples are incubated for 60 minutes at 37° C. in 70 μg/mL fibrinogen derived from human plasma after 30 days exposure to PBS at 37° C. In some embodiments, the modified surface exhibits a fibrinogen adsorption of less than 90 ng/cm$^2$ in a fibrinogen adsorption assay in which samples are incubated for 60 minutes at 37° C. in 70 μg/mL fibrinogen derived from human plasma after 30 days exposure to PBS at 37° C. In some embodiments, the modified surface exhibits a fibrinogen adsorption of less than 70 ng/cm$^2$ in a fibrinogen adsorption assay in which samples are incubated for 60 minutes at 37° C. in 70 μg/mL fibrinogen derived from human plasma after 30 days exposure to PBS at 37° C. In some embodiments, the modified surface exhibits a fibrinogen adsorption of less than 50 ng/cm$^2$ in a fibrinogen adsorption assay in which samples are incubated for 60 minutes at 37° C. in 70 μg/mL fibrinogen derived from human plasma after 30 days exposure to PBS at 37° C. In some embodiments, the modified surface exhibits a fibrinogen adsorption of less than 30 ng/cm$^2$ in a fibrinogen adsorption assay in which samples are incubated for 60 minutes at 37° C. in 70 μg/mL fibrinogen derived from human plasma after 30 days exposure to PBS at 37° C. In some embodiments, the modified surface exhibits a fibrinogen adsorption of less than 20 ng/cm$^2$ in a fibrinogen adsorption assay in which samples are incubated for 60 minutes at 37° C. in 70 μg/mL fibrinogen derived from human plasma after 30 days exposure to PBS at 37° C. In some embodiments, the modified surface exhibits a fibrinogen adsorption of less than 15 ng/cm$^2$ in a fibrinogen adsorption assay in which samples are incubated for 60 minutes at 37° C. in 70 µg/mL fibrinogen derived from human plasma after 30 days exposure to PBS at 37° C. In some embodiments, the modified surface exhibits a fibrinogen adsorption of less than 12 ng/cm² in a fibrinogen adsorption assay in which samples are incubated for 60 minutes at 37° C. in 70 µg/mL fibrinogen derived from human plasma after 30 days exposure to PBS at 37° C. In some embodiments, the modified surface exhibits a fibrinogen adsorption of less than 10 ng/cm² in a fibrinogen adsorption assay in which samples are incubated for 60 minutes at 37° C. in 70 µg/mL fibrinogen derived from human plasma after 30 days exposure to PBS at 37° C. In some embodiments, the modified surface exhibits a fibrinogen adsorption of less than 8 ng/cm² in a fibrinogen adsorption assay in which samples are incubated for 60 minutes at 37° C. in 70 µg/mL fibrinogen derived from human plasma after 30 days exposure to PBS at 37° C. In some embodiments, the modified surface exhibits a fibrinogen adsorption of less than 6 ng/cm² in a fibrinogen adsorption assay in which samples are incubated for 60 minutes at 37° C. in 70 µg/mL fibrinogen derived from human plasma after 30 days exposure to PBS at 37° C. In some embodiments, the modified surface exhibits a fibrinogen adsorption of less than 4 ng/cm² in a fibrinogen adsorption assay in which samples are incubated for 60 minutes at 37° C. in 70 µg/mL fibrinogen derived from human plasma after 30 days exposure to PBS at 37° C. In some embodiments, the modified surface exhibits a fibrinogen adsorption of less than 2 ng/cm² in a fibrinogen adsorption assay in which samples are incubated for 60 minutes at 37° C. in 70 µg/mL fibrinogen derived from human plasma after 30 days exposure to PBS at 37° C. In some embodiments, the modified surface exhibits a fibrinogen adsorption of less than 1 ng/cm² in a fibrinogen adsorption assay in which samples are incubated for 60 minutes at 37° C. in 70 µg/mL fibrinogen derived from human plasma after 30 days exposure to PBS at 37° C. In some embodiments, the modified surface exhibits a fibrinogen adsorption of less than 0.5 ng/cm² in a fibrinogen adsorption assay in which samples are incubated for 60 minutes at 37° C. in 70 µg/mL fibrinogen derived from human plasma after 30 days exposure to PBS at 37° C. In some embodiments, the modified surface exhibits a fibrinogen adsorption of less than 0.25 ng/cm² in a fibrinogen adsorption assay in which samples are incubated for 60 minutes at 37° C. in 70 µg/mL fibrinogen derived from human plasma after 30 days exposure to PBS at 37° C.

Preferred embodiments show resistance to protein adsorption after extended exposure to PBS, which may indicate hydrolytic stability. In some embodiments, the modified surface exhibits a fibrinogen adsorption of less than 125 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface exhibits a fibrinogen adsorption of less than 90 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface exhibits a fibrinogen adsorption of less than 70 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface exhibits a fibrinogen adsorption of less than 50 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface exhibits a fibrinogen adsorption of less than 30 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface exhibits a fibrinogen adsorption of less than 20 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface exhibits a fibrinogen adsorption of less than 15 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface exhibits a fibrinogen adsorption of less than 12 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface exhibits a fibrinogen adsorption of less than 10 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface exhibits a fibrinogen adsorption of less than 8 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface exhibits a fibrinogen adsorption of less than 6 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface exhibits a fibrinogen adsorption of less than 4 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface exhibits a fibrinogen adsorption of less than 2 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface exhibits a fibrinogen adsorption of less than 1 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface exhibits a fibrinogen adsorption of less than 0.5 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface exhibits a fibrinogen adsorption of less than 0.25 ng/cm² in a fibrinogen adsorption assay in which samples are incubated for 60 minutes at 37° C. in 70 µg/mL fibrinogen derived from human plasma after 90 days exposure to PBS at 37° C.

In general, the surface of the substrate may be modified with any of a range of non-fouling polymeric materials. For example, the non-fouling polymeric material may be a homopolymer or a copolymer. If a copolymer, the non-fouling polymeric material may be an alternating copolymer (e.g., [AB . . . ]$_n$, a periodic copolymer (e.g., [A$_n$B$_m$ . . . ] wherein n and m are different), a statistical copolymer (a copolymer in which monomers are arranged according to a known statistical rule), a random copolymer, or a block copolymer in which each of the blocks is independently a homopolymer or an alternating, periodic, statistical or random copolymer. Furthermore, when the non-fouling polymeric material is a copolymer it may be diblock, a triblock or other polyblock copolymer. For example, in one preferred embodiment, the non-fouling polymeric material comprises a homopolymer. In an alternative preferred embodiment, the non-fouling polymeric material comprises a random copolymer. In yet another embodiment, the non-fouling polymeric material comprises a block copolymer, e.g., a diblock or triblock copolymer.

In one embodiment the surface modification, i.e., the grafted polymer, has a thickness which is at least equal to the surface roughness of the substrate surface. For example, if the surface of a substrate has a global average $R_{rms}$ surface roughness of 100 nm, it is preferred in this embodiment that the grafted polymer layer have a global average dry thickness of at least 100 nm. In some embodiments, the substrate surface is relatively smooth, e.g., a global average $R_{rms}$ surface roughness of 2 nm. In other embodiments, the substrate surface is significantly rougher, e.g., a global average $R_{rms}$ surface roughness of 1 µm. In other embodiments, the substrate surface will have a surface roughness intermediate of these values, e.g., a global average $R_{rms}$ surface roughness of 75-250 nm. In each of these embodiments, it is preferred that the thickness of the grafted polymer layer exceed the global average $R_{rms}$ surface roughness of the substrate surface. Thus, for example, in one embodiment the global average dry thickness of the grafted polymer layer is at least 110% of the global average $R_{rms}$ surface roughness of the substrate surface. By way of further example, the global average dry thickness may be at least 200% of the global average $R_{rms}$ surface roughness of the substrate surface. By way of yet further example, the global average dry thickness may be at least 500% of the global average $R_{rms}$ surface roughness of the substrate surface. By way of yet further example, the global average dry thickness may be at least 1,000% of the global average $R_{rms}$ surface roughness of the substrate surface. In a preferred embodiment, the global average dry thickness of the grafted polymer layer is determined using a scanning electron microscope (SEM) under vacuum and global average $R_{rms}$ surface roughness is determined using an atomic force microscope. In one embodiment, the grafted polymer layer in each of the foregoing embodiments and examples recited in this paragraph is a zwitterionic polymer. In one embodiment, the grafted polymer in each of the foregoing examples and embodiments recited in this paragraph is a polymer containing carboxyammonium or sulfoammonium repeat units. In one embodiment, the grafted polymer in each of the foregoing examples and embodiments recited in this paragraph is a polymer containing sulfobetaine or carboxybetaine repeat units. In one embodiment, the grafted polymer in each of the foregoing examples and embodiments recited in this paragraph is a zwitterionic polymer and the zwitterionic polymer is grafted from a polyurethane polymer. In one embodiment, the grafted polymer in each of the foregoing examples and embodiments recited in this paragraph is a carboxyammonium or sulfoammonium polymer and the carboxyammonium or sulfoammonium polymer is grafted from a polyurethane polymer. In one embodiment, the grafted polymer in each of the foregoing examples and embodiments recited in this paragraph is a polymer containing sulfobetaine or carboxybetaine repeat units and the polymer containing sulfobetaine or carboxybetaine repeat units is grafted from a polyurethane polymer.

In one embodiment, the grafted polymer layer preferentially at least partially fills in defects in the substrate surface. Without being bound by any particular theory, a depression or invagination in the substrate is surrounded by initiator containing substrate and therefore the amount of initiator available to drive polymerization within the depression or invagination may be more substantial than on a flat region of the substrate. This may accelerate the polymerization in and filling of these defects. In some embodiments, defects in the form of depressions having a depth of at least 100 nm as measured in a direction that is normal to the surrounding surface and a width as measured in a direction parallel to and at the surrounding surface that is at least 100 nm may be preferentially filled with a grafted polymer.

In one embodiment, the grafted polymer layer does not significantly increase the surface roughness. For example, in one embodiment, the modified surface, i.e., the surface of the article with the grafted polymer, has a surface roughness value that is less than 300% of the global average $R_{rms}$ surface roughness of the surface of the article without the grafted polymer layer. By way of further example, in one such embodiment, the global average $R_{rms}$ surface roughness of the modified surface is no more than 250% of the global average $R_{rms}$ surface roughness of the surface of the article without the grafted polymer layer. By way of further example, in one such embodiment, the global average $R_{rms}$ surface roughness of the modified surface is no more than 200% of the global average $R_{rms}$ surface roughness of the surface of the article without the grafted polymer layer. By way of further example, in one such embodiment, the global average $R_{rms}$ surface roughness of the modified surface is no more than 150% of the global average $R_{rms}$ surface roughness of the surface of the article without the grafted polymer layer. By way of further example, in one such embodiment, the global average $R_{rms}$ surface roughness of the modified surface is no more than the global average $R_{rms}$ surface roughness of the surface of the article without the grafted polymer layer.

In one embodiment, and particularly for articles having substrate surfaces with relatively large surface roughness values, the grafted polymer layer may reduce the surface roughness; stated differently, the modified surface, i.e., the surface of the article with the grafted polymer, has less surface roughness than the surface of the substrate. For example, in one such embodiment the global average $R_{rms}$ surface roughness of the modified surface is at least 50% less than the global average $R_{rms}$ surface roughness of the surface of the article without the grafted polymer layer. By way of further example, in one such embodiment the global average $R_{rms}$ surface roughness of the modified surface is at least 25% less than the global average $R_{rms}$ surface roughness of the surface of the article without the grafted polymer layer. By way of further example, in one such embodiment the global average $R_{rms}$ surface roughness of the modified surface is at least 10% less than the global average $R_{rms}$ surface roughness of the surface of the article without the grafted polymer layer. By way of further example, in one such embodiment global average $R_{rms}$ surface roughness of the modified surface is at least 5% less than the global average $R_{rms}$ surface roughness of the surface of the article without the grafted polymer layer.

Independent of the relative surface roughness, the modified surface preferably has a relatively low surface roughness value. For example, the modified surface preferably has a global average $R_{rms}$ surface roughness of less than 500 nm.

By way of further example, the modified surface may have a global average $R_{rms}$ surface roughness of less than 400 nm. By way of further example, the modified surface may have a global average $R_{rms}$ surface roughness of less than 300 nm. By way of further example, the modified surface may have a global average $R_{rms}$ surface roughness of less than 200 nm. By way of further example, the modified surface may have a global average $R_{rms}$ surface roughness of less than 150 nm. By way of further example, the modified surface may have a global average $R_{rms}$ surface roughness of less than 100 nm. By way of further example, the modified surface may have a global average $R_{rms}$ surface roughness of less than 75 nm. By way of further example, the modified surface may have a global average $R_{rms}$ surface roughness of less than 50 nm. By way of further example, the modified surface may have a global average $R_{rms}$ surface roughness of less than 25 nm. By way of further example, the modified surface may have a global average $R_{rms}$ surface roughness of less than 10 nm. By way of further example, the modified surface preferably has a global average $R_{rms}$ surface roughness of less than 5 nm. By way of further example, the modified surface preferably has a global average $R_{rms}$ surface roughness of less than 2 nm. By way of further example, the modified surface preferably has a global average $R_{rms}$ surface roughness of less than 1 nm. In one embodiment, the grafted polymer layer in each of the foregoing embodiments and examples recited in this paragraph is a zwitterionic polymer. In one embodiment, the grafted polymer in each of the foregoing examples and embodiments recited in this paragraph is a polymer containing carboxyammonium or sulfoammonium repeat units. In one embodiment, the grafted polymer in each of the foregoing examples and embodiments recited in this paragraph is a polymer containing sulfobetaine or carboxybetaine repeat units. In one embodiment, the grafted polymer in each of the foregoing examples and embodiments recited in this paragraph is a zwitterionic polymer and the zwitterionic polymer is grafted from a polyurethane polymer. In one embodiment, the grafted polymer in each of the foregoing examples and embodiments recited in this paragraph is a carboxyammonium or sulfoammonium polymer and the carboxyammonium or sulfoammonium polymer is grafted from a polyurethane polymer. In one embodiment, the grafted polymer in each of the foregoing examples and embodiments recited in this paragraph is a polymer containing sulfobetaine or carboxybetaine repeat units and the polymer containing sulfobetaine or carboxybetaine repeat units is grafted from a polyurethane polymer.

In one embodiment, the grafted polymer layer may reduce the number of visual protrusions having a size greater than 0.1 micrometers relative to a reference substrate, that is, the same or an otherwise functionally equivalent substrate lacking the non-fouling polymer layer. For example, the number of such visual protrusions may be reduced by at least 25%. By way of further example, the number of such visual protrusions may be reduced by at least 50%. By way of further example, the number of such visual protrusions may be reduced by at least 75%. By way of further example, the number of such visual protrusions may be reduced by at least 90%. In one embodiment, the grafted polymer layer may reduce the number of visual protrusions having a size greater than 0.5 micrometers relative to a reference substrate, that is, the same or an otherwise functionally equivalent substrate lacking the non-fouling polymer layer. For example, the number of such visual protrusions may be reduced by at least 25%. By way of further example, the number of such visual protrusions may be reduced by at least 50%. By way of further example, the number of such visual protrusions may be reduced by at least 75%. By way of further example, the number of such visual protrusions may be reduced by at least 90.

Depending upon the article to which the surface modification is being applied and its working environment, the grafted polymer layer may have any of a wide range of thicknesses. For some applications, for example, the non-fouling grafted polymer layer will have a global average dry thickness of at least about 50 nm. For some applications, substantially thicker grafted polymer layers may be desirable. For example, the non-fouling grafted polymer layer may have a global average dry thickness of 50 micrometers. Typically, however, the non-fouling grafted polymer layer will have an average thickness that is less. For example, in some embodiments the non-fouling grafted polymer layer will have a global average dry thickness of up to 10 micrometers. By way of further example, in some embodiments the non-fouling grafted polymer layer will have a global average dry thickness of up to 1 micrometer. By way of further example, in some embodiments the non-fouling grafted polymer layer will have a global average dry thickness of up to 500 nm. By way of further example, in some embodiments the non-fouling grafted polymer layer will have a global average dry thickness in the range of about 100 nm to about 1,000 nm. By way of further example, in some embodiments the non-fouling grafted polymer layer will have a global average dry thickness in the range of about 300 nm to about 600 nm. By way of further example, in some embodiments the non-fouling grafted polymer layer will have a global average dry thickness in the range of about 200 nm to about 400 nm. In a preferred embodiment, the global average dry thickness of the grafted polymer layer is determined using a scanning electron microscope (SEM) under vacuum. In one embodiment, the grafted polymer in each of the foregoing examples and embodiments recited in this paragraph is a polymer containing carboxyammonium or sulfoammonium repeat units. In one embodiment, the grafted polymer in each of the foregoing examples and embodiments recited in this paragraph is a polymer containing sulfobetaine or carboxybetaine repeat units. In one embodiment, the grafted polymer in each of the foregoing examples and embodiments recited in this paragraph is a zwitterionic polymer and the zwitterionic polymer is grafted from a polyurethane polymer. In one embodiment, the grafted polymer in each of the foregoing examples and embodiments recited in this paragraph is a carboxyammonium or sulfoammonium polymer and the carboxyammonium or sulfoammonium polymer is grafted from a polyurethane polymer. In one embodiment, the grafted polymer in each of the foregoing examples and embodiments recited in this paragraph is a polymer containing sulfobetaine or carboxybetaine repeat units and the polymer containing sulfobetaine or carboxybetaine repeat units is grafted from a polyurethane polymer.

In general, the surface modification preferably has a relatively uniform thickness. For example, in one embodiment it is generally preferred that the standard deviation of the global average dry thickness of the non-fouling grafted polymer layer not exceed 100% of the global average dry thickness of the non-fouling grafted polymer layer. By way of further example, in one embodiment the standard deviation of the global average dry thickness of the non-fouling grafted polymer layer will not exceed 50% of the global average dry thickness of the non-fouling grafted polymer layer By way of further example, in one embodiment the standard deviation of the global average dry thickness of the non-fouling grafted polymer layer will not exceed 20% of the global average dry thickness of the non-fouling grafted polymer layer. By way of further example, in one embodiment the standard deviation of the global average dry thickness of the non-fouling grafted polymer layer will not exceed 10% of the global average dry thickness of the non-fouling grafted polymer layer. The standard deviation of the thickness is preferably determined by taking at least 5, and more preferably at least 6-10, randomly spaced measurements of the grafted polymer layer thickness. In one embodiment, the grafted polymer in each of the foregoing examples and embodiments recited in this paragraph is a polymer containing carboxyammonium or sulfoammonium repeat units. In one embodiment, the grafted polymer in each of the foregoing examples and embodiments recited in this paragraph is a polymer containing sulfobetaine or carboxybetaine repeat units. In one embodiment, the grafted polymer in each of the foregoing examples and embodiments recited in this paragraph is a zwitterionic polymer and the zwitterionic polymer is grafted from a polyurethane polymer. In one embodiment, the grafted polymer in each of the foregoing examples and embodiments recited in this paragraph is a carboxyammonium or sulfoammonium polymer and the carboxyammonium or sulfoammonium polymer is grafted from a polyurethane polymer. In one embodiment, the grafted polymer in each of the foregoing examples and embodiments recited in this paragraph is a polymer containing sulfobetaine or carboxybetaine repeat units and the polymer containing sulfobetaine or carboxybetaine repeat units is grafted from a polyurethane polymer.

In general, the surface modifications of the present invention are relatively hydrophilic. In general, the modified surface exhibits a static contact angle of less than 40 degrees. For example, modified surfaces of articles comprising non-fouling polymeric materials of the present invention grafted from a relatively hydrophobic polymer such as silicone, hydrocarbon rubbers, fluorosilicones, fluoropolymers and other polymers having a native contact angle of at least 90 degrees may exhibit a static contact angle of less than 40 degrees. By way of further example, modified surfaces of articles comprising non-fouling polymeric materials of the present invention grafted from a relatively hydrophobic substrate having a contact angle of at least 90 degrees may exhibit a static contact angle of less than 30 degrees. By way of further example, modified surfaces of articles comprising non-fouling polymeric materials of the present invention grafted from a relatively hydrophobic substrate having a contact angle of at least 90 degrees may exhibit a static contact angle of less than 25 degrees. By way of further example, modified surfaces of articles having non-fouling polymeric materials of the present invention grafted from a relatively hydrophobic substrate having a contact angle of at least 90 degrees may exhibit a static contact angle of less than 20 degrees. By way of further example, modified surfaces of articles having non-fouling polymeric materials of the present invention grafted from a relatively hydrophobic substrate having a contact angle of at least 90 degrees may exhibit a static contact angle of less than 15 degrees. In one embodiment, the grafted polymer in each of the foregoing examples and embodiments recited in this paragraph is a polymer containing carboxyammonium or sulfoammonium repeat units. In one embodiment, the grafted polymer in each of the foregoing examples and embodiments recited in this paragraph is a polymer containing sulfobetaine or carboxybetaine repeat units. In one embodiment, the grafted polymer in each of the foregoing examples and embodiments recited in this paragraph is a zwitterionic polymer and the zwitterionic polymer is grafted from a polyurethane polymer. In one embodiment, the grafted polymer in each of the foregoing examples and embodiments recited in this paragraph is a carboxyammonium or sulfoammonium polymer and the carboxyammonium or sulfoammonium polymer is grafted from a polyurethane polymer. In one embodiment, the grafted polymer in each of the foregoing examples and embodiments recited in this paragraph is a polymer containing sulfobetaine or carboxybetaine repeat units and the polymer containing sulfobetaine or carboxybetaine repeat units is grafted from a polyurethane polymer.

Articles having non-fouling polymeric materials of the present invention grafted from a less hydrophobic substrate such as polyurethane (including aliphatic polycarbonate-based polyurethanes) having a contact angle less than 90 degrees but greater than 25 degrees may exhibit a static contact angle of less than 25 degrees. For example, in one embodiment modified surfaces of articles having non-fouling polymeric materials of the present invention grafted from a substrate having a contact angle of at least 25 degrees exhibit a static contact angle of less than 24 degrees. By way of further example, in one embodiment modified surfaces of articles having non-fouling polymeric materials of the present invention grafted from a substrate having a contact angle of at least 25 degrees exhibit a static contact angle of less than 23 degrees. By way of further example, in one embodiment modified surfaces of articles having non-fouling polymeric materials of the present invention grafted from a substrate having a contact angle of at least 25 degrees exhibit a static contact angle of less than 22 degrees. By way of further example, in one embodiment modified surfaces of articles having non-fouling polymeric materials of the present invention grafted from a substrate having a contact angle of at least 25 degrees exhibit a static contact angle of less than 21 degrees. By way of further example, in one embodiment modified surfaces of articles having non-fouling polymeric materials of the present invention grafted from a substrate having a contact angle of at least 25 degrees exhibit a static contact angle of less than 20 degrees. By way of further example, in one embodiment modified surfaces of articles having non-fouling polymeric materials of the present invention grafted from a substrate having a contact angle of at least 25 degrees exhibit a static contact angle of less than 19 degrees. By way of further example, in one embodiment modified surfaces of articles having non-fouling polymeric materials of the present invention grafted from a substrate having a contact angle of at least 25 degrees exhibit a static contact angle of less than 18 degrees. By way of further example, in one embodiment modified surfaces of articles having non-fouling polymeric materials of the present invention grafted from a substrate having a contact angle of at least 25 degrees exhibit a static contact angle of less than 17 degrees. By way of further example, in one embodiment modified surfaces of articles having non-fouling polymeric materials of the present invention grafted from a substrate having a contact angle of at least 25 degrees exhibit a static contact angle of less than 16 degrees. By way of further example, in one embodiment modified surfaces of articles having non-fouling polymeric materials of the present invention grafted from a substrate having a contact angle of at least 25 degrees exhibit a static contact angle of less than 15 degrees. By way of further example, in one embodiment modified surfaces of articles having non-fouling polymeric materials of the present invention grafted from a substrate having a contact angle of at least 25 degrees exhibit a static contact angle of about 5 to about 15 degrees. In one embodiment, the non-fouling polymeric material in each of the foregoing embodiments and examples recited in this paragraph is a zwitterionic polymer. In one embodiment, the grafted polymer in each of the foregoing examples and embodiments recited in this paragraph is a polymer containing carboxyammonium or sulfoammonium repeat units. In one embodiment, the grafted polymer in each of the foregoing examples and embodiments recited in this paragraph is a polymer containing sulfobetaine or carboxybetaine repeat units. In one embodiment, the grafted polymer in each of the foregoing examples and embodiments recited in this paragraph is a zwitterionic polymer and the zwitterionic polymer is grafted from a polyurethane polymer. In one embodiment, the grafted polymer in each of the foregoing examples and embodiments recited in this paragraph is a carboxyammonium or sulfoammonium polymer and the carboxyammonium or sulfoammonium polymer is grafted from a polyurethane polymer. In one embodiment, the grafted polymer in each of the foregoing examples and embodiments recited in this paragraph is a polymer containing sulfobetaine or carboxybetaine repeat units and the polymer containing sulfobetaine or carboxybetaine repeat units is grafted from a polyurethane polymer.

In addition to being relatively hydrophilic, the grafted polymer layers of the present invention may also have a limited swelling capacity. For example, in one embodiment the difference between the dry thickness of the grafted polymer layer and the thickness of the grafted polymer layer under ambient conditions is not great. For example, the magnitude of the difference between the global average dry thickness of the grafted polymer layer as determined by standard scanning electron microscopy (SEM) to the global average humidified thickness of the grafted polymer layer as determined by environmental scanning electron microscopy (ESEM) is less than 200% of the global average dry thickness. For some applications, even less swelling capacity may be desirable. For example, the difference in thickness of the grafted polymer layer under such conditions may be less than 100% of the global average dry thickness. By way of further example, the difference in thickness of the grafted polymer layer as determined by SEM and ESEM under such conditions may be less than 50% of the global average dry thickness. By way of further example, the difference in thickness of the grafted polymer layer as determined by SEM and ESEM under such conditions may be less than 25% of the global average dry thickness. By way of further example, the difference in thickness of the grafted polymer layer as determined by SEM and ESEM under such conditions may be less than 10% of the global average dry thickness. By way of further example, the difference in thickness of the grafted polymer layer as determined by SEM and ESEM under such conditions may be less than 5% of the global average dry thickness. By way of further example, the difference in thickness of the grafted polymer layer as determined by SEM and ESEM under such conditions may be less than 1% of the global average dry thickness. By way of further example, no difference may be observable by such a comparison. In one embodiment, the grafted polymer layer in each of the foregoing embodiments and examples recited in this paragraph is a zwitterionic polymer. In one embodiment, the grafted polymer in each of the foregoing examples and embodiments recited in this paragraph is a polymer containing carboxyammonium or sulfoammonium repeat units. In one embodiment, the grafted polymer in each of the foregoing examples and embodiments recited in this paragraph is a polymer containing sulfobetaine or carboxybetaine repeat units. In one embodiment, the grafted polymer in each of the foregoing examples and embodiments recited in this paragraph is a zwitterionic polymer and the zwitterionic polymer is grafted from a polyurethane polymer. In one embodiment, the grafted polymer in each of the foregoing examples and embodiments recited in this paragraph is a carboxyammonium or sulfoammonium polymer and the carboxyammonium or sulfoammonium polymer is grafted from a polyurethane polymer. In one embodiment, the grafted polymer in each of the foregoing examples and embodiments recited in this paragraph is a polymer containing sulfobetaine or carboxybetaine repeat units and the polymer containing sulfobetaine or carboxybetaine repeat units is grafted from a polyurethane polymer.

Advantageously, the process of the present invention may be tuned to provide independent control of the thickness, the thickness uniformity, the degree of hydrophilicity (contact angle), and/or the swelling capacity of the grafted polymer layer, as well as the surface roughness of the surface-modified article. Thus, for example, the process may be controlled to provide an article having a grafted polymer layer with a global average dry thickness that is at least 110% of the global average $R_{rms}$ surface roughness of the substrate, a standard deviation for the thickness of the non-fouling grafted polymer layer that does not exceed 100% of the global average dry thickness of the non-fouling grafted polymer layer, and a magnitude of the difference between the global average dry thickness of the grafted polymer layer as determined by standard scanning electron microscopy (SEM) and the global average humidified thickness of the grafted polymer layer as determined by environmental scanning electron microscopy (ESEM) that is less than 200% of the global average dry thickness. By way of further example, the process may be controlled to provide an article having a grafted polymer layer with a global average dry thickness that is at least 200% of the global average $R_{rms}$ surface roughness of the substrate, a standard deviation for the thickness of the non-fouling grafted polymer layer that does not exceed 50% of the global average dry thickness of the non-fouling grafted polymer layer, and a magnitude of the difference between the global average dry thickness of the grafted polymer layer as determined by standard scanning electron microscopy (SEM) and the global average humidified thickness of the grafted polymer layer as determined by environmental scanning electron microscopy (ESEM) that is less than 200% of the global average dry thickness. By way of further example, the process may be controlled to provide an article having a grafted polymer layer with a global average dry thickness that is at least 200% of the global average $R_{rms}$ surface roughness of the substrate, a standard deviation for the thickness of the non-fouling grafted polymer layer that does not exceed 50% of the global average dry thickness of the non-fouling grafted polymer layer, and a magnitude of the difference between the global average dry thickness of the grafted polymer layer as determined by standard scanning electron microscopy (SEM) and the global average humidified thickness of the grafted polymer layer as determined by environmental scanning electron microscopy (ESEM) that is less than 100% of the global average dry thickness. By way of further example, the process may be controlled to provide an article having a grafted polymer layer with a global average dry thickness that is at least 200% of the global average $R_{rms}$ surface roughness of the substrate, a standard deviation for the thickness of the non-fouling grafted polymer layer that does not exceed 50% of the global average dry thickness of the non-fouling grafted polymer layer, and a magnitude of the difference between the global average dry thickness of the grafted polymer layer as determined by standard scanning electron microscopy (SEM) and the global average humidified thickness of the grafted polymer layer as determined by environmental scanning electron microscopy (ESEM) that is less than 50% of the global average dry thickness. By way of further example, the process may be controlled to provide an article having a grafted polymer layer with a global average dry thickness that is at least 200% of the global average $R_{rms}$ surface roughness of the substrate, a standard deviation for the thickness of the non-fouling grafted polymer layer that does not exceed 50% of the global average dry thickness of the non-fouling grafted polymer layer, and a magnitude of the difference between the global average dry thickness of the grafted polymer layer as determined by standard scanning electron microscopy (SEM) and the global average humidified thickness of the grafted polymer layer as determined by environmental scanning electron microscopy (ESEM) that is less than 25% of the global average dry thickness. By way of further example, the process may be controlled to provide an article having a grafted polymer layer with a global average dry thickness that is at least 200% of the global average $R_{rms}$ surface roughness of the substrate, a standard deviation for the thickness of the non-fouling grafted polymer layer that does not exceed 20% of the global average dry thickness of the non-fouling grafted polymer layer, and a magnitude of the difference between the global average dry thickness of the grafted polymer layer as determined by standard scanning electron microscopy (SEM) and the global average humidified thickness of the grafted polymer layer as determined by environmental scanning electron microscopy (ESEM) that is less than 25% of the global average dry thickness. By way of further example, the process may be controlled to provide an article having a grafted polymer layer with a global average dry thickness that is at least 200% of the global average $R_{rms}$ surface roughness of the substrate, a standard deviation for the thickness of the non-fouling grafted polymer layer that does not exceed 10% of the global average dry thickness of the non-fouling grafted polymer layer, and a magnitude of the difference between the global average dry thickness of the grafted polymer layer as determined by standard scanning electron microscopy (SEM) and the global average humidified thickness of the grafted polymer layer as determined by environmental scanning electron microscopy (ESEM) that is less than 25% of the global average dry thickness. By way of further example, the process may be controlled to provide an article exhibiting a static contact angle of less than 25 degrees and a grafted polymer layer with a global average dry thickness that is at least 110% of the global average $R_{rms}$ surface roughness of the substrate, a standard deviation for the thickness of the non-fouling grafted polymer layer that does not exceed 100% of the global average dry thickness of the non-fouling grafted polymer layer, and a magnitude of the difference between the global average dry thickness of the grafted polymer layer as determined by standard scanning electron microscopy (SEM) and the global average humidified thickness of the grafted polymer layer as determined by environmental scanning electron microscopy (ESEM) that is less than 200% of the global average dry thickness. By way of further example, the process may be controlled to provide an article exhibiting a static contact angle of less than 25 degrees and a grafted polymer layer with a global average dry thickness that is at least 200% of the global average $R_{rms}$ surface roughness of the substrate, a standard deviation for the thickness of the non-fouling grafted polymer layer that does not exceed 50% of the global average dry thickness of the non-fouling grafted polymer layer, and a magnitude of the difference between the global average dry thickness of the grafted polymer layer as determined by standard scanning electron microscopy (SEM) and the global average humidified thickness of the grafted polymer layer as determined by environmental scanning electron microscopy (ESEM) that is less than 100% of the global average dry thickness. By way of further example, the process may be controlled to provide an article exhibiting a static contact angle of less than 25 degrees and a grafted polymer layer with a global average dry thickness that is at least 200% of the global average $R_{rms}$ surface roughness of the substrate, a standard deviation for the thickness of the non-fouling grafted polymer layer that does not exceed 50% of the global average dry thickness of the non-fouling grafted polymer layer, and a magnitude of the difference between the global average dry thickness of the grafted polymer layer as determined by standard scanning electron microscopy (SEM) and the global average humidified thickness of the grafted polymer layer as determined by environmental scanning electron microscopy (ESEM) that is less than 50% of the global average dry thickness. By way of further example, the process may be controlled to provide an article exhibiting a static contact angle of less than 25 degrees and a grafted polymer layer with a global average dry thickness that is at least 200% of the global average $R_{rms}$ surface roughness of the substrate, a standard deviation for the thickness of the non-fouling grafted polymer layer that does not exceed 50% of the global average dry thickness of the non-fouling grafted polymer layer, and a magnitude of the difference between the global average dry thickness of the grafted polymer layer as determined by standard scanning electron microscopy (SEM) and the global average humidified thickness of the grafted polymer layer as determined by environmental scanning electron microscopy (ESEM) that is less than 25% of the global average dry thickness. By way of further example, the process may be controlled to provide an article exhibiting a static contact angle of less than 25 degrees and a grafted polymer layer with a global average dry thickness that is at least 200% of the global average $R_{rms}$ surface roughness of the substrate, a standard deviation for the thickness of the non-fouling grafted polymer layer that does not exceed 50% of the global average dry thickness of the non-fouling grafted polymer layer, and a magnitude of the difference between the global average dry thickness of the grafted polymer layer as determined by standard scanning electron microscopy (SEM) and the global average humidified thickness of the grafted polymer layer as determined by environmental scanning electron microscopy (ESEM) that is less than 10% of the global average dry thickness. By way of further example, the process may be controlled to provide an article exhibiting a static contact angle of less than 25 degrees and a grafted polymer layer with a global average dry thickness that is at least 200% of the global average $R_{rms}$ surface roughness of the substrate, a standard deviation for the thickness of the non-fouling grafted polymer layer that does not exceed 50% of the global average dry thickness of the non-fouling grafted polymer layer, and a magnitude of the difference between the global average dry thickness of the grafted polymer layer as determined by standard scanning electron microscopy (SEM) and the global average humidified thickness of the grafted polymer layer as determined by environmental scanning electron microscopy (ESEM) that is less than 10% of the global average dry thickness. By way of further example, the process may be controlled to provide an article exhibiting a static contact angle of less than 25 degrees and a grafted polymer layer with a global average dry thickness that is at least 200% of the global average $R_{rms}$ surface roughness of the substrate, a standard deviation for the thickness of the non-fouling grafted polymer layer that does not exceed 50% of the global average dry thickness of the non-fouling grafted polymer layer, and a magnitude of the difference between the global average dry thickness of the grafted polymer layer as determined by standard scanning electron microscopy (SEM) and the global average humidified thickness of the grafted polymer layer as determined by environmental scanning electron microscopy (ESEM) that is less than 5% of the global average dry thickness. By way of further example, the process may be controlled to provide an article exhibiting a static contact angle of less than 25 degrees and a grafted polymer layer with a global average dry thickness that is at least 200% of the global average $R_{rms}$ surface roughness of the substrate, a standard deviation for the thickness of the non-fouling grafted polymer layer that does not exceed 50% of the global average dry thickness of the non-fouling grafted polymer layer, and a magnitude of the difference between the global average dry thickness of the grafted polymer layer as determined by standard scanning electron microscopy (SEM) and the global average humidified thickness of the grafted polymer layer as determined by environmental scanning electron microscopy (ESEM) that is less than 5% of the global average dry thickness. By way of further example, in each of the foregoing examples, the grafted polymer layer may have a global average dry thickness in the range of 100 nm to 1,000 nm.

In general, grafted polymeric material may be detected in a near-surface zone of the substrate using EDS mapping, XPS, or TOF-SIMS. The sample may be freeze fractured in liquid nitrogen to expose the coating/substrate interface. Fractured surface may then be coated with a thin layer of Au/Pt and observed under a scanning electron microscope with Energy Dispersive X-ray Analyser (EDAX) for element analysis. Suitable instruments include a FEI/Philips XL30 FEG ESEM. In order to assess if the polymeric material extends into the near-surface zone, at least 25, and preferably at least 50, representative locations spaced approximately evenly across the portion of the article carrying the grafted polymer layer should be analyzed to identify a detectable enhancement of polymeric material in the near-surface zone. For example, if a grafted polymer layer is applied to the indwelling portion of a catheter, the representative locations are approximately evenly spaced across the indwelling portion of the catheter. It is preferred to measure the thickness at representative points across the longest dimension of the portion of the article that is covered with the grafted polymer layer.

As described in greater detail elsewhere herein, incorporation of initiator into the substrate enables polymeric material to be grafted from surface and from within near-surface zone of the substrate. In general, however, it is preferred that polymeric material not extend too far into the substrate; thus, in one embodiment polymeric material is present in the near-surface zone but not at greater depths, i.e., not in the bulk. The maximum depth to which near-surface zone extends is, at least in part, a function of the initiator and the technique used to incorporate initiator in the substrate. Typically, however, it is generally preferred that lower boundary of the near-surface zone not be greater than 20 micrometers from the substrate surface as measured in a direction normal to the surface. By way of example, the lower boundary may not be greater than 15 micrometers from the substrate surface as measured in a direction normal to the surface. By way of further example, the lower boundary may not be greater than 10 micrometers from the substrate surface as measured in a direction normal to the surface. Similarly, the minimum depth of near-surface zone, i.e., the distance of the upper boundary from the substrate surface is, at least in part, also a function of the initiator and the technique used to incorporate initiator in the substrate. Typically, however, the upper boundary will be at least 0.1 micrometers from the substrate surface as measured in a direction normal to the surface. By way of example, the upper boundary may be at least 0.2 micrometers from the substrate surface as measured in a direction normal to the surface. By way of further example, the upper boundary may be at least 0.3 micrometers from the substrate surface as measured in a direction normal to the surface.

Substrates

In general, the substrate comprises any of a wide range of materials selected, for example, from one or more metals, ceramics, glasses, polymers, biological tissues, living or dead, woven and non-woven fibers, semi-metals such as silicon, and combinations thereof. In one embodiment, the substrate is a composite of two or more materials. For example, the substrate may comprise a polymeric coating, also sometimes referred to herein as an "undercoating," or a "precoating" over a metallic, ceramic, glass, polymeric, woven or non-woven fiber or semi-metal core. Alternatively, the substrate may comprise a polymeric material throughout, i.e., from its surface and into its bulk. By way of further example, the substrate may comprise a polymeric coating, overlying a metallic, ceramic, glass, polymeric, woven or non-woven fiber or semi-metal core inner layer which, in turn, overlies a metallic, ceramic, glass, polymeric, woven or non-woven fiber or semi-metal core.

As described in greater detail elsewhere herein, in a preferred embodiment of the polymerization method of the present invention, at least one polymerization initiator is incorporated into the substrate. As such, it is preferred that the near-surface zone of the substrate comprise a material, such as a polymer, having a sufficient capacity for the initiator(s). Thus, for example, when the substrate comprises a metal, ceramic, glass or other material having insufficient capacity for initiator(s), the substrate is provided with an undercoat or a precoat having sufficient capacity for the polymerization initiator(s).

In one embodiment, the substrate may be a composite of two or more materials, e.g., an underlying material such as a metal, ceramic, glass, semi-metal, polymer or other material with a polymeric or other material coating thereon (e.g., an undercoating or a precoating as described elsewhere herein). In such instances, the near-surface zone may lie partially within the underlying material and partially within the polymeric or other material coating thereon.

Suitable metallic materials include, but are not limited to, metals and alloys based on titanium, such as unalloyed titanium (ASTM F67) and titanium alloys, such as ASTM F1108, Ti-6Al-4V ELI (ASTM F136), Nitinol (ASTM F2063), nickel titanium alloys, and thermo-memory alloy materials; stainless steel (ASTM F138 and F139), tantalum (ASTM F560), palladium, zirconium, niobium, molybdenum, nickel-chrome, or certain cobalt alloys including Stellite, cobalt-chromium (Vitallium, ASTM F75 and Wrought cobalt-chromium (ASTM F90)), and cobalt-chromium-nickel alloys such as ELGILOY®, PHYNOX® and HASTELLOY®.

Suitable ceramic materials include, but are not limited to, oxides, carbides, or nitrides of the transition elements such as titanium oxides, hafnium oxides, iridium oxides, chromium oxides, aluminum oxides, and zirconium oxides. Silicon based materials, such as silica, may also be used.

Suitable polymeric materials include, but are not limited to, polyimide, polyamine, polyanhydride, polyazine, poly (carbonate), polyester, polyether, polyetheretherketone (PEEK), polyguanidine, polyimide, polyketal, poly(ketone), polyolefin, poly(orthoester), polyphosphazine, polysaccharide, polysiloxane, polysulfone, polyurea, polyurethane, halogenated polymer, silicone, aldehyde crosslinked resin, epoxy resin, phenolic resin, latex, or a copolymer or blend thereof. Exemplary polymers include polystyrene and substituted polystyrenes, polyalkylenes, such as polyethylene and polypropylene, poly(urethane)s, polyacrylates and polymethacrylates, polyacrylamides and polymethacrylamides, polyesters, polysiloxanes, polyethers (including polyacetals), poly(orthoesters), poly(carbonates), poly(hydroxyalkanoate)s, polyfluorocarbons, PEEK, Teflon, silicones, epoxy resins, KEVLAR®, NOMEX®, DACRON®, HYTREL®, PEBAX®, SURLYN®, nylon, polyalkenes, phenolic resins, PTFE, natural and synthetic elastomers, adhesives and sealants, polyolefins, polysulfones, polyacrylonitrile, biopolymers such as polysaccharides and natural latex copolymers thereof, and combinations thereof. In one embodiment the substrate is a medical grade polyurethane such as CARBOTHANE®, aliphatic polycarbonate-based polyurethanes, available from Lubrizol Corporation, blended with appropriate extrusion agents and plasticizers, possibly one already approved by the FDA or other appropriate regulatory agency for use in vivo. Preferred substrates include elastollan, pearlthane, desmopan, estane, pellethane, irogan, exelast EC, laripur, carbothane, CARBOTHANE®, isoplast, tecoflex, tecophilic, tecoplast, tecothane, biomer (Ethicon), biospan, cardiothane 51 (avothane), cardiomat, chronoflex AL, chronoflex AR, chronoflex C, corplex, corethane, mitrathane, rimplast, toyobo TMS, vialon, enka PUR, comfeel ulcus, viasorb, bioclusive, blisterfilm, opsite, tegaderm, epigard, lyofoam, omiderm, microthane, and surethane.

The substrate may optionally contain a radiopaque additive, such as barium sulfate, bismuth salts, gold foil, or tantalum to aid in radiographic imaging.

The substrate may be in the form of, or form part of, gels, liquids, films, particles (nanoparticles, microparticles, or millimeter diameter beads), fibers (wound dressings, bandages, gauze, tape, pads, sponges, including woven and non-woven sponges and those designed specifically for dental or ophthalmic surgeries), blood storage bags, surgical, medical or dental instruments, blood oxygenators, ventilators, pumps, drug delivery devices, tubing, wiring, electrodes, contraceptive devices, feminine hygiene products, endoscopes, grafts (including small diameter <6 mm), stents (including coronary, ureteral, renal, biliary, colorectal, esophageal, pulmonary, urethral, vascular, peripheral, neurovascular), stent grafts (including abdominal, thoracic, neurovascular and peripheral vascular), pacemakers, implantable cardioverter-defibrillators, cardiac resynchronization therapy devices, cardiovascular device leads, ventricular assist devices and drivelines, heart valves, vena cava filters, endovascular coils, catheters (including central venous, peripheral central, midline, peripheral, tunneled, dialysis access, urinary, neurological, peritoneal, intra-aortic balloon pump, angioplasty balloon, diagnostic, interventional, drug delivery, etc.), catheter connectors and valves (including needleless connectors), intravenous delivery lines and manifolds, shunts (including cardiac, cerebral, lumbar-peritoneal, pulmonary, portosystemic, portacaval, etc.), wound drains (internal or external including ventricular, ventriculoperitoneal, and lumboperitoneal), dialysis membranes, protein separation membranes, infusion ports, cochlear implants, endotracheal tubes, tracheostomy tubes, ventilator breathing tubes and circuits, guide wires, fluid collection bags, drug delivery bags and tubing, implantable sensors (e.g., intravascular, transdermal, intracranial, glucose sensors), diagnostic devices (e.g., microfluidic, microelectromechanical, and optical), ophthalmic devices including contact lenses, intraocular lenses and phacoemulsification devices, orthopedic devices (including hip implants, knee implants, shoulder implants, spinal implants (including cervical plates systems, pedicle screw systems, interbody fusion devices, artificial disks, and other motion preservation devices), screws, plates, rivets, rods, intramedullary nails, bone cements, artificial tendons, and other prosthetics or fracture repair devices), dental implants, periodontal implants, breast implants, penile implants, maxillofacial implants, cosmetic implants, valves, appliances, scaffolding, suturing material, needles, hernia repair meshes, tension-free vaginal tape and vaginal slings, prosthetic neurological devices, tissue regeneration or cell culture devices, dialyzer, cranial implants, syringes, blood collection containers, scrotal implants, calve implants, buttock implants, extraocular implants, horn implants, subdermal implants, transdermal implants, magnetic implants, medical devices containing microfluidics, blood based sensors used outside of the body, nanoparticles used as sensors, IV catheter sheath, or other medical devices used within or in contact with the body or any portion of any of these.

The substrate may be in the form of, or form part of, gels, foams, liquids, films, coatings, particles (nanoparticles, microparticles, or millimeter diameter beads), fibers (including woven and non-woven sponges and fabrics), marine and underwater coatings (including coatings for ships, submarines, marine and hydrokinetic devices, aquariums, underwater infrastructures, sewage pipes, and aqueduct tubes), packaging materials (including packaging for foods, beverages, cosmetics, and consumer products), desalination and water treatment systems (including condensers, spacers, pipelines, and membranes), separation membranes (including membranes for macrofiltration, microfiltration, ultrafiltration, nanofiltration, and reversed osmosis filtration), lab appliances and consumer products including containers (e.g., petri dishes, cell culture dishes, flasks, beakers), valves, needles, tapes, sealants, pipes, and tubes, earrings, body rings, contact lenses, cookware, gears (external/internal, spur, helical, double helical, bevel, hypoid, crown, worm, non-circular, etc.), turbomachinary (turbines and compressors), pumps (direct lift, displacement, velocity, buoyancy, and gravity), propellers, blades, knives, windshields, and glassware.

In one embodiment, the substrate is a vascularly inserted catheter such as a peripherally inserted central catheter (PICC), central venous catheter (CVC), or hemodialysis catheter, venous valves, punctual plugs, and intra-ocular devices and implants. In another embodiment, the substrate is a vascularly inserted catheter formed from a medical grade polyurethane or CARBOTHANE® or formed from a material coated with a medical grade polyurethane or CARBOTHANE®. In another embodiment, the substrate is a vascularly inserted catheter formed from a medical grade polyurethane or CARBOTHANE® containing a radiopaque additive, such as barium sulfate or bismuth salts to aid in radiographic imaging, or formed from a material coated with a medical grade polyurethane or CARBOTHANE® containing a radiopaque additive, such as barium sulfate or bismuth salts to aid in radiographic imaging.

In another embodiment, the substrate is a vascularly inserted catheter formed from a medical grade polyurethane such as Tecothane® or formed from a material coated with a medical grade polyurethane such as Tecothane®. In another embodiment, the substrate is a vascularly inserted catheter formed from a medical grade polyurethane such as Tecothane® containing a radiopaque additive, such as barium sulfate or bismuth salts to aid in radiographic imaging, or formed from a material coated with a medical grade polyurethane such as Tecothane® containing a radiopaque additive, such as barium sulfate or bismuth salts, to aid in radiographic imaging. In another embodiment, the substrate is a vascularly inserted catheter formed from a medical grade polyurethane such as Pellethane® or formed from a material coated with a medical grade polyurethane such as Pellethane®. In another embodiment, the substrate is a vascularly inserted catheter formed from a medical grade polyurethane such as Pellethane® containing a radiopaque additive, such as barium sulfate or bismuth salts, to aid in radiographic imaging, or formed from a material coated with a medical grade polyurethane such as Pellethane® containing a radiopaque additive, such as barium sulfate or bismuth salts, to aid in radiographic imaging.

Medical device substrates are often composed of multiple different materials, each with its own surface properties. Even devices composed primarily of a single polymer may be made up of material blends and can include plasticizers, radio-opacity agents, and other additives all of which will affect substrate surface properties. To insure uniform surface composition for maximizing coating adhesion and efficacy, a precoat of a single polymer or polymer blend may be placed over the substrate. In a particular embodiment, the undercoating coat contains a single polymer.

A polymer precoat or undercoat can be deposited on the substrate using a variety of techniques known in the art, such as solvent casting, dip-coating, spray-coating, plasma polymerization, roller coating, electrostatic coating, or brush coating. For example, the polymer to be applied as a precoat or undercoat is dissolved in a solvent in which the substrate is substantially insoluble and the substrate is dipped therein to deposit a layer of about 100 nm to about 500 micrometers of the precoat or undercoat polymer. Optionally, the deposited polymer is crosslinked as it is being applied or after it has been applied to the substrate. Use of a single polymer undercoating layer, for example, can result in the formation of a coating surface that has a uniform identity and concentration of functional groups.

In one preferred embodiment, a substrate is precoated with a polymer that conceals substrate defects. The precoat thickness can be less than or greater than the amount of global average $R_{rms}$ surface roughness of the substrate. In one preferred embodiment, the substrate has a precoat having an average thickness that exceeds the global average $R_{rms}$ surface roughness of the uncoated substrate. As described elsewhere herein, the precoating may optionally contain an initiator or at least one member of an initiator pair.

In one embodiment, the surface of the substrate is treated to improve the adherence of the precoat. For example, the substrate may be subjected to an oxidation pretreatment to increase the adhesion properties to the polymeric precoat; polymeric precoats may contain reactive groups that react with substrates forming a covalent bond. By way of further example, prior to receiving a precoat, the substrate may be silanized using small molecule or polymeric reagents to increase the adhesion properties to the polymeric precoat. By way of further example, the surface may be subjected to alternating organic and aqueous treatments.

The undercoating layer may contain a radiopaque agent, such as $BaSO_4$ or bismuth, to aid in radiographic imaging of the substrate. In one embodiment the polymer is a polyurethane polymer such as Tecoflex-93A or Carbothane 85A, optionally containing 0 to 40% by weight $BaSO_4$.

The undercoating layer can also include, but is not limited to, polymers such as polystyrene and substituted polystyrenes, polyethylene, polypropylene, poly(urethane)s, polyacrylates and polymethacrylates, polyacrylamides and polymethacrylamides, polyesters, polysiloxanes, polyethers, poly(orthoester), poly(carbonates), poly(hydroxyalkanoate)s, polyfluorocarbons, PEEK, Teflon, silicones, epoxy resins, KEVLAR®, NOMEX®, DACRON®, HYTREL®, PEBAX®, SURLYN®, nylon, polyalkenes, phenolic resins, PTFE, natural and synthetic elastomers, adhesives and sealants, polyolefins, polysulfones, polyacrylonitrile, biopolymers such as polysaccharides and natural latex copolymers thereof, and combinations thereof.

The precoated substrate can then be further functionalized using the coating methods described below.

In the case where a greater density of non-fouling material is desired, the creation of microstructure on the substrate surface can create more area for grafting non-fouling materials from the surface, without increasing the apparent surface area of the article. For polymeric substrates, including hydrogel networks, this surface morphology can be created through appropriate polymer structural design. One example of this methodology is the growth of surface tethered dendrimeric polymers. Each generation of the dendrimer effectively doubles the number of zwitterionic sites presenting. Other polymer architectures include brush polymers, such as brush copolymers, comb polymers, such as comb copolymers, linear and branched copolymers, crosslinked polymers, hydrogels, polymer blends, and combinations thereof.

Surface Modifications

In general, a non-fouling polymeric material is grafted from a substrate into which one or more polymerization initiators have been incorporated. In one embodiment, the non-fouling polymeric material is grafted from a substrate that is a composite of two or more materials, e.g., an underlying material such as a metal, ceramic, glass, semimetal, polymer or other material with a polymeric or other material coating thereon (e.g., an undercoating or a precoating as previously described herein). For example, in one embodiment, the non-fouling polymeric material is grafted from a polymeric undercoat layer, such as a polyurethane layer which overlies a metal or ceramic bulk. By way of further example, in one embodiment the non-fouling polymeric material is grafted from a polymeric undercoat layer, such as a polyurethane layer which overlies a polymeric bulk, such as polyurethane.

Preferably, the non-fouling polymeric material that is grafted from the substrate comprises a chain-growth polymer (that is, a polymer or polymer block formed by addition polymerization), or a combination thereof. The chain-growth polymer may be, for example, an addition polymer derived from monomer(s) incorporating double or triple bonds, e.g., an olefin. By way of further example, the chain-growth polymer may comprise an addition polymer derived from a cyclic monomer by means of a ring-opening polymerization reaction. Thus, the polymer may be a chain-growth homopolymer or copolymer. In a preferred embodiment, the polymer is a chain growth addition homopolymer or a chain growth addition copolymer comprising the residue of two or more monomers.

In accordance with one aspect of the present invention, it is generally preferred that the non-fouling polymeric material be prepared without inordinate use of a polyfunctional crosslinking agent. For example, it is generally preferred that the non-fouling polymeric material contain less than 50 mole % of the residue of a polyvalent crosslinker. In one such embodiment, the non-fouling polymeric material contains less than 25 mole % of the residue of a polyvalent crosslinker. In one such embodiment, non-fouling polymeric material contain less than 10 mole % of a polyvalent crosslinker. In one such embodiment, the non-fouling polymeric material contains less than 5 mole % of the residue of a polyvalent crosslinker. In one such embodiment, non-fouling polymeric material contain less than 3 mole % of a polyvalent crosslinker. In one such embodiment, the non-fouling polymeric material contains less than 0.1 mole % of the residue of a polyvalent crosslinker. In one such embodiment, the non-fouling polymeric material contains no residue of a polyvalent crosslinker.

Through grafting, step-growth or chain-growth techniques, the non-fouling polymeric material may comprise any of a range of polymer types or combinations thereof. The polymer backbone may be neutral (e.g., polyalkylene or polyether) or contain permanently charged moieties (e.g., cyclic or acyclic quaternized nitrogen atoms), or even zwitterionic backbones (e.g., phosphorylcholine backbones). In one embodiment, therefore, the non-fouling polymeric material comprises a polymer or copolymer selected from the group consisting of polyamide, polyamine, polyanhydride, polyazine, poly(carbonate), polyester, polyether, polyetheretherketone (PEEK), polyguanidine, polyimide, polyketal, poly(ketone), polyolefin, poly(orthoester), polyphosphazine, polysaccharide, polysiloxane, polysulfone, polyurea, polyurethane, halogenated polymer, silicone, hydrocarbon, ether-ester, ether-amide or ionized polyethylene and combinations thereof.

The polymer may also contain a wide range of pendant (side-chain) groups, hydrophilic and hydrophobic, neutral, anionic, cationic, or mixed charged. For example, the pendant groups may include neutral hydrophilic groups such as hydroxy, oligo(ethylene glycol) and/or poly(ethylene glycol) moieties, or it may include charged groups such as anionic moieties, cationic moieties, and zwitterionic moieties.

Zwitterionic Groups

Zwitterions are molecules that carry formal positive and negative charges on non-adjacent atoms within the same molecule and molecules that may be ionized by addition or removal of an electrophile or a nucleophile, or by removal of a protecting group. Both natural and synthetic polymers, containing zwitterion functionality, have been shown to resist protein adhesion. In one embodiment, the zwitterionic monomer contains a phosphorylcholine moiety, a carboxyammonium moiety, a sulfoammonium moiety, derivatives thereof, or combinations thereof. In one embodiment, the zwitterionic monomer contains a carboxyammonium moiety, a sulfoammonium moiety, derivatives thereof, or combinations thereof. In one embodiment, the zwitterionic monomer contains a sulfobetaine moiety or a carboxybetaine moiety. The zwitterionic polymer may be formed by initiating polymerization with radicals present in the polymeric substrate, in the presence of one or more monomers, such as sulfobetaine methacrylate or carboxybetaine methacrylate monomers.

Polysulfoammonium polymers such as polysulfobetaines, polycarboxyammonium polymers such as polycarboxybetaines and other natural and synthetic zwitterion chemistries can be used to design non-fouling materials for the biomedical applications described herein. Some examples of natural zwitterions chemistries that could be used for non-fouling materials include, but are not limited to, amino acids, peptides, natural small molecules including, but not limited to, N,N,N-trimethylglycine (glycine betaine), trimethylamine oxide (TMAO), dimethylsulfoniopropionate sarcosine, lysergic acid and psilocybin. Additional synthetic zwitterions that could be used to create non-fouling materials, include, but are not limited to, amino-carboxylic acids (carboxybetaines), amino-sulfonic acids (sulfo betaines), cocamidopropyl betaine, quinonoid based zwitterions, decaphenylferrocene, and non-natural amino acids. Natural and synthetic polymers also include mixed charged structures with both positive charged and negative charged moieties on the pendant groups, in the main chains, or at the terminal groups.

Materials containing, or composed of, these natural or synthetic zwitterions, can be grafted from surfaces, particularly the surfaces of medical devices, in order to improve biocompatibility, reduce thrombogenesis (such as on the surface of stents or venous valves), and reduce fouling by proteins or bacteria present in solution. This is particularly applicable for surfaces where non-specific binding of proteins in solution could negatively impact the desired or necessary mechanics of a device.

In one embodiment, the non-fouling polymer contains zwitterionic pendant groups covalently attached, directly or indirectly, to the polymer back bone. The zwitterionic pendant groups may have an overall net charge, for instance, by having a divalent center of anionic charge and monovalent center of cationic charge or vice versa, or by having two centers of cationic charge and one center of anionic charge or vice versa. Preferably, however, the zwitterion has no overall net charge and most preferably has a center of monovalent cationic charge and a center of monovalent anionic charge. Additionally, the center(s) of cationic charge are preferably permanent; that is, it is preferably a quaternary nitrogen, quaternary phosphonium or tertiary sulfonium group. Additionally, the center(s) of anionic charge are also permanent; that is, they are completely ionized at physiological pH and are preferably carboxylate, phosphate, phosphonic, phosphonate, sulfate, sulfinic, or sulfonate.

In another embodiment, the polymer contains zwitterionic pendant groups covalently attached, directly or indirectly, to the polymer back bone, and the zwitterion corresponds to Formula ZI-3:

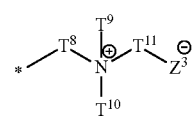

Formula ZI-3 wherein $T^8$ is a bond, hydrocarbylene, substituted hydrocarbylene, heterocyclo, or in combination with $T^9$ and $T^{10}$ and the nitrogen atom to which they are attached form a nitrogen-containing heteroaromatic ring, $T^9$ and $T^{10}$ are independently hydrogen, hydrocarbyl, substituted hydrocarbyl or heterocyclo, or, $T^9$ and $T^{10}$, in combination with $T^8$ and the nitrogen atom to which they are attached form a nitrogen-containing heteroaromatic ring, $T^{11}$ is hydrocarbylene, substituted hydrocarbylene, ether, or oxylated alkylene, $Z^3$ is carboxylate, phosphate, phosphonic, phosphonate, sulfate, sulfinic, or sulfonate, and

* designates the point of covalent attachment, direct or indirect, of the zwitterion of Formula ZI-3 to the polymer backbone.

In certain preferred embodiments in which the polymer contains zwitterionic pendant group corresponding to Formula ZI-3, $T^8$, $T^9$, $T^{10}$, and $T^{11}$ are selected from a more narrow range of substituents, $Z^3$ is carboxylate or sulfate, and the zwitterion corresponds to Formula ZI-4:

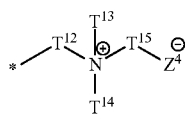

Formula ZI-4 wherein * designates the point of covalent attachment, direct or indirect, of the zwitterion of Formula ZI-4 to the polymer backbone; $T^{12}$ is a bond or —$(CH_2)_m$— with m being 1 to 3; $T^{13}$ and $T^{14}$ are independently hydrogen, alkyl, or substituted alkyl; $T^{15}$ is optionally substituted alkylene, phenylene, ether, or oxylated alkylene; and $Z^4$ is carboxylate or sulfate. For example, in this embodiment, $T^{13}$ and $T^{14}$ may independently be hydrogen or lower alkyl, e.g., methyl, ethyl, or propyl. By way of further example, in this embodiment, $T^{13}$ and $T^{14}$ may independently be hydrogen or lower alkyl, e.g., methyl, ethyl, or propyl. By way of further example, in this embodiment, $T^{15}$ may be —$(CH_2)_n$— with n being 1-8. By way of further example, in this embodiment, $T^{15}$ may be —$(CH_2)_2$— or —$(CH_2)_3$— and $T^{13}$ and $T^{14}$ may be methyl. By way of further example, in this embodiment, $T^{15}$ may be —$(CH_2)_2$— or —$(CH_2)_3$—, $T^{13}$ and $T^{14}$ may be hydrogen or alkyl. By way of further example, in this embodiment, $T^{12}$ may be —$(CH_2)_2$—, $T^{13}$ and $T^{14}$ may be methyl, $T^{15}$ may be —$(CH_2)_2$— and $Z^4$ may be carboxylate. By way of further example, in this embodiment, $T^{12}$ may be —$(CH_2)_2$—, $T^{13}$ and $T^{14}$ may be methyl, $T^{15}$ may be —$(CH_2)_3$— and $Z^4$ may be sulfate.

In certain preferred embodiments in which the polymer contains zwitterionic pendant group corresponding to Formula ZI-3, $T^8$, $T^9$ and $T^{10}$ and the nitrogen atom to which they are attached form a nitrogen-containing heteroaromatic ring. For example, $T^8$, $T^9$ and $T^{10}$ and the nitrogen atom to which they are attached may form an optionally substituted heterocycle, containing a quaternary nitrogen atom. One such embodiment corresponds to Formula ZI-5:

Formula ZI-5 wherein * designates the point of covalent attachment, direct or indirect, of the zwitterion of Formula ZI-5 to the polymer backbone; HET is a heterocycle containing a quaternary nitrogen atom, $T^{15}$ is optionally substituted alkylene, phenylene, ether, or oxylated alkylene; and $Z^4$ is carboxylate or sulfate. For example, in this embodiment, $T^{15}$ may be —$(CH_2)_n$— with n being 1-8. By way of further example, in this embodiment, $T^{15}$ may be —$(CH_2)_2$— or —$(CH_2)_3$— and $Z^4$ may be carboxylate or sulfate. By way of further example, in this embodiment, $T^{15}$ may be —$(CH_2)_3$— and $Z^4$ may be sulfate. By way of further example, in this embodiment, $T^{15}$ may be —$(CH_2)_2$— and $Z^4$ may be carboxylate. Exemplary zwitterions corresponding to Formula ZI-5 include zwitterions corresponding to Formulae ZI-6A and ZI-6B:

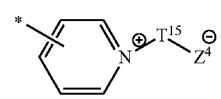

Formula ZI-6A

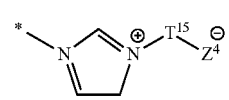

Formula ZI-6B wherein * designates the point of covalent attachment, direct or indirect, of the zwitterion of Formulae ZI-6A and ZI-6B to the polymer backbone; $T^{15}$ is optionally substituted alkylene, phenylene, ether, or oxylated alkylene; and $Z^4$ is carboxylate or sulfate. For example, in this embodiment, $T^{15}$ may be —$(CH_2)_n$— with n being 1-8. By way of further example, in this embodiment, $T^{15}$ may be —$(CH_2)_2$— or —$(CH_2)_3$— and $Z^4$ may be carboxylate or sulfate. By way of further example, in this embodiment, $T^{15}$ may be —$(CH_2)_3$— and $Z^4$ may be sulfate. By way of further example, in this embodiment, $T^{15}$ may be —$(CH_2)_2$— and $Z^4$ may be carboxylate.

In one embodiment, the polymer contains zwitterionic pendant groups covalently attached, directly or indirectly, to the polymer back bone, and the zwitterion corresponds to Formula ZI-7

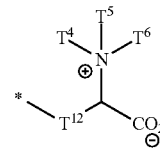

Formula ZI-7 wherein $T^4$, $T^5$ and $T^6$ are independently hydrogen, hydrocarbyl, substituted hydrocarbyl or heterocyclo; $T^{12}$ is a bond, hydrocarbylene, substituted hydrocarbylene, or heterocyclo, and * designates the point of covalent attachment, direct or indirect, of the zwitterion of Formula ZI-7 to the polymer backbone.

In one embodiment, the polymer contains zwitterionic pendant groups covalently attached, directly or indirectly, to the polymer back bone, and the zwitterion corresponds to Formula ZI-1:

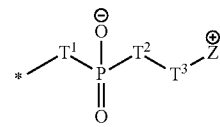

Formula ZI-1 wherein

T$^1$ and T$^2$ are independently oxygen, sulfur, NH or a bond,

T$^3$ is hydrocarbylene, substituted hydrocarbylene, ether, or oxylated alkylene, Z$^1$ is a moiety comprising a quaternary nitrogen, phosphonium or sulfonium cationic group, and

* designates the point of covalent attachment, direct or indirect, of the zwitterion of Formula ZI-1 to the polymer backbone.

In certain preferred embodiments in which the polymer contains zwitterionic pendant group corresponding to Formula ZI-1, T$^1$ and T$^2$ are oxygen, Z$^1$ is quaternary nitrogen, and the zwitterion corresponds to Formula ZI-2:

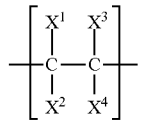

Formula ZI-2 wherein * designates the point of covalent attachment of the zwitterion of Formula ZI-2 to the polymer backbone, T$^3$ is hydrocarbylene, substituted hydrocarbylene, or oxylated alkylene, and T$^4$, T$^5$ and T$^6$ are independently hydrogen, hydrocarbyl, substituted hydrocarbyl or heterocyclo. For example, in this embodiment, T$^3$ may be —(CH$_2$)$_n$— with n being 1-8. By way of further example, in this embodiment, T$^4$, T$^5$ and T$^6$ may independently be lower alkyl, e.g., methyl, ethyl or propyl. By way of further example, in this embodiment, T$^3$ may be —(CH$_2$)$_n$— with n being 1-3, and T$^4$, T$^5$ and T$^6$ may independently be lower alkyl, e.g., methyl, ethyl or propyl. By way of further example, in this embodiment, T$^3$ may be —(CH$_2$)$_n$— with n being 1-3, and one or more of T$^4$, T$^5$ and T$^6$ may be substituted hydrocarbyl such as oligomeric phosphorylcholine (e.g., Formula 9).

Neutral Hydrophilic Pendant Groups

In one embodiment, the polymer contains neutral hydrophilic pendant groups covalently attached, directly or indirectly, to the polymer backbone. Exemplary neutral hydrophilic groups include hydroxy, thiol, oxylated alkyls (e.g., oligoethylene glycol, polyethylene glycol and/or polypropylene glycol), ether, thioether, and the like. In one such specific embodiment, the polymer contains pendant groups comprising alkoxylated moieties corresponding to Formula POA-1:

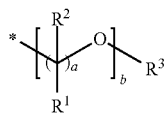

Formula POA-1 wherein a is 1-3, b is 1-8, each R$^1$ and R$^2$ is independently selected from the group consisting of hydrogen, halogen, and optionally substituted lower alkyl, R$^3$ is hydrocarbyl, substituted hydrocarbyl or heterocyclo, and * designates the point of attachment of the moieties corresponding to Formula POA-1 to the remainder of the pendant group and the backbone. By way of example, in one such embodiment, each R$^1$ and R$^2$ are hydrogen, n is 2 or 3. By way of further example, in one such embodiment, each R$^1$ and R$^2$ is hydrogen, n is 2 or 3, and b is 3-5. By way of further example, in one such embodiment, each R$^1$ and R$^2$ is hydrogen, n is 2 or 3, b is 3-5, and R$^3$ is alkyl. In one embodiment, the repeat units are derived from macromonomers containing 2-20 alkylene oxide units.

Repeat Units

In general, homopolymers or copolymers comprising zwitterionic pendant groups, neutral hydrophilic pendant groups, cationic pendant groups and/or anionic pendant groups may be prepared by polymerization of any of a wide range of monomers. In one preferred embodiment, the non-fouling polymeric material is a homopolymer or copolymer comprising repeat units derived from an olefinic monomer. Thus, for example, in one embodiment the non-fouling polymeric material comprises repeat units derived from an olefinic monomer and corresponding to Formula 1:

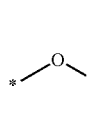

Formula 1 wherein

X$^1$ and X$^2$ are independently hydrogen, hydrocarbyl, substituted hydrocarbyl, heterocyclo, or substituted carbonyl, provided, however, X$^1$ and X$^2$ are not each selected from the group consisting of aryl, heteroaryl, and heterosubstituted carbonyl, X$^3$ is hydrogen, alkyl or substituted alkyl, X$^4$ is —OX$^{40}$, —NX$^{41}$X$^{42}$, —N$^+$X$^{41}$X$^{42}$X$^{43}$, —SX$^{40}$, aryl, heteroaryl or acyl, X$^{40}$ is hydrogen, hydrocarbyl, substituted hydrocarbyl, heterocyclo or acyl, and X$^{41}$, X$^{42}$ and X$^{43}$ are independently hydrogen, hydrocarbyl, substituted hydrocarbyl or heterocyclo.

In certain embodiments in which the non-fouling polymeric material comprises repeat units corresponding to Formula 1, it is preferred that X$^4$ of at least a fraction of the repeat units comprise alkoxylated moieties, zwitterionic moieties, anionic moieties, or cationic moieties. In such embodiments, for example, X$^1$ and X$^2$ may be hydrogen, and the polymer comprises repeat units corresponding to Formula 2:

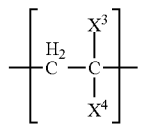

Formula 2 wherein X$^3$ is hydrogen, alkyl or substituted alkyl, and X$^4$ is a pendant group comprising an oxylated alkylene moiety, a zwitterionic moiety, an anionic moiety, or a cationic moiety. For example, X$^3$ may be hydrogen or lower alkyl. By way of further example, X$^4$ may be a pendant group comprising an oxylated alkylene moiety corresponding to Formula POA-1. By way of further example, the repeat unit of Formula 2 may be zwitterionic repeat unit comprising a zwitterionic moiety corresponding to Formula ZI-1, ZI-2, ZI-3, ZI-4, ZI-5, ZI-6A, ZI-6B, or ZI-7. By way of further example, the repeat unit of Formula 2 may be a cationic repeat unit. By way of further example, the repeat unit of Formula 2 may be an anionic repeat unit. By way of further example, X$^3$ may be hydrogen or methyl and X$^4$ may be a pendant group comprising an oxylated alkylene moiety corresponding to Formula POA-1 or a zwitterionic moiety corresponding to Formula ZI-1, ZI-2, ZI-3, ZI-4, ZI-5, ZI-6A, ZI-6B, or ZI-7.

In one presently preferred embodiment, the non-fouling polymeric material comprises repeat units corresponding to Formula 2 wherein $X^4$ is acyl and the repeat units correspond to Formula 3:

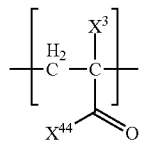

Formula 3 wherein $X^{44}$ comprises an oxylated alkylene moiety, a zwitterionic moiety, an anionic moiety, or a cationic moiety. For example, $X^{44}$ may be $-OX^{45}$, $-NX^{45}X^{46}$ or $-SX^{45}$, wherein $X^{45}$ is a substituted hydrocarbyl or heterocyclo moiety comprising an oxylated alkylene moiety, a zwitterionic moiety, an anionic moiety, or a cationic moiety, and $X^{46}$ is hydrogen, hydrocarbyl, substituted hydrocarbyl or heterocyclo. For example, $X^3$ may be hydrogen or lower alkyl. By way of further example, $X^{44}$ may be $-OX^{45}$, or $-NHX^{45}$. By way of further example, $X^{44}$ may be $-OX^{45}$, or $-NHX^{45}$ wherein $X^{45}$ comprises an oxylated alkylene moiety corresponding to Formula POA-1. By way of further example, $X^{44}$ may be $-OX^{45}$, or $-NHX^{45}$ wherein $X^{45}$ comprises a zwitterionic moiety corresponding to Formula ZI-1, ZI-2, ZI-3, ZI-4, ZI-5, ZI-6A, ZI-6B, or ZI-7. By way of further example, the repeat unit of Formula 3 may be a cationic repeat unit. By way of further example, the repeat unit of Formula 3 may be an anionic repeat unit. By way of further example, $X^3$ may be hydrogen or methyl and $X^{44}$ may comprise an oxylated alkylene moiety corresponding to Formula POA-1 or a zwitterionic moiety corresponding to Formula ZI-1, ZI-2, ZI-3, ZI-4, ZI-5, ZI-6A, ZI-6B, or ZI-7. In one particularly preferred embodiment, the polymer contains repeat units corresponding to Formula 3 and $X^{44}$ is $-O(CH_2)_2N^+(CH_3)_2(CH_2)_nSO_3^-$, $-O(CH_2)_2N^+(CH_3)_2(CH_2)_nCO_2^-$, $-NH(CH_2)_3N^+(CH_3)_2(CH_2)_nCO_2^-$, or $-NH(CH_2)_3N^+(CH_3)_2(CH_2)_nSO_3^-$, wherein n is 1-8. In one embodiment, the polymer contains repeat units corresponding to Formula 3 and $X^{44}$ is $-NH(CH_2)_mN(CH_2)_nCH_3(CH_2)_pSO_3$, $-NH(CH_2)_mN(CH_2)_nCH_3(CH_2)_pCO_2$, $-NH(CH_2)_mN^+[(CH_2)_nCH_3]_2(CH_2)_pSO_3$, $-NH(CH_2)N^+[(CH_2)_nCH_3]_2$ $(CH_2)_pCO_2$, $-NH(CH_2)_m$Ncyclo-$(CH_2)_pCO_2$, or $-NH(CH_2)_m$Ncyclo-$(CH_2)_pSO_3$, (Ncyclo is a heterocyclic structure or a heterocyclic derivative containing at least one nitrogen element), wherein m is 1-8; n is 0-5; and p is 1-8. In one embodiment, the polymer contains repeat units corresponding to Formula 3 and $X^{44}$ is $-O(CH_2)_mN(CH_2)_n$ $CH_3(CH_2)_pSO_3$, $-O(CH_2)_mN(CH_2)_nCH_3(CH_2)_pCO_2$, $-O(CH_2)_mN^+[(CH_2)_nCH_3]_2(CH_2)_pSO_3$, $-O(CH_2)N^+$ $[(CH_2)_nCH_3]_2$ $(CH_2)_pCO_2$, $-O(CH_2)_m$Ncyclo-$(CH_2)_pCO_2$, or $-O(CH_2)_m$Ncyclo-$(CH_2)_pSO_3$ wherein m is 1-8; n is 0-5; and p is 1-8. In one embodiment, the polymer contains repeat units corresponding to Formula 3 and $X^{44}$ is $-O(CH_2)_2N^+(CH_3)_2(CH_2)_3SO_3$, $-O(CH_2)_2N^+(CH_3)_2$ $(CH_2)_2CO_2$, $-NH(CH_2)_2N^+(CH_3)_2(CH_2)_3SO_3$, $-NH$ $(CH_2)_2N^+(CH_3)_2(CH_2)_2CO_2$, $-NH(CH_2)_3N^+(CH_3)_2(CH_2)_3$ $SO_3$, $-NH(CH_2)_3N^+(CH_3)_2(CH_2)_2CO_2$, $-O(CH_2)_2N^+$ $(CH_2CH_3)_2(CH_2)_3SO_3$, $-O(CH_2)_2N^+(CH_2CH_3)_2$ $(CH_2)_2CO_2$, $-O(CH_2)_2N^+(CH_2CH_2CH_2CH_3)_2$ $(CH_2)_3SO_3$, $-O(CH_2)_2N^+(CH_2CH_2CH_2CH_3)_2(CH_2)_2CO_2$ or $-NH$ $(CH_2)_3$Ncyclo-$(CH_2)_3SO_3$.

In one preferred embodiment, the non-fouling polymeric material is a zwitterionic polymer or copolymer. For example, the non-fouling polymeric material may comprise carboxybetaine repeat units and/or sulfobetaine repeat units. Alternatively, the non-fouling polymeric material may be a polyampholyte, containing anionic and cationic repeat units. Optionally, the non-fouling polymer may contain poly(ethylene oxide) repeat units and/or other neutral olefinic repeat units. Thus, for example, in one preferred embodiment, the non-fouling polymeric material is a zwitterionic polymer or copolymer comprising the repeat units of Formula 4:

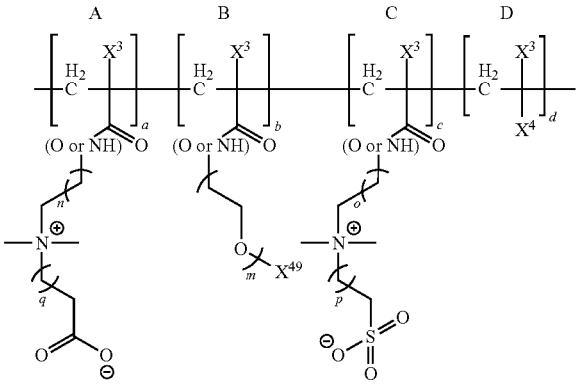

Formula 4 a is 0-1; b is 0-1; c is 0-1; d is 0-1; m is 1-20; n and o are independently 0-11; p and q are independently 0-11; $X^3$ is hydrogen, alkyl or substituted alkyl, $X^4$ is $-OX^{40}$, $-NX^{41}X^{42}$, $-SX^{40}$, aryl, heteroaryl or acyl; $X^{40}$ is hydrogen, hydrocarbyl, substituted hydrocarbyl, heterocyclo or acyl; $X^{41}$ and $X^{42}$ are independently hydrogen, hydrocarbyl, substituted hydrocarbyl or heterocyclo; and $X^{49}$ is hydrogen, hydrocarbyl or substituted hydrocarbyl, provided the sum of a, b, c and d is greater than 0 and $X^4$ of repeat unit D differs from the corresponding pendant group of repeat units A, B and C. In one such embodiment, $X^3$ is hydroxy-substituted alkyl such as hydroxypropyl.

In one embodiment, it is preferred that the non-fouling polymeric material is a zwitterionic polymer comprising repeat units corresponding to the A and/or the C repeat units. For example, in one embodiment the sum of a and c is at least 0.1. By way of further example, in one embodiment the sum of a and c is at least 0.2. By way of further example, in one embodiment the sum of a and c is at least 0.3. By way of further example, in one embodiment the sum of a and c is at least 0.4. By way of further example, in one embodiment the sum of a and c is at least 0.5. By way of further example, in one embodiment the sum of a and c is at least 0.6. By way of further example, in one embodiment the sum of a and c is at least 0.7. By way of further example, in one embodiment the sum of a and c is at least 0.8. By way of further example, in one embodiment the sum of a and c is at least 0.9. By way of further example, in one embodiment the sum of a and c is at least 0.1 and b is at least 0.1. By way of further example, in one embodiment the sum of a and c is at least 0.2 and b is at least 0.1. By way of further example, in one embodiment the sum of a and c is at least 0.3 and b is at least 0.1. By way of further example, in one embodiment the sum of a and c is at least 0.4 and b is at least 0.1. By way of further example, in one embodiment the sum of a and c is at least 0.5 and b is at least 0.1. By way of further example, in one embodiment the sum of a and c is at least 0.6 and b is at least 0.1. By way of further example, in one embodiment the sum of a and c is at least 0.7 and b is at least 0.1. By way of further example, in one embodiment the sum of a and c is at least 0.8 and b is at least 0.1. By way of further example, in one embodiment the sum of a and c is at least 0.9 and b is at least 0.1. By way of further example, in one embodiment the sum of a and c is at least 0.1 and d is at least 0.1. By way of further example, in one embodiment the sum of a and c is at least 0.2 and d is at least 0.1. By way of further example, in one embodiment the sum of a and c is at least 0.3 and d is at least 0.1. By way of further example, in one embodiment the sum of a and c is at least 0.4 and d is at least 0.1. By way of further example, in one embodiment the sum of a and c is at least 0.5 and d is at least 0.1. By way of further example, in one embodiment the sum of a and c is at least 0.6 and d is at least 0.1. By way of further example, in one embodiment the sum of a and c is at least 0.7 and d is at least 0.1. By way of further example, in one embodiment the sum of a and c is at least 0.8 and d is at least 0.1. By way of further example, in one embodiment the sum of a and c is at least 0.9 and d is at least 0.1. By way of further example, in one embodiment the sum of a and c is at least 0.1, b is at least 0.1 and d is at least 0.1. By way of further example, in one embodiment the sum of a and c is at least 0.2, b is at least 0.1 and d is at least 0.1. By way of further example, in one embodiment the sum of a and c is at least 0.3, b is at least 0.1 and d is at least 0.1. By way of further example, in one embodiment the sum of a and c is at least 0.4, b is at least 0.1 and d is at least 0.1. By way of further example, in one embodiment the sum of a and c is at least 0.5, b is at least 0.1 and d is at least 0.1. By way of further example, in one embodiment the sum of a and c is at least 0.6, b is at least 0.1, and d is at least 0.1. By way of further example, in one embodiment the sum of a and c is at least 0.7, b is at least 0.1 and d is at least 0.1. By way of further example, in one embodiment the sum of a and c is at least 0.8, b is at least 0.1 and d is at least 0.1. By way of further example, in one embodiment the sum of a and c is at least 0.9, b is at least 0.1 and d is at least 0.1. In each of these exemplary embodiments, a may be 0, c may be 0, or a and c may each be greater than 0.

In one preferred embodiment, the non-fouling polymeric material is a zwitterionic polymer or copolymer comprising the repeat units of Formula 4, m is 1-8; $X^3$ is hydrogen, alkyl or substituted alkyl, $X^4$ is $-OX^{40}$, $-NX^{41}X^{42}$, $-SX^{40}$, aryl, heteroaryl or acyl; $X^{40}$ is hydrogen, hydrocarbyl, substituted hydrocarbyl, heterocyclo or acyl; $X^{41}$ and $X^{42}$ are independently hydrogen, hydrocarbyl, substituted hydrocarbyl or heterocyclo; and $X^{49}$ is hydrogen, hydrocarbyl or substituted hydrocarbyl, with the proviso that $X^4$ of the D repeat differs from the corresponding pendant groups of the A, B or C repeat units and a, b, c, and d, in combination, are selected from one of the sets of combinations appearing in Table I:

TABLE I

| Combination | a | b | c | d |
| --- | --- | --- | --- | --- |
| 1 | 0.1-1.0 | 0.1-0.5 | 0.1-1.0 | 0.1-1.0 |
| 2a | >0 | >0.1 | 0 | 0 |
| 2b | >0 | 0 | 0 | >0.1 |
| 2c | >0 | >0.1 | 0 | >0.1 |

TABLE I-continued

| Combination | a | b | c | d |
| --- | --- | --- | --- | --- |
| 3a | >0.1 | >0.1 | 0 | 0 |
| 3b | >0.1 | 0 | 0 | >0.1 |
| 3c | >0.1 | >0.1 | 0 | >0.1 |
| 4a | >0.2 | >0.1 | 0 | 0 |
| 4b | >0.2 | 0 | 0 | >0.1 |
| 4c | >0.2 | >0.1 | 0 | >0.1 |
| 5a | >0.3 | >0.1 | 0 | 0 |
| 5b | >0.3 | 0 | 0 | >0.1 |
| 5c | >0.3 | >0.1 | 0 | >0.1 |
| 6a | >0.4 | >0.1 | 0 | 0 |
| 6b | >0.4 | 0 | 0 | >0.1 |
| 6c | >0.4 | >0.1 | 0 | >0.1 |
| 7a | >0.5 | >0.1 | 0 | 0 |
| 7b | >0.5 | >0 | 0 | >0.1 |
| 7c | >0.5 | >0.1 | 0 | >0.1 |
| 8a | >0.6 | >0.1 | 0 | 0 |
| 8b | >0.6 | 0 | 0 | >0.1 |
| 8c | >0.6 | >0.1 | 0 | >0.1 |
| 9a | >0.7 | >0.1 | 0 | 0 |
| 9b | >0.7 | >0.1 | 0 | >0.1 |
| 9c | >0.7 | 0 | 0 | >0.1 |
| 10a | >0.8 | >0.1 | 0 | 0 |
| 10b | >0.8 | 0 | 0 | >0.1 |
| 10c | >0.8 | >0.1 | 0 | >0.1 |
| 11a | >0.9 | >0.1 | 0 | 0 |
| 11b | >0.9 | 0 | 0 | >0.1 |
| 11c | >0.9 | >0.1 | 0 | >0.1 |
| 12a | 0 | >0.1 | >0 | 0 |
| 12b | 0 | 0 | >0 | >0.1 |
| 12c | 0 | >0.1 | >0 | >0.1 |
| 13a | 0 | >0.1 | >0.1 | 0 |
| 13b | 0 | 0 | >0.1 | >0.1 |
| 13c | 0 | >0.1 | >0.1 | >0.1 |
| 14a | 0 | >0.1 | >0.2 | 0 |
| 14b | 0 | 0 | >0.2 | >0.1 |
| 14c | 0 | >0.1 | >0.2 | >0.1 |
| 15a | 0 | >0.1 | >0.3 | 0 |
| 15b | 0 | 0 | >0.3 | >0.1 |
| 15c | 0 | >0.1 | >0.3 | >0.1 |
| 16a | 0 | >0.1 | >0.4 | 0 |
| 16b | 0 | 0 | >0.4 | >0.1 |
| 16c | 0 | >0.1 | >0.4 | >0.1 |
| 17a | 0 | >0.1 | >0.5 | 0 |
| 17b | 0 | >0 | >0.5 | >0.1 |
| 17c | 0 | >0.1 | >0.5 | >0.1 |
| 18a | 0 | >0.1 | >0.6 | 0 |
| 18b | 0 | 0 | >0.6 | >0.1 |
| 18c | 0 | >0.1 | >0.6 | >0.1 |
| 19a | 0 | >0.1 | >0.7 | 0 |
| 19b | 0 | >0.1 | >0.7 | >0.1 |
| 19c | 0 | 0 | >0.7 | >0.1 |
| 20a | 0 | >0.1 | >0.8 | 0 |
| 20b | 0 | 0 | >0.8 | >0.1 |
| 20c | 0 | >0.1 | >0.8 | >0.1 |
| 21a | 0 | >0.1 | >0.9 | 0 |
| 21b | 0 | 0 | >0.9 | >0.1 |
| 21c | 0 | >0.1 | >0.9 | >0.1 |
| 22a | >0 | >0.1 | >0.7 | 0 |
| 22b | >0 | 0 | >0.7 | >0.1 |
| 22c | >0 | >0.1 | >0.7 | >0.1 |
| 23a | >0.1 | >0.1 | >0.6 | 0 |
| 23b | >0.1 | 0 | >0.6 | >0.1 |
| 23c | >0.1 | >0.1 | >0.6 | >0.1 |
| 24a | >0.2 | >0.1 | >0.5 | 0 |
| 24b | >0.2 | 0 | >0.5 | >0.1 |
| 24c | >0.2 | >0.1 | >0.5 | >0.1 |
| 25a | >0.3 | >0.1 | >0.4 | 0 |
| 25b | >0.3 | 0 | >0.4 | >0.1 |
| 25c | >0.3 | >0.1 | >0.4 | >0.1 |
| 26a | >0.4 | >0.1 | >0.3 | 0 |
| 26b | >0.4 | 0 | >0.3 | >0.1 |
| 26c | >0.4 | >0.1 | >0.3 | >0.1 |
| 27a | >0.5 | >0.1 | >0.2 | 0 |
| 27b | >0.5 | >0 | >0.2 | >0.1 |
| 27c | >0.5 | >0.1 | >0.2 | >0.1 |
| 28a | >0.6 | >0.1 | >0.1 | 0 |
| 28b | >0.6 | 0 | >0.1 | >0.1 |
| 28c | >0.6 | >0.1 | >0.1 | >0.1 |

TABLE I-continued

| Combination | a | b | c | d |
|---|---|---|---|---|
| 29a | >0.7 | >0.1 | >0 | 0 |
| 29b | >0.7 | >0.1 | >0 | >0.1 |
| 29c | >0.7 | 0 | >0 | >0.1 |

In one embodiment, the non-fouling polymeric material is a polyampholyte zwitterionic polymer or copolymer comprising repeat units corresponding to repeat unit D of Formula 4. That is, d is greater than 0 and a fraction of the repeat units corresponding to repeat unit D are anionic repeat units ($X^4$ for such units is an anionic pendant group) and a fraction of the repeat units corresponding of Formula 4 are cationic repeat units ($X^4$ for such units is a cationic pendant group). For example, in one such embodiment, d is at least 0.1 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.2 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.3 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.4 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.5 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.6 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.7 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.8 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.9 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in each of said examples in this paragraph, the remaining repeat units may correspond to repeat unit A. By way of further example, in each of said examples in this paragraph, the remaining repeat units may correspond to repeat unit B. By way of further example, in each of said examples in this paragraph, the remaining repeat units may correspond to repeat unit C.

More preferably, the non-fouling polymeric material is a zwitterionic polymer or copolymer comprising repeat units corresponding to repeat unit A and/or repeat unit C of Formula 4.

In certain embodiments, the non-fouling polymeric material is a homopolymer or copolymer comprising repeat units corresponding to Formula 5, Formula 6, Formula 7, Formula 8, or Formula 9:

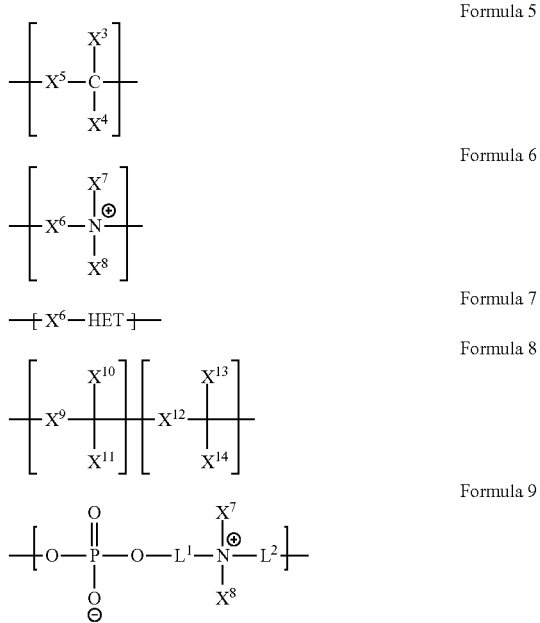

HET is part of a heterocyclic structure, $X^3$ is hydrogen, alkyl or substituted alkyl, $X^4$ is $-OX^{40}$, $-NX^{41}X^{42}$, $-SX^{40}$, aryl, heteroaryl or acyl, $X^5$ is ester, anhydride, imide, amide, ether, thioether, thioester, hydrocarbylene, substituted hydrocarbylene, heterocyclo, urethane, or urea;

$X^6$ is hydrocarbylene, substituted hydrocarbylene, heterocyclo, amide, anhydride, ester, imide, thioester, thioether, urethane, or urea;

$X^7$ is hydrogen, alkyl or substituted alkyl;

$X^8$ is an anionic moiety;

$X^9$ is hydrocarbylene, substituted hydrocarbylene, heterocyclo, amide, anhydride, ester, imide, thioester, thioether, urethane, or urea;

$X^{10}$ is hydrogen, alkyl or substituted alkyl;

$X^{11}$ is a cationic moiety;

$X^{12}$ is hydrocarbylene, substituted hydrocarbylene, heterocyclo, amide, anhydride, ester, imide, thioester, thioether, urethane, or urea;

$X^{13}$ is hydrogen, alkyl or substituted alkyl;

$X^{14}$ is an anionic moiety;

$L^1$ and $L^2$ are independently hydrocarbylene, substituted hydrocarbylene, heterocyclo, amide, anhydride, ester, imide, thioester, thioether, urethane, or urea; and $X^{40}$ is hydrogen, hydrocarbyl, substituted hydrocarbyl, heterocyclo or acyl, and $X^{41}$ and $X^{42}$ are independently hydrogen, hydrocarbyl, substituted hydrocarbyl or heterocyclo.

In one embodiment, the non-fouling polymeric material comprises repeat units corresponding to Formula 7 wherein the heterocycle, HET corresponds to Formulae 10, 11 or 12:

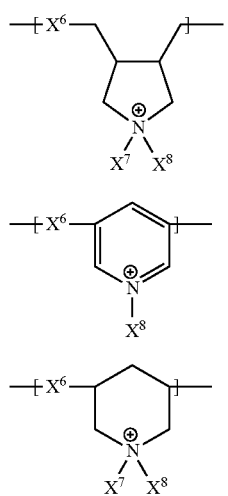

Formula 10

Formula 11

Formula 12 wherein $X^6$ is hydrocarbylene, substituted hydrocarbylene, heterocyclo, amide, anhydride, ester, imide, thioester, thioether, urethane, or urea; $X^7$ is hydrogen, alkyl or substituted alkyl; and $X^8$ is an anionic moiety.

Suitable comonomers include, but are not limited to, acrylates, acrylamides, vinyl compounds, multifunctional molecules, such as di-, tri-, and tetraisocyanates, di-, tri-, and tetraols, di-, tri-, and tetraamines, and di-, tri-, and tetrathiocyanates; cyclic monomers, such as lactones and lactams, and combination thereof. In the interests of brevity, exemplary methacrylate monomers are listed below (but it should be understood that analogous acrylate, acrylamide and methacrylamide monomers may be similarly listed and are similarly included):

Charged methacrylates or methacrylates with primary, secondary or tertiary amine groups, such as, 3-sulfopropyl methacrylate potassium salt, (2-dimethylamino)ethyl methacrylate) methyl chloride quaternary salt, [2-(methacryloyloxy)ethyl]trimethyl-ammonium chloride, methacryloyl chloride, [3-(methacryloylamino)propyl]-trimethylammonium chloride), 2-aminoethyl methacrylate hydrochloride, 2-(diethylamino)ethyl methacrylate, 2-(dimethylamino) ethyl methacrylate, 2-(tert-butylamino)ethyl methacrylate, and 2-(tert-butylamino-ethyl methacrylate.

Alkyl methacrylates or other hydrophobic methacrylates, such as ethyl methacrylate, butyl methacrylate, hexyl methacrylate, 2-ethylhexyl methacrylate, methyl methacrylate, lauryl methacrylate, isobutyl methacrylate, isodecyl methacrylate, phenyl methacrylate, decyl methacrylate, 3,3,5-trimethylcyclohexyl methacrylate, benzyl methacrylate, cyclohexyl methacrylate, stearyl methacrylate, tert-butyl methacrylate, tridecyl methacrylate, 2-naphthyl methacrylate, 2,2,3,3-tetrafluoropropyl methacrylate, 1,1,1,3,3,3-hexafluoroisopropyl methacrylate, 2,2,2-trifluoroethyl methacrylate, 2,2,3,3,3-pentafluoropropyl methacrylate, 2,2,3,4,4,4-hexafluorobutyl methacrylate, 2,2,3,3,4,4,4-heptafluorobutyl methacrylate, 2,2,3,3,4,4,5,5-octafluoropentyl methacrylate, 3,3,4,4,5,5,6,6,7,7,8,8-tridecafluorooctyl methacrylate, and 3,3,4,4,5,5,6,6,7,7,8,8,9,9,10,10,10-heptadecafluorodecyl methacrylate.

Reactive or crosslinkable methacrylates, such as 2-(trimethylsilyloxy)ethyl methacrylate, 3-(trichlorosilyl)propyl methacrylate, 3-(trimethoxysilyl)propyl methacrylate, 3-[tris(trimethylsiloxy)silyl]propyl methacrylate, trimethylsilyl methacrylate, allyl methacrylate, vinyl methacrylate, 3-(acryloyloxy)-2-hydroxypropyl methacrylate, 3-(diethoxymethylsilyl)propyl methacrylate 3-(dimethylchlorosilyl)propyl methacrylate 2-isocyanatoethyl methacrylate, glycidyl methacrylate, 2-hydroxyethyl methacrylate, 3-chloro-2-hydroxypropyl methacrylate, Hydroxybutyl methacrylate, glycol methacrylate, hydroxypropyl methacrylate, and 2-hydroxypropyl 2-(methacryloyloxy)ethyl phthalate.

Other methacrylates, such as ethylene glycol methyl ether methacrylate, di(ethylene glycol) methyl ether methacrylate, ethylene glycol phenyl ether methacrylate, 2-butoxyethyl methacrylate, 2-ethoxyethyl methacrylate, and ethylene glycol dicyclopentenyl ether methacrylate.

Multifunctional monomers, such as di, tri, or tetraacrylates and di, tri, or tetraacrylamides can be used to form highly branched structures which can provide a higher concentration of non-fouling groups on the surface. As previously noted, the non-fouling polymeric material may contain a non-zwitterionic non-fouling material, alone or in combination with a zwitterionic material. These non-fouling groups may have varying degrees of non-fouling performance in a range of environments. Suitable non-zwitterionic materials include, but are not limited to, polyethers, such as polyethylene glycol, poly(ethylene oxide-co-propylene oxide) (PEO-PPO) block copolymers, polysaccharides such as dextran, hydrophilic polymers such as polyvinylpyrrolidone (PVP) and hydroxyethyl-methacrylate (HEMA), acrylonitrile-acrylamide copolymers, heparin, heparin fragments, derivatized heparin fragments, hyaluronic acid, mixed charge materials, and materials containing hydrogen bond accepting groups, such as those described in U.S. Pat. No. 7,276,286. Suitable polymer structures included, but are not limited to, polymers or copolymers containing monomers of Formula I wherein ZI is replaced by a non-zwitterionic, non-fouling head group.

In one embodiment, the non-fouling material is a polymer containing repeat units derived from sulfobetaine-containing and/or carboxybetaine-containing monomers. Examples of monomers include sulfobetaine methacrylate (SBMA), sulfobetaine acrylamide, sulfobetaine methacrylamide, carboxybetaine methacrylate (CBMA), carboxybetaine acrylamide and carboxybetaine methacrylamide. Examples of such polymers include, but are not limited to, poly(carboxy betaine methacrylate) (polyCBMA), poly(carboxybetaine acrylamide), poly(carboxybetaine methacrylamide) poly (sulfobetaine methacrylate) (polySBMA), poly(sulfobetaine acrylamide), and poly(sulfobetaine methacrylamide). In another embodiment, the non-fouling material polymer is a polymer containing the residue of CBMA or SBMA and one or more additional monomers. The additional monomers can be zwitterionic or non-zwitterionic monomers.

In some embodiments, it is preferred to have use zwitterionic polymers that possess permanently charged groups, which, without being bound by any theory, may improve non-fouling performance because the charged groups are ionically solvated with water. The presence of commonly used groups which can have permanent charges in the zwitterionic polymers can be detected by using XPS to analyze the elements present in the top approximately 1-50 nm of the surface. One representative group commonly used in zwitterions is nitrogen in quaternary amine groups. In sulfobetaine, elemental signal of nitrogen may be approximately equivalent to a signal for sulfur. Further, techniques such as TOF-SIMS may be used to identify zwitterionic groups in the grafted polymer layer. In some preferred embodiments, the grafted polymer layer contains XPS signals of nitrogen, and optionally sulfur.

In general, the grafted polymeric material may comprise repeat units corresponding to any of Formulae 1 to 12. By way of further example, the grafted polymeric material may comprise a zwitterionic polymer. By way of further example, polymeric material may comprise repeat units corresponding to Formula 1. By way of further example, the grafted polymeric material may comprise repeat units corresponding to Formula 2. By way of further example, the grafted polymeric material may comprise repeat units corresponding to Formula 3. By way of further example, the grafted polymeric material may comprise repeat units corresponding to Formula 4. Additionally, the grafted polymeric material may comprise, as pendant groups, any of the pendant groups disclosed herein. Thus, for example, the grafted polymeric material may comprise pendant groups corresponding to any of Formulae ZI-1 to ZI-7 or POA-1. In one particularly preferred embodiment, the grafted polymeric material corresponds to Formula 1 and comprises zwitterionic pendant groups. In another particularly preferred embodiment, the grafted polymeric material corresponds to Formula 3 and comprises sulfobetaine or carboxybetaine pendant groups. In one especially preferred embodiment, the grafted polymeric material comprises repeat units derived from sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers. In general, the height and any branching of the grafted polymeric material can help to overcome surface irregularities and defects, and increased branching may reduce the ability of fouling materials to penetrate the non-fouling layer.

In one preferred embodiment, the grafted polymeric material corresponds to Formula 1 and comprises zwitterionic pendant groups and the surface modification has a thickness which is at least equal to the surface roughness of the substrate surface. In one such preferred embodiment, the grafted polymeric material corresponds to Formula 3 and comprises sulfobetaine or carboxybetaine pendant groups. In one such preferred embodiment, the grafted polymeric material comprises repeat units derived from sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers and has a global average dry thickness that is at least 110% of the global average $R_{rms}$ surface roughness of the substrate surface. In one such preferred embodiment, the grafted polymeric material is a homopolymer of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and has a global average dry thickness that is at least 200% of the global average $R_{rms}$ surface roughness of the substrate surface. In one such preferred embodiment, the grafted polymeric material is a copolymer, at least 50% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and has a global average dry thickness that is at least 200% of the global average $R_{rms}$ surface roughness of the substrate surface. In one such preferred embodiment, the grafted polymeric material is a copolymer, at least 60% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and has a global average dry thickness that is at least 200% of the global average $R_{rms}$ surface roughness of the substrate surface. In one such preferred embodiment, the grafted polymeric material is a copolymer, at least 70% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and has a global average dry thickness that is at least 200% of the global average $R_{rms}$ surface roughness of the substrate surface. In one such preferred embodiment, the grafted polymeric material is a copolymer, at least 80% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and has a global average dry thickness that is at least 200% of the global average $R_{rms}$ surface roughness of the substrate surface. In one such preferred embodiment, the grafted polymeric material is a copolymer, at least 90% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and has a global average dry thickness that is at least 200% of the global average $R_{rms}$ surface roughness of the substrate surface.

In another preferred embodiment, the grafted polymeric material corresponds to Formula 1 and comprises zwitterionic pendant groups and the surface modification, i.e., the grafted polymeric material, has a global average dry thickness of at least 50 nm. In one such preferred embodiment, the grafted polymeric material corresponds to Formula 3 and comprises sulfobetaine or carboxybetaine pendant groups. In one such preferred embodiment, the grafted polymeric material comprises repeat units derived from sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers. In one such preferred embodiment, polymeric material is a homopolymer of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers and has a global average dry thickness of at least about 50 nm, as measured by SEM under vacuum. In one such preferred embodiment, the grafted polymeric material is a copolymer, at least 50% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and has a global average dry thickness of at least about 50 nm, as measured by SEM under vacuum. In one such preferred embodiment, the grafted polymeric material is a copolymer, at least 60% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and has a global average dry thickness of at least about 50 nm, as measured by SEM under vacuum. In one such preferred embodiment, the grafted polymeric material is a copolymer, at least 70% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and has a global average dry thickness of at least about 50 nm, as measured by SEM under vacuum. In one such preferred embodiment, the grafted polymeric material is a copolymer, at least 80% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and has a global average dry thickness of at least about 50 nm, as measured by SEM under vacuum. In one such preferred embodiment, the grafted polymeric material is a copolymer, at least 90% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and has a global average dry thickness of at least about 50 nm, as measured by SEM under vacuum. By way of further example, in each of the foregoing embodiments, the global average dry thickness may be even greater, e.g., at least about 200 nm, at least about 300 nm, at least about 400 nm, or at least about 500 nm.

In another preferred embodiment, the grafted polymeric material corresponds to Formula 1 and comprises zwitterionic pendant groups and the surface modification, i.e., the grafted polymeric material, has a relatively uniform thickness. In one such preferred embodiment, the grafted polymeric material corresponds to Formula 3 and comprises sulfobetaine or carboxybetaine pendant groups. In one such preferred embodiment, the grafted polymeric material comprises repeat units derived from sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers. In one such preferred embodiment, polymeric material is a homopolymer of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers and the standard deviation of the global average dry thickness of the non-fouling grafted polymer layer not exceed 100% of the global average dry thickness of the non-fouling grafted polymer layer. In one such preferred embodiment, the grafted polymeric material is a copolymer, at least 50% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the standard deviation of the global average dry thickness of the non-fouling grafted polymer layer not exceed 100% of the global average dry thickness of the non-fouling grafted polymer layer. In one such preferred embodiment, the grafted polymeric material is a copolymer, at least 60% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the standard deviation of the global average dry thickness of the non-fouling grafted polymer layer not exceed 100% of the global average dry thickness of the non-fouling grafted polymer layer. In one such preferred embodiment, the grafted polymeric material is a copolymer, at least 70% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the standard deviation of the global average dry thickness of the non-fouling grafted polymer layer not exceed 100% of the global average dry thickness of the non-fouling grafted polymer layer. In one such preferred embodiment, the grafted polymeric material is a copolymer, at least 80% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the standard deviation of the global average dry thickness of the non-fouling grafted polymer layer not exceed 100% of the global average dry thickness of the non-fouling grafted polymer layer. In one such preferred embodiment, the grafted polymeric material is a copolymer, at least 90% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the standard deviation of the thickness of the non-fouling grafted polymer layer not exceed 100% of the global average dry thickness of the non-fouling grafted polymer layer. By way of further example, in each of the foregoing embodiments, the standard deviation of thickness may be even less, e.g., less than 50% of the global average dry thickness of the non-fouling grafted polymer layer, less than 20% of the global average dry thickness of the non-fouling grafted polymer layer, or less than 10% of the global average dry thickness of the non-fouling grafted polymer layer.

In another preferred embodiment, the grafted polymeric material corresponds to Formula 1, comprises zwitterionic pendant groups, the substrate surface and the grafted polymeric material, in combination, constitute a modified surface, and the modified surface exhibits a static contact angle of less than 40 degrees. In one such preferred embodiment, the grafted polymeric material corresponds to Formula 3 and comprises sulfobetaine or carboxybetaine pendant groups. In one such preferred embodiment, the grafted polymeric material comprises repeat units derived from sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers. In one such preferred embodiment, polymeric material is a homopolymer of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers and the modified surface exhibits a static contact angle of less than 25 degrees. In one such preferred embodiment, the grafted polymeric material is a copolymer, at least 50% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the modified surface exhibits a static contact angle of less than 25 degrees. In one such preferred embodiment, the grafted polymeric material is a copolymer, at least 60% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the modified surface exhibits a static contact angle of less than 25 degrees. In one such preferred embodiment, the grafted polymeric material is a copolymer, at least 70% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the modified surface exhibits a static contact angle of less than 25 degrees. In one such preferred embodiment, the grafted polymeric material is a copolymer, at least 80% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the modified surface exhibits a static contact angle of less than 25 degrees. In one such preferred embodiment, the grafted polymeric material is a copolymer, at least 90% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the modified surface exhibits a static contact angle of less than 25 degrees. By way of further example, in each of the foregoing embodiments, the modified surface exhibits a static contact angle may be even less, e.g., less than 24, less than 23, less than 22, less than 21, less than 20, less than 19, less than 18, less than 17, less than 16, or less than 15.

In another preferred embodiment, the grafted polymeric material corresponds to Formula 1, comprises zwitterionic pendant groups and the grafted polymeric material, i.e., the grafted polymer layer, has a volumetric swelling capacity, as measured by the magnitude of the difference between the global average dry thickness of the grafted polymer layer as determined by standard scanning electron microscopy (SEM) and the global average humidified thickness of the grafted polymer layer as determined by environmental scanning electron microscopy (ESEM), that is less than 200% of the global average dry thickness. In one such preferred embodiment, the grafted polymeric material corresponds to Formula 3 and comprises sulfobetaine or carboxybetaine pendant groups. In one such preferred embodiment, the grafted polymeric material comprises repeat units derived from sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers. In one such preferred embodiment, polymeric material is a homopolymer of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers and the grafted polymer layer has a volumetric swelling capacity, as measured by the magnitude of the difference between the global average dry thickness of the grafted polymer layer as determined by standard scanning electron microscopy (SEM) and the global average humidified thickness of the grafted polymer layer as determined by environmental scanning electron microscopy (ESEM), that is less than 200% of the global average dry thickness. In one such preferred embodiment, the grafted polymeric material is a copolymer, at least 50% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the grafted polymer layer has a volumetric swelling capacity measured by the magnitude of the difference between the global average dry thickness of the grafted polymer layer as determined by standard scanning electron microscopy (SEM) and the global average humidified thickness of the grafted polymer layer as determined by environmental scanning electron microscopy (ESEM), that is less than 200% of the global average dry thickness. In one such preferred embodiment, the grafted polymeric material is a copolymer, at least 60% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the grafted polymer layer has a volumetric swelling capacity measured by the magnitude of the difference between the global average dry thickness of the grafted polymer layer as determined by standard scanning electron microscopy (SEM) and the global average humidified thickness of the grafted polymer layer as determined by environmental scanning electron microscopy (ESEM), that is less than 200% of the global average dry thickness. In one such preferred embodiment, the grafted polymeric material is a copolymer, at least 70% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the grafted polymer layer has a volumetric swelling capacity measured by the magnitude of the difference between the global average dry thickness of the grafted polymer layer as determined by standard scanning electron microscopy (SEM) and the global average humidified thickness of the grafted polymer layer as determined by environmental scanning electron microscopy (ESEM), that is less than 200% of the global average dry thickness. In one such preferred embodiment, the grafted polymeric material is a copolymer, at least 80% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the grafted polymer layer has a volumetric swelling capacity measured by the magnitude of the difference between the global average dry thickness of the grafted polymer layer as determined by standard scanning electron microscopy (SEM) and the global average humidified thickness of the grafted polymer layer as determined by environmental scanning electron microscopy (ESEM), that is less than 200% of the global average dry thickness. In one such preferred embodiment, the grafted polymeric material is a copolymer, at least 90% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the grafted polymer layer has a volumetric swelling capacity measured by the magnitude of the difference between the global average dry thickness of the grafted polymer layer as determined by standard scanning electron microscopy (SEM) and the global average humidified thickness of the grafted polymer layer as determined by environmental scanning electron microscopy (ESEM), that is less than 200% of the global average dry thickness. By way of further example, in each of the foregoing embodiments, the grafted polymer layer has a volumetric swelling capacity that may be less than 200%, e.g., less than 100%, less than 50%, less than 25%, less than 10%, less than 5%, less than 1%, or even 0, as measured by the magnitude of the difference between the global average dry thickness of the grafted polymer layer as determined by standard scanning electron microscopy (SEM) and the global average humidified thickness of the grafted polymer layer as determined by environmental scanning electron microscopy (ESEM).

In another preferred embodiment, the grafted polymeric material corresponds to Formula 1, comprises zwitterionic pendant groups, the substrate surface and the grafted polymeric material, in combination, constitute a modified surface, and the modified surface exhibits a relatively low affinity for proteins. For example, the modified surface may exhibit a fibrinogen adsorption of less than 125 ng/cm$^2$ in a fibrinogen adsorption assay. By way of further example, in one embodiment the modified surface may exhibit a fibrinogen adsorption of less than 90 ng/cm$^2$ in a fibrinogen adsorption assay. By way of further example, in one embodiment the modified surface may exhibit a fibrinogen adsorption of less than 70 ng/cm$^2$ in a fibrinogen adsorption assay. By way of further example, it is generally preferred that the modified surface exhibit a fibrinogen adsorption of less than 50 ng/cm$^2$ in a fibrinogen adsorption assay. In one such preferred embodiment, the grafted polymeric material corresponds to Formula 3 and comprises sulfobetaine or carboxybetaine pendant groups. In one such preferred embodiment, the grafted polymeric material comprises repeat units derived from sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers. In one such preferred embodiment, polymeric material is a homopolymer of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers and the modified surface exhibits a fibrinogen adsorption of less than 30 ng/cm$^2$. In one such preferred embodiment, the grafted polymeric material is a copolymer, at least 50% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the modified surface exhibits a fibrinogen adsorption of less than 30 ng/cm$^2$. In one such preferred embodiment, the grafted polymeric material is a copolymer, at least 60% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the modified surface exhibits a fibrinogen adsorption of less than 30 ng/cm$^2$. In one such preferred embodiment, the grafted polymeric material is a copolymer, at least 70% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the modified surface exhibits a fibrinogen adsorption of less than 30 ng/cm$^2$. In one such preferred embodiment, the grafted polymeric material is a copolymer, at least 80% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the modified surface exhibits a fibrinogen adsorption of less than 30 ng/cm$^2$. In one such preferred embodiment, the grafted polymeric material is a copolymer, at least 90% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the modified surface exhibits a fibrinogen adsorption of less than 30 ng/cm$^2$. By way of further example, in each of the foregoing embodiments, the modified surface exhibits a fibrinogen adsorption that may be less than 20 ng/cm$^2$, e.g., less than 15 ng/cm$^2$, less than 12 ng/cm$^2$, less than less than 10, less than 8 ng/cm$^2$, less than 6 ng/cm$^2$, less than 4, less than 2 ng/cm$^2$, less than 1 ng/cm$^2$, less than 0.5 ng/cm$^2$, or less than less than 0.25 ng/cm$^2$.

Fluorescent and Colorimetric Labels

In one embodiment, the substrate surface and/or the grafted polymer layer is stained or labeled with one or more colorimetric labels, fluorescence labels, or combinations thereof. These labels are used to visualize the surface using the naked eye, spectroscopy, microscopy, or combinations thereof. Suitable microscopy techniques include, but are not limited to, optical microscopy, fluorescent microscopy, and combinations thereof.

The surface can be stained through a chemical reaction or by physical adsorption such as charge-charge interactions, hydrophobic interactions, or hydrophilic interactions. Labeling compounds include, but are not limited to, compounds or derivatives of rhodamine, fluorescein, coumarin, orange B, crystal violets, toluidine blue, methyl violet, nuclear fast red, methylene blue, malachite green, magenta, acriflavine, and other azo compounds.

In another embodiment the grafted polymer, such as a zwitterionic polymer, is labeled by incorporating one or more reactive labeling monomers into the polymer backbone during polymerization. These labeling monomers include, but not limited to, FITC-methacrylate, FITC-acrylate, rhodamine-methacrylate, rhodamine-acrylate, their derivatives or any other fluorescent acrylate, methacrylate, acrylamide, vinyl compound, diol or diamine. Incorporation of these groups can allow for convenient measurement of conformality and/or grafted polymer layer thickness. This may be particularly useful as a quality control metric for conformality verification during manufacturing of the grafted polymer layer on an underlying device.

In another embodiment, the grafted polymer layer is stained with one or more compounds, which can be easily visualized under an electronic microscope (SEM or TEM). These compounds include, but are not limited to osmium tetroxide and ruthenium tetroxide.

Bioactive Agents

Therapeutics, diagnostic, and/or prophylactic agents can be immobilized on or otherwise incorporated into an article of the present invention. When optionally included, such bioactive agents may be leachable or non-leachable. For example, the bioactive agent may be dissolved or otherwise contained within the substrate, or covalently or non-covalently associated with the grafted polymer layer, and leached or otherwise disassociated with the article in a controlled or uncontrolled manner (e.g., by leaching). These agents can interact passively or actively with the surrounding in vivo environment. The agents can also be used to alter the surrounding in vivo chemistry or environment. Two or more agents can be immobilized to a substrate surface, wherein the activity of the two agents is greater than either of the agents alone. A substance, material or agent that is not considered active, can become active if an active agent is immobilized on the substance, material or agent. Active agents include, but are not limited to inorganic compounds, organometallic compounds, organic compounds or any synthetic or natural, chemical or biological compounds of known or unknown therapeutic effect.

In general, a bioactive agent can be immobilized covalently or non-covalently directly on the substrate, on the undercoating layer, on the grafted polymer layer, or combinations thereof. In one embodiment, the bioactive agent is immobilized covalently by reacting one or more functional groups on the active agent with one or more functional groups on the substrate, undercoating layer, and/or grafted polymer layer. Covalent bonds can be formed by a variety of reaction mechanisms including, but not limited to, substitution, addition, and condensation reactions.

Typically, the bioactive agent will typically be immobilized on the grafted polymer layer after the grafted polymer layer has been grown from the surface. In an alternative embodiment, the bioactive agent can be co-immobilized with the grafted polymer layer in a side by side structure. In the graft-from methods, a tether can be grown from the surface and the active agent immobilized on the tether. Alternatively, the active agent can be immobilized directly on the surface without the use of a tether.

Cell adhesion agents can be immobilized to the compositions described herein. The efficacy of a cell adhesion agent in binding cells in complex environments may be enhanced by reducing non-specific protein adsorption on the surface from which they are presented, given that cell attachment may be a competitive process with other protein adsorption. Further, there may an advantage to resisting attachment of any cells other than those specifically targeted by the cell adhesion agent to prevent competitive blocking of the surface.

Examples of desirable cell attachment agents include, but are not limited to, integrin binders. Exemplary integrin binders include, but are not limited to, RGD peptides, along with a number of variants that include RGD motifs, YIGSR peptides, fibronectin, laminin or other proteins or peptides. Longer variants of these peptide may have more specific target cell binding. Further, the ability to present locally dense concentrations of cell attachment agents may increase the effectiveness of cell attachment by creating multimeric interactions. Other cell adhesion agents include, but are not limited, to REDV peptides. Tailored integrin binders can be used for a variety of applications including osteointegration.

Cell adhesion agents that bind specific immune cells may also benefit from attachment to zwitterions. Adhesion of immune cells to the biomaterial surface activates these cells and prefaces their phenotypic response, such as the transition of monocytes to macrophages that can result, in some cases, in the fusion into undesirable foreign body giant cells. The inherent resistivity to random protein fouling that zwitterions possess provides a unique platform to couple biomolecules that act as specific ligands for immune cells including neutrophils, monocytes, helper T-cells, killer T-cells, suppressor T-cells, B-cells and dendritic cells. Selection of appropriate ligands may prime these cells for beneficial instead of detrimental functions. These ligands include peptides or proteins that specifically bind immune cell receptors such as integrins, selectins, complement, or Fc gamma. When bound to these cell-associated proteins, such ligands may stimulate intracellular signaling pathways that lead to responses including cytoskeletal rearrangements, production and secretion of molecules including chemokines, cytokines and other chemoattractants, and induction of apoptosis. Desirable behaviors that could be tailored by presentation of biomolecules via zwitterionic tethers may include prevention/reduction in the secretion of proinflammatory cytokines, enhancement of phagocytosis, and modulation of the release of soluble factors that influence tissue-device integration.

Osteointegration may also be promoted or induced by factors which would benefit from the non-fouling properties and stable presentation of non-fouling materials, such as zwitterions. Osteointegration promoting agents include, but are not limited to, bone-morphogenic proteins, such as BMP2 and shortened analogues thereof. Non-fouling surfaces, such as zwitterionic surfaces, may enhance the activity of agents designed to promote desired cell regrowth over a surface. Reducing attachment of neutrophils and macrophages may inhibit the foreign body response and enable desired cell attachment and growth process to be favored.

Presentation of antithrombotic agents may also be more effective when tethered to grafted polymers, such as zwitterionic materials, relative to other tethers. The process of thrombosis involves both surface and bulk pathways. Zwitterions have shown an ability to reduce platelet attachment and activation, reducing one pathway. Combining an active antithrombotic that assists in the reduction of platelet activation or directly targets additional pathways for thrombosis with a zwitterionic tether could enhance the antithrombotic effect compared to either a non-platelet adherent surface or the antithrombotic agent alone. Suitable antithrombotic agents include, but are not limited to, thrombomodulin, heparin, heparin fragments, derivatized heparin fragments, hyaluronic acid, reversible albumin binders, tissue plasminogen activator binders, transglutimase, reversible NO binders, polylysine, sulphonated polymers, thrombin inhibitors including hirudin, urokinase, and streptokinase.

Device-centered infection remains a large problem. Non-fouling materials, such as zwitterions materials, can by themselves diminish microbial adhesion and retard biofilm development. Prevention of microbial adhesion and biofilm can be further enhanced on non-fouling surfaces, such as zwitterionic surfaces, by presentation of antimicrobials including, but not limited to, membrane-targeting antimicrobial agents, antimicrobial peptides and small molecule antimicrobial agents. Generally, antimicrobial peptides are cationic molecules with spatially separated hydrophobic and charged regions. Exemplary antimicrobial peptides include linear peptides that form an α-helical structure in membranes or peptides that form β-sheet structures, optionally stabilized with disulfide bridges in membranes. Representative antimicrobial peptides include, but are not limited to, cathelicidins, defensins, dermcidin, and more specifically magainin 2, protegrin, protegrin-1, melittin, II-37, dermaseptin 01, cecropin, caerin, ovispirin, cecropin A melittin hybrid, and alamethicin, or hybrids or analogues of other AmPs. Naturally occurring antimicrobial peptides include peptides from vertebrates and non-vertebrates, including plants, humans, fungi, microbes, and insects.

Antimicrobial peptides can be made from naturally occurring amino acids, non-naturally occurring amino acids (e.g., synthetic or semisynthetic amino acids and peptidomimetics), or combinations thereof. Antimicrobial peptides which retain their activity when immobilized on a surface are generally referred to as membrane-targeting antimicrobial agents. Antimicrobial peptides can be immobilized on the non-fouling grafted polymer layer, the substrate, the undercoating or combinations thereof by reacting a functional group on the peptide with a functional group on the non-fouling grafted polymer layer, the substrate, and/or the primer coat. For example, the peptide can be designed to have a cysteine residue which can be used to immobilize the peptide on a surface by reacting the thiol group of the cysteine residue with a thiol-reactive group on the surface.

Tethering of these agents via non-fouling materials, such as zwitterions, should provide stable, long-term activity. Additionally, immobilization of enzymes that degrade bacterial attachment and biofilm proteins, such as glycosylases, lyases, and serine-proteases, or those that degrade microbial communication signal molecules, such as N-acyl-homoserine lactone acylases, could provide improved efficacy in prevention of initial microbial adhesion events and subsequent biofilm formation.

A broad range of antimicrobial or antiseptic agents may be incorporated in the substrate or the non-fouling polymer to enhance antimicrobial activity at the surface or be released to provide antimicrobial activity in the environment surrounding the article. Suitable agents include silver metals, silver salts such as silver sulfadiazine, silver oxide, silver carbonate, silver acetate, silver alginate, silver azide, silver citrate, silver lactate, silver nitrate, silver sulfate, silver chloride, silver thiocyanate, silver-sodium-hydrogen-zirconium phosphate, silver sulfadiazine, silver cyclohexanediacetic acid and disilver 2,5-dichloro-3,6-dihydroxy-2,5-cyclohexadiene-1,4-dione, among others, a bismuth salt such as bismuth nitrate, bismuth citrate or bismuth salicylate among others, a zinc salt, a cerium salt, triclosan, combinations of chlorhexidine free base and chlorhexidine acetate, benzalkonium chloride, citrate, povidone-iodine, parachlorometaxylene, gramicidin, polymixin, norfloxacin, tobramycin, sulfamylon, polyhexamethylene biguanide, alexidine, iodine, rifampicin, miconazole, bacitracin, and minocycline, ciprofloxacin, clindamycin, erythromycin, gentamycin, tetracycline and vancomycin.

Biguanide compounds which may be used according to the invention include poly (hexamethylene biguanide) hydrochloride and chlorhexidine compounds. Chlorhexidine is the term denoting the chemical compound 1,6 bis(N5-p-chlorophenyl-N1-biguanido)hexane). Chlorhexidine compounds include chlorhexidine free base ("CHX") as well as chlorhexidine salts, such as chlorhexidine diphosphanilate, chlorhexidine digluconate ("CHG"), chlorhexidine diacetate ("CHA"), chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine mono-diglycolate, chlorhexidine dilactate, chlorhexidine di-α-hydroxy-isobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxy-napthoate, and chlorhexidine embonate.

Bismuth salts which may be used according to the invention include bismuth nitrate, bismuth citrate, bismuth salicylate, bismuth borate, bismuth mandelate, bismuth palmitate, bismuth benzoate, and bismuth sulfadiazine.

Cerium salts which may be used according to the invention include cerium nitrate and other cerium salts having a water solubility similar to cerium nitrate.

The term silver-containing compound, as used herein, refers to a compound comprising silver, either in the form of a silver atom or a silver ion unlinked or linked to another molecule via a covalent or noncovalent (e.g., ionic) linkage, including but not limited to covalent compounds such as silver sulfadiazine ("AgSD") and silver salts such as silver oxide ("$Ag_2O$"), silver carbonate ("$Ag_2CO_3$"), silver deoxycholate, silver salicylate, silver iodide, silver nitrate ("$AgNO_3$"), silver paraminobenzoate, silver paraminosalicylate, silver acetylsalicylate, silver ethylenediaminetetraacetic acid ("Ag EDTA"), silver picrate, silver protein, silver citrate, silver lactate and silver laurate.

Zinc salts which may be used according to the invention include zinc acetate and other zinc salts having a water solubility similar to zinc acetate.

The classes of bioactive agents identified above may be incorporated in the substrate or the non-fouling polymer to enhance antimicrobial activity at the surface or be released to provide antimicrobial activity in the environment surrounding the article.

Additional groups/classes of bioactive agents may be incorporated in the substrate or the non-fouling polymer to enhance antimicrobial activity at the surface or be released to provide antimicrobial activity in the environment surrounding the article and include the following groups/classes:

Antipyretics, analgesics and antiphlogistics (such as indometacin, acetylsalicylic acid, diclofenac sodium, ketoprofen, ibuprofen, mefenamic acid, azulene, phenacetin, isopropyl antipyrine, acetaminophen, benzadac, phenylbutazone, flufenamic acid, acetylsalicylic acid (aspirin), paracetamol, phenazone, sodium salicylate, salicylamide, sazapyrine, and etodolac) Opioid analgesics (such as buprenorphine, dextromoramide, dextropropoxyphene, fentanyl, alfentanil, sufentanil, hydromorphone, methadone, morphine, oxycodone, papavereturn, pentazocine, pethidine, phenopefidine, codeine dihydrocodeine) Non-selective COX inhibitors such as salicylic acid derivatives, aspirin, sodium salicylate, choline magnesium trisalicylate, salsalate, diflunisal, sulfasalazine and olsalazine). Para-aminophenol derivatives such as acetaminophen. Indole and indene acetic acids such as indomethacin and sulindac. Heteroaryl acetic acids such as tolmetin, dicofenac and ketorolac. Arylpropionic acids such as ibuprofen, naproxen, flurbiprofen, ketoprofen, fenoprofen and oxaprozin. Anthranilic acids (fenamates) such as mefenamic acid and meloxicam. Enolic acids such as the oxicams (piroxicam, meloxicam). Alkanones such as nabumetone. Selective COX-2 Inhibitors (such as diaryl-substituted furanones such as rofecoxib; diaryl-substituted pyrazoles such as celecoxib; indole acetic acids such as etodolac and sulfonanilides such as nimesulide)

Anti-inflammatory steroids (such as cortisone, hydrocortisone, prednisone, dexamethasone, methylprednisolone, triamcinolone beclomethasone flunisolide, fluticasone propionate triamcinolone acetonide budesonide loterednol etabonate and mometasone, aclometasone, desonide, hydrocortisone, betamethasone, clocortolone, desoximetasone, fluocinolone, flurandrenolide, mometasone, prednicarbate; amcinonide, desoximetasone, diflorasone, fluocinolone, fluocinonide, halcinonide, clobetasol, augmented betamethasone, diflorasone, halobetasol, prednisone, dexamethasone and methylprednisolone and their derivatives and)

Antiulcer drugs (such as ecabet sodium, enprostil, sulpiride, cetraxate hydrochloride, gefarnate, irsogladine maleate, cimetidine, ranitidine hydrochloride, famotidine, nizatidine and roxatidine acetate hydrochloride)

Coronary vasodilators (such as nifedipine, isosorbide dinitrate, diltiazem hydrochloride, trapidil, dipyridamole, dilazep hydrochloride, verapamil, nicardipine, nicardipine hydrochloride and verapamil hydrochloride)

Peripheral vasodilators (such as ifenprodil tartrate, cinepacide maleate, ciclandelate, cynnaridine and pentoxyphylin)

Antibiotics (such as ampicillin, amoxicillin, cefalexin, cephalexin, cefoxytin and cephalothin, erythromycmethyl succinate, vacampicillin hydrochloride, minocycline hydrochloride, chloramphenicol, tetracycline, erythromycin, ceftazidime, cefuroxime sodium, aspoxicillin chloramphenicol, clindamycin, erythromycin, erythromycin ethyl carbonate, erythromycin estolate, erythromycin glucepate, erythromycin ethylsuccinate, erythromycin lactobionate, roxithromycin, lincomycin, natamycin, nitrofurantoin, spectinomycin, vancomycin, aztreonarn, colistin IV, metronidazole, tinidazole, fusidic acid, trimethoprim, and 2-thiopyridine N-oxide)

Synthetic antimicrobials (such as nalidixic acid, piromidic acid, pipemidic acid trihydrate, enoxacin, cinoxacin, of loxacin, norfloxacin, ciprofloxacin hydrochloride and sulfamethoxazole-trimethoprim)

Antiviral agents (such as acyclovir, ganciclovir, acyclovir prodrugs, famcyclovir, zidovudine, didanosine, stavudine, lamivudine, zalcitabine, saquinavir, indinavir, ritonavir, n-docosanol, tromantadine and idoxuridine)

Anticonvulsants (such as propantheline bromide, atropine sulfate, oxitropium bromide, timepidium bromide, scopolamine butylbromide, trospium chloride, butropiumbromide, N-methylscopolaminemethylsulfate and methyloctatropine bromide)

Antitussives (such as tipepedine hibenzate, methylephedrine hydrochloride, codeine phosphate, tranilast, dextromethorphan hydrobromide, dimemorfan phosphate, clobutinol hydrochloride, fominoben hydrochloride, benproperine phosphate, eprazinone hydrochloride, clofedanol hydrochloride, ephedrine hydrochloride, noscapine, pentoxyverine citrate, oxeladin citrate and isoaminyl citrate)

Expectorants (such as bromhexine hydrochloride, carbocysteine, ethyl cysteine hydrochloride and methylcysteine hydrochloride)

Bronchodilators (such as theophylline, aminophylline, sodium cromoglicate, procaterol hydrochloride, trimetoquinol hydrochloride, diprophilline, salbutamol sulfate, clorprenaline hydrochloride, formoterol fumarate, ocriprenaline sulfate, pilbuterol hydrochloride, hexoprenaline sulfate, bitolterol mesilate, clenbuterol hydrochloride, terbutaline sulfate, malbuterol hydrochloride, fenoterol hydrobromide and methoxyphenamine hydrochloride), (13) cardiotonics (such as dopamine hydrochloride, dobutamine hydrochloride, docarpamine, denopamine, caffeine, digoxin, digitoxin and ubidecarenone)

Diuretics (such as furosemide, acetazolamide, triclormethiazide, methylclothiazide, hydrochlorothiazide, hydroflumethiazide, ethiazide, cyclopenthiazide, spironolactone, triamterene, florothiazide, piretanide, mefruside, etacrynic acid, azosemide and clofenamide)

Muscle relaxants (such as chlorphenesin carbamate, tolperisone hydrochloride, eperisone hydrochloride, tizanidine hydrochloride, mefenicine, chlorzoxazone, phenprobamate, methocarbamol, chlormezazone, pridinol mesilate, afloqualone, baclofen and dantrolene sodium)

Cerebral metabolism ameliorants (such as nicergoline, meclofenoxate hydrochloride and taltirelin), Minor tranquilizers (such as oxazolam, diazepam, clotiazepam, medazepam, temazepam, fludiazepam, meprobamate, nitrazepam and chlordiazepoxide)

Major tranquilizers (such as sulpiride, clocapramine hydrochloride, zotepine, chlorpromazine and haloperidol)

Beta-blockers (such as bisoprolol fumarate, pindolol, propranolol hydrochloride, carteolol hydrochloride, metoprolol tartrate, labetanol hydrochloride, acebutolol hydrochloride, bufetolol hydrochloride, alprenolol hydrochloride, arotinolol hydrochloride, oxprenolol hydrochloride, nadolol, bucumorol hydrochloride, indenolol hydrochloride, timolol maleate, befunolol hydrochloride and bupranolol hydrochloride)

Antiarrthymics (such as procainamide hydrochloride, diso-pyramide, ajmaline, quinidine sulfate, aprindine hydrochloride, propafenone hydrochloride, mexiletine hydrochloride and azmilide hydrochloride)

Athrifuges (such as allopurinol, probenicid, colchicine, sulfinpyrazone, benzbromarone and bucolome)

Anticoagulants/Antiplatelets (such as heparin, chondroiten sulfate ticlopidine hydrochloride, dicumarol, potassium warfarin, and (2R,3R)-3-acetoxy-5-[2-(dimethylamino)ethyl]-2,3-dihydro-8-methyl-2-(4-me-thylphenyl)-1,5-benzothiazepin-4(5H)-onemaleate)

Thrombolytics (such as stretokinase, urokinase and tissue plasminogin activators, methyl (2E,3Z)-3-benzylidene-4-(3,5-dimethoxy-α-methylbenzyliden-e)-N-(4-methylpiperazin-1-yl)-succinamate hydrochloride), Liver disease drugs (such as (±)r-5-hydroxymethyl-t-7-(3,4-dimethoxyphenyl)-4-oxo-4,5,6,7-tetrahydro-obenzo[b]furan-c-6-carboxylactone)

Antiepileptics (such as phenyloin, sodium valproate, metalbital and carbamazepine)

Antihistamines (such as chlorpheniramine maleate, clemastine fumarate, mequitazine, alimemazine tartrate, cyproheptadine hydrochloride and bepotastin besilate)

Antiemitics (such as difenidol hydrochloride, metoclopramide, domperidone and betahistine mesilate and trimebutine maleate), Depressors (such as dimethylaminoethyl reserpilinate dihydrochloride, rescinnamine, methyldopa, prazocin hydrochloride, bunazosin hydrochloride, clonidine hydrochloride, budralazine, urapidil and N-[6-[2-[(5-bromo-2-pyrimidinyl)oxy]ethoxy]-5-(4-methylphenyl)-4-pyri-midinyl]-4-(2-hydroxy-1,1-dimethyl-ethyl)benzenesulfonamide sodium)

Hyperlipidemia agents (such as pravastatin sodium and fluvastatin sodium)

Sympathetic nervous stimulants (such as dihydroergotamine mesilate and isoproterenol hydrochloride, etilefrine hydrochloride)

Oral diabetes therapeutic drugs (such as glibenclamide, tolbutamide and glimidine sodium)

Oral carcinostatics (such as malimastat)

Alkaloid narcotics (such as morphine, codeine and cocaine)

Vitamins (such as vitamin B1, vitamin B2, vitamin B6, vitamin B12, vitamin C and folic acid)

Thamuria therapeutic drugs (such as flavoxate hydrochloride, oxybutynin hydrochloride and terolidine hydrochloride)

Angiotensin converting enzyme inhibitors (such as imidapril hydrochloride, enalapril maleate, alacepril and delapril hydrochloride).

Non-steroidal anti-inflammatory agents [including their racemic mixtures or individual enantiomers where applicable] (such as ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketoralac, flufenisal, salsalate, triethanolamine salicylate, aminopyrine, antipyrine, oxyphenbutazone, apazone, cintazone, flufenamic acid, clonixerl, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate)

Antineoplastic/antiangiogenic (Such as acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, Bacillus calmette-guerin (BCG), Baker's Antifol (soluble), beta-2'-deoxythioguanosine, bisantrene hcl, bleomycin sulfate, busulfan, buthionine sulfoximine, BWA 773U82, BW 502U83.HCl, BW 7U85 mesylate, ceracemide, carbetimer, carboplatin, carmustine, chlorambucil, chloroquinoxaline-sulfonamide, chlorozotocin, chromomycin A3, cisplatin, cladribine, corticosteroids, Corynebacterium parvum, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, doxorubicin, echinomycin, edatrexate, edelfosine, eflornithine, Elliott's solution, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5-fluorouracil, Fluosol®, flutamide, gallium nitrate, gemcitabine, goserelin acetate, hepsulfam, hexamethylene bisacetamide, homoharringtonine, hydrazine sulfate, 4-hydroxyandrostenedione, hydroxyurea, idarubicin HCl, ifosfamide, interferon alfa, interferon beta, interferon gamma, interleukin-1 alpha and beta, interleukin-3, interleukin-4, interleukin-6,4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extraction residue of Bacillus calmette-guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor, uracil mustard, vinblastine sulfate, vincristine sulfate, vindesine, vinorelbine, vinzolidine, Yoshi 864, zorubicin, and mixtures thereof)

Immunosuppressant agents (such as cyclosporine A, mycophenolic acid, tacrolimus, rapamycin, rapamycin analogues, azathioprine, recombinant or monoclonal antibodies to interleukins, T-cells, B-cells and/or their receptors.

Vasodilators (such as cyclandelate, isoxsuprine, papaverine, dipyrimadole, isosorbide dinitrate, phentolamine, nicotinyl alcohol, co-dergocrine, nicotinic acid, glycerl trinitrate, pentaerythritol tetranitrate and xanthinol)

Antiproliferative agents (such as paclitaxel, actinomycin D, rapamycin, tacrolimus, everolimus, dexamethasone and rapamycin analogues)

Local anaesthetics (such as benzocaine, bupivacaine, amethocaine, lignocaine, lidocaine, cocaine, cinchocaine, dibucaine, mepivacaine, prilocalne, etidocaine, veratridine (specific c-fiber blocker) and procaine)

Antifungals (such as amorolfine, isoconazole, clotrimazole, econazole, miconazole, nystatin, terbinafine, bifonazole, amphotericin, griseo fulvin, ketoconazole, fluconazole and flucytosine, salicylic acid, fezatione, ticlatone, tolnaftate, triacetin, zinc, pyrithione and sodium pyrithione)

Agents/chemicals that block microbial attachment to target cells and/or inhibits entry of infectious pathogens (e.g., sulphated and sulponated polymers such as PC-515 (carrageenan), Pro-2000, and Dextrin 2 Sulphate)

Antiretroviral agents (e.g., PMPA gel) that prevent retroviruses from replicating in the cells Agents which change the condition of the tissue to make it hostile to the pathogen (such as substances which alter mucosal pH (e.g., Buffer Gel and Acidform);

Agents that treat or prevent an allergic or immune response and/or cellular proliferation (such as various cytokine inhibitors such as humanized anti-cytokine antibodies, anti-cytokine receptor antibodies, recombinant antagonists, or soluble receptors; various leucotriene modifiers such as zafirlukast, montelukast and zileuton; immunoglobulin E (IgE) inhibitors such as Omalizumab (an anti-IgE monoclonal antibody) and secretory leukocyte protease inhibitor) and SYK Kinase inhibitors)

Agents that prevent restenosis (such as paclitaxel, sirolimus, everolimus, vincristine, biolimus, mycophenolic acid, ABT-578, cervistatin, simvastatin, methylprednisolone, dexamethasone, actinomycin-D, angiopeptin, L-arginine, estradiol, 17-β-estradiol, tranilast, methotrexate, batimistat, halofuginone, BCP-671, QP-2, lantrunculin D, cytochalasin A, nitric oxide, and analogues and derivatives)

Growth factors and inflammatory cytokines involved in angiogenesis, fibroblast migration, fibroblast proliferation, ECM synthesis and tissue remodeling, such as epidermal growth factor (EGF) family, transforming growth factor-α (TGF-α), transforming growth factor-β (TGF-9-1, TGF-9-2, TGF-9-3, platelet-derived growth factor (PDGF), fibroblast growth factor (acidic—aFGF; and basic—bFGF), fibroblast stimulating factor-1, activins, vascular endothelial growth factor (including VEGF-2, VEGF-3, VEGF-A, VEGF-B, VEGF-C, placental growth factor—PlGF), angiopoietins, insulin-like growth factors (IGF), hepatocyte growth factor (HGF), connective tissue growth factor (CTGF), myeloid colony-stimulating factors (CSFs), monocyte chemotactic protein, granulocyte-macrophage colony-stimulating factors (GM-CSF), granulocyte colony-stimulating factor (G-CSF), macrophage colony-stimulating factor (M-CSF), erythropoietin, interleukins (particularly IL-1, IL-8, and IL-6), tumor necrosis factor-α (TNF9), nerve growth factor (NGF), interferon-α, interferon-β, histamine, endothelin-1, angiotensin II, growth hormone (GH), and synthetic peptides, analogues or derivatives of these factors are also suitable for release from specific implants and devices to be described later. Other examples include CTGF (connective tissue growth factor); inflammatory microcrystals (e.g., crystalline minerals such as crystalline silicates); bromocriptine, methylsergide, methotrexate, chitosan, N-carboxybutyl chitosan, carbon tetrachloride, thioacetamide, fibrosin, ethanol, bleomycin, naturally occurring or synthetic peptides containing the Arg-Gly-Asp (RGD) sequence, generally at one or both termini (see e.g., U.S. Pat. No. 5,997,895), and tissue adhesives, such as cyanoacrylate and crosslinked poly(ethylene glycol)-methylated collagen compositions, such as described below. Other examples of fibrosis-inducing agents include bone morphogenic proteins (e.g., BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Of these, BMP-2, BMP-3, BMP-4, BMP-5, BMP-6, and BMP-7 are of particular utility. Bone morphogenic proteins are described, for example, in U.S. Pat. Nos. 4,877,864; 5,013,649; 5,661,007; 5,688,678; 6,177,406; 6,432,919; and 6,534,268 and Wozney, J. M., et al. (1988) Science: 242(4885); 1528 1534.

Other representative fibrosis-inducing agents include components of extracellular matrix (e.g., fibronectin, fibrin, fibrinogen, collagen (e.g., bovine collagen), fibrillar and non-fibrillar collagen, adhesive glycoproteins, proteoglycans (e.g., heparin sulfate, chondroitin sulfate, dermatan sulfate), hyaluronan, secreted protein acidic and rich in cysteine (SPARC), thrombospondins, tenacin, and cell adhesion molecules (including integrins, vitronectin, fibronectin, laminin, hyaluronic acid, elastin, bitronectin), proteins found in basement membranes, and fibrosin) and inhibitors of matrix metalloproteinases, such as TIMPs (tissue inhibitors of matrix metalloproteinases) and synthetic TIMPs, e.g., marimistat, batimistat, doxycycline, tetracycline, minocycline, TROCADE, Ro-1130830, CGS 27023A, and BMS-275291.

Anti-thrombotic and/or antiplatelet agents (include heparin, heparin fragments, organic salts of heparin, heparin complexes (e.g., benzalkonium heparinate, tridodecylammonium heparinate, heparin-tridodecylmethylammonium chloride, heparin-benzalkonium chloride, heparin-steralkonium chloride, heparin-poly-N-vinyl-pyrrolidone, heparin-lecithin, heparin-didodecyldimethylammonium bromide, heparin-pyridinium chloride, and heparin-synthetic glycolipid complex), dextran, sulfonated carbohydrates such as dextran sulphate, coumadin, coumarin, heparinoid, danaparoid, argatroban chitosan sulfate, chondroitin sulfate, danaparoid, lepirudin, hirudin, AMP, adenosine, 2-chloroadenosine, aspirin, phenylbutazone, indomethacin, meclofenamate, hydrochloroquine, dipyridamole, iloprost, streptokinase, and factor Xa inhibitors, such as DX9065a, magnesium, and tissue plasminogen activator. In one aspect, the anti-thrombotic agent is a modified heparin compound, such as a hydrophobically modified heparin or modified hirudin compound (e.g., stearylkonium heparin, benzalkonium heparin, cetylkonium heparin, or trdodecylmethyl ammonium heparin). Further examples of anti-thrombotic agents include plasminogen, lys-plasminogen, alpha-2-antiplasmin, urokinase, ticlopidine, clopidogrel, glycoprotein IIb/IIIa inhibitors such as abciximab, eptifibatide, and tirogiban. Other agents capable of affecting the rate of clotting include glycosaminoglycans, danaparoid, 4-hydroxycoumarin, warfarin sodium, dicumarol, phenprocoumon, indan-1,3-dione, acenocoumarol, anisindione, and rodenticides including bromadiolone, brodifacoum, diphenadione, chlorophacinone, and pidnone).

Polypeptide drugs (such as but are not limited to, insulin; growth factors, such as epidermal growth factor (EGF), insulin-like growth factor (IGF), transforming growth factor (TGF), nerve growth factor (NGF), platelet-derived growth factor (PDGF), bone morphogenic protein (BMP), fibroblast growth factor and the like; somatostatin; somatotropin; somatropin; somatrem; calcitonin; parathyroid hormone; colony stimulating factors (CSF); clotting factors; tumor necrosis factors; interferons; interleukins; gastrointestinal peptides, such as vasoactive intestinal peptide (VIP), cholecytokinin (CCK), gastrin, secretin, and the like; erythropoietins; growth hormone and GRF; vasopressins; octreotide; pancreatic enzymes; dismutases such as superoxide dismutase; thyrotropin releasing hormone (TRH); thyroid stimulating hormone; luteinizing hormone; LHRH; GHRH; tissue plasminogen activators; macrophage activator; chorionic gonadotropin; heparin; atrial natriuretic peptide; hemoglobin; retroviral vectors; relaxin; cyclosporin; oxytocin; and peptide or polypeptide vaccines. Cell response modifiers. (Cell response modifiers include chemotactic factors such as platelet-derived growth factor (PDGF), pigmented epithelium-derived factor (PEDF), neutrophil-activating protein, monocyte chemoattractant protein, macrophage-inflammatory protein, SIS (small inducible secreted) proteins, platelet factor, platelet basic protein, melanoma growth stimulating activity, epidermal growth factor, transforming growth factor (alpha), fibroblast growth factor, platelet-derived endothelial cell growth factor, insulin-like growth factor, nerve growth factor, vascular endothelial growth factor, bone morphogenic proteins, and bone growth/cartilage-inducing factor (alpha and beta). Other cell response modifiers (Such as the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, and activin) Therapeutic enzymes (Such as proteases, phospholipases, lipases, glycosidases, cholesterol esterases, and nucleases) Peptide-nucleic acid (PNA) conjugate, polysaccharide-peptide conjugates such as glyosylated polypeptides; glycoproteins), a poly(ethyleneglycol)-polypeptide conjugate (PEG-ylated polypeptides), or polymer pharmaceuticals.

Antibodies and antibody fragments (Such as, but are not limited to, therapeutic antibodies include trastuzumab, alemtuzumab, gemtuzumab, rituximab, ibritumomab, tositumomab, edrecolomab, cetuximab, bevacizumab, Ranibizumab, satumomab, pertuzumab, and daclizumab)

Therapuetic enzymes (Such as recombinant human tissue plasminogen activator (alteplase), RNaseA, RNaseU, chondroitinase, pegaspargase, arginine deaminase, vibriolysin, sarcosidase, N-acetylgalactosamine-4-sulfatase, glucocerebrocidase, α-galactosidase, and laronidase)

Enzyme inhibitors (Such as edrophonium chloride, N-methylphysostigmine, neostigmine bromide, physostigmine sulfate, tacrine HCL, tacrine, 1-hydroxy maleate, iodotubercidin, p-bromotetramisole, 10-(α-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylaminie, N-monomethyl-L-arginine acetate, carbidopa, 3-hydroxybenzylhydrazine HCl, hydralazine HCl, clorgyline HCl, deprenyl HCl L(−), deprenyl HCl D(+), hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-di-phenylvalerate hydrochloride, 3-isobutyl-1-methylxanthne, papaverine HCl, indomethacind, 2-cyclooctyl-2-hydroxyethylamine hydrochloride, 2,3-dichloro-α-methylbenzylamine (DCMB), 8,9-dichloro-2,3,4,5-tetrahydro-1H-2-benzazepine hydrochloride, p-aminoglutethimide, p-aminoglutethimide tartrate R(+), p-aminoglutethimide tartrate S(−), 3-iodotyrosine, alpha-methyltyrosine L(−), alpha-methyltyrosine D(−), cetazolamide, dichlorphenamide, 6-hydroxy-2-benzothiazolesulfonamide, and allopurinol)

Steroids (Such as glucocorticoids, estrogens and androgens. By way of example, steroids can include dexamethasone, dexamethasone acetate, dexamethasone sodium phosphate, cortisone, cortisone acetate, hydrocortisone, hydrocortisone acetate, hydrocortisone cypionate, hydrocortisone sodium phosphate, hydrocortisone sodium succinate, prednisone, prednisolone, prednisolone acetate, prednisolone sodium phosphate, prednisolone tebutate, prednisolone pivalate, triamcinolone, triamcinolone acetonide, triamcinolone hexacetonide, triamcinolone diacetate, methylprednisolone, methylprednisolone acetate, methylprednisolone sodium succinate, flunsolide, beclomethasone dipropionate, betamethasone sodium phosphate, betamethasone, vetamethasone disodium phosphate, vetamethasone sodium phosphate, betamethasone acetate, betamethasone disodium phosphate, chloroprednisone acetate, corticosterone, desoxycorticosterone, desoxycorticosterone acetate, desoxycorticosterone pivalate, desoximethasone, estradiol, fluorocortisone, fluorocortisone acetate, dichlorisone acetate, fluorohydrocortisone, fluorometholone, fluprednisolone, paramethasone, paramethasone acetate, androsterone, fluoxymesterone, aldosterone, methandrostenolone, methylandrostenediol, methyl testosterone, norethandrolone, testosterone, testosterone enanthate, testosterone propionate, equilenin, equilin, estradiol benzoate, estradiol dipropionate, estriol, estrone, estrone benzoate, acetoxypregnenolone, anagestone acetate, chlormadinone acetate, fluorogestone acetate, hydroxymethylprogesterone, hydroxymethylprogesterone acetate, hydroxyprogesterone, hydroxyprogesterone acetate, hydroxyprogesterone caproate, melengestrol acetate, normethisterone, pregnenolone, progesterone, ethynyl estradiol, mestranol, dimethisterone, ethisterone, ethynodiol diacetate, norethindrone, norethindrone acetate, norethisterone, fluocinolone acetonide, flurandrenolone, hydrocortisone sodium succinate, methylprednisolone sodium succinate, prednisolone phosphate sodium, triamcinolone acetonide, hydroxydione sodium, spironolactone, oxandrolone, oxymetholone, prometholone, testosterone cypionate, testosterone phenylacetate, estradiol cypionate, and norethynodrel, analogs thereof, or combinations thereof)

Non-steroidal anti-inflammatory agents [including their racemic mixtures or individual enantiomers where applicable] (Such as ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketoralac, flufenisal, salsalate, triethanolamine salicylate, aminopyrine, antipyrine, oxyphenbutazone, apazone, cintazone, flufenamic acid, clonixerl, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate).

Formulations of the above antimicrobial or antiseptic agents may be enhanced by altering the solubility or physical characteristics of the agent if salts or crystals are used, for instance by using nanoparticles or other formulations with reduced size or enhanced surface area per mass.

Non-fouling surfaces, such as zwitterionic surfaces, may also present a particularly attractive surface for immobilization of biomolecules, such as antibodies, for use as biosensors. Immobilized antibodies on non-fouling surface surfaces, such as zwitterionic surfaces, have been demonstrated to retain both antibody activity and antigen specificity in whole blood. "Smart" implanted medical devices that detect undesirable activation of specific immune pathways, such as proinflammatory cytokines, or the presence of a possible infectious agent, perhaps through detection of a secreted microbial toxin, could be designed, for example, by utilizing specific antibodies or biomolecules tailored to monitor these threats. Appropriate therapeutic strategies could then be employed before an unfavorable outcome, such as infection, arises. The stability of the zwitterionic molecule in vivo provides a unique advantage in this type of scenario due to its longevity.

Polymerization

The polymeric surface modifications of the present invention may be formed by synthetic means including, but not limited to, free radical polymerization, ionic polymerization, atom transfer radical polymerization (ATRP), nitroxide mediated polymerization (NMP), reversible addition-fragmentation polymerization (RAFT), ring opening metathesis polymerization (ROMP), telluride mediated polymerization (TERP) or acyclic diene metathesis polymerization (ADMET), and UV, thermal, or redox free radical initiated polymerization. In a preferred embodiment, the polymer is formed using an oxidizing agent and a reducing agent, in combination, i.e., a redox pair, as the polymerization initiator in a redox free radical polymerization.

In some embodiments, it is preferable that initiators and ligands often used in ATRP such as bromine-containing initiators and ligands such as bipyridine are not used in the process as they may be non-biocompatible at certain levels. In further embodiments, it is preferred not to have a detectable level of bipyridine in the polymer modified article or in aqueous or organic extractions of the polymer modified article. In further embodiments, it is preferred not to have a detectable level of bromine in the polymer modified article or in aqueous or organic extractions of the polymer modified article. Bipyridine and bromine can be detected with HPLC or UV analysis.

The general procedure described herein can be modified as necessary to accommodate different substrate materials, initiators systems, and/or monomer compositions and to incorporate high concentrations of the initiator into and/or onto the substrate or undercoating layer. High initiator concentrations may result in highly densely coated surfaces which improves the non-fouling activity of the composition. For example, highly densely coated surfaces contain polymer chains that reduce penetration of fouling molecules into the coating. Without being bound to any particular theory it is presently theorized that a reservoir of initiator incorporated in the substrate may enhance re-initiation and branching of non-fouling polymer from the surface and near the surface of the substrate. This re-initiation, in turn, may increase the thickness of the non-fouling polymer (in other words, the distance the non-fouling polymer stretches above the substrate in a direction normal to the substrate surface) as well as the degree of branching.

In general, and as described in greater detail elsewhere herein, incorporation of initiator into the substrate enables polymeric material to be grafted from the substrate surface and from within the near-surface zone beneath the substrate surface. In general, however, it is preferred that the grafted polymeric material not extend too far into the substrate; thus, in one embodiment grafted polymeric material is present in the near-surface zone but not at greater depths, i.e., not in the substrate bulk. The maximum depth to which near-surface zone extends, i.e., the distance of the lower boundary of the near-surface zone as measured from the substrate surface is, at least in part, a function of the initiator and the technique used to incorporate initiator in the substrate. Typically, however, it is generally preferred that the lower boundary not be greater than 20 micrometers from the substrate surface. By way of example, the lower boundary may not be greater than 15 micrometers from the substrate surface. By way of further example, the lower boundary may not be greater than 10 micrometers from the substrate surface. Similarly, the minimum depth of near-surface zone, i.e., the distance of the upper boundary of the near-surface zone from the substrate surface is, at least in part, also a function of the initiator and the technique used to incorporate initiator in the substrate. Typically, however, the upper boundary will be at least 0.1 micrometers from the substrate surface. By way of example, the upper boundary may be at least 0.2 micrometers from the substrate surface. By way of further example, the upper boundary may be at least 0.3 micrometers from the substrate surface.

The quality of the surface modification formed in the polymerization process is, at least in part, influenced by the quality of the surface of the substrate prior to polymerization. For example, prior to polymerization, the surface may be contaminated, intentionally or otherwise, with particles, waxes and other compositions that may remain on the surface of the substrate as an artifact of the manufacturing process, subsequent handling of the substrate, and/or as part of the intended substrate composition. The substrate surface may also include significant surface roughness, physical defects such as scratches, pinholes, or voids, and chemical defects, such as particle(s) of radiopacifing agents (such as barium sulfate, bismuth oxychloride, bismuth subcarbonate, bismuth trioxide, lanthanum oxide, tantalum pentoxide, and metallic gold, silver, platinum, palladium, tungsten, and tantalum) that are only partially contained within the substrate. For example, substrates containing barium sulfate typically have some barium sulfate particles that are partially contained within the substrate and partially exposed; the exposed portions of such barium sulfate particles may extend from the surface of a substrate to a height of as much as 1 micrometer (as measured from the surface of the substrate using SEM).

In accordance with one embodiment, the substrate surface is preferably pre-treated prior to polymerization. For example, the substrate surface may be cleaned using water, solvents, surfactants, enzymes, or other cleaning solutions or gases to remove particles, waxes or other foreign compositions that may be on or near the surface of the substrate. Alternatively, or additionally, the substrate surface may be mechanically, chemically or chemomechanically treated to reduce the incidence and/or the severity of physical and chemical defects.

In one embodiment, the substrate is treated prior to polymerization with a composition such as an acid, base, chelator or reactant that dissolves or chemically reacts with and reduces the concentration of any compositions that are included as chemical defects, or even swells the substrate allowing the particles to be released from the substrate. For example, exposed portions of barium sulfate particles may be partially or completely dissolved using a mineral or organic acid and optionally, a chelator. In one such exemplary embodiment, polyurethane comprising particles of barium sulfate may be treated with hydrochloric acid to at least partially remove exposed barium sulfate particles.

In one embodiment, the substrate is treated prior to polymerization with a surfactant to remove particles, waxes or other foreign compositions that may be on or near the surface of the substrate. Some preferred surfactants include anionic surfactants, such as alkyl sulfates: ammonium lauryl sulfate, sodium lauryl sulfate (SDS, sodium dodecyl sulfate, another name for the compound); alkyl ether sulfates: sodium laureth sulfate, also known as sodium lauryl ether sulfate (SLES), sodium myreth sulfate; sulfonates: for example docusates: dioctyl sodium sulfosuccinate; sulfonate fluorosurfactants: perfluorooctanesulfonate (PFOS), perfluorobutanesulfonate; alkyl benzene sulfonates; phosphates: for example alkyl aryl ether phosphate, alkyl ether phosphate; carboxylates: for example alkyl carboxylates: fatty acid salts (soaps): sodium stearate; sodium lauroyl sarcosinate; carboxylate fluorosurfactants: perfluorononanoate, perfluorooctanoate (PFOA or PFO). Some preferred surfactants also include cationic surfactants, such as octenidine dihydrochloride; alkyltrimethylammonium salts: cetyl trimethylammonium bromide (CTAB) a.k.a. hexadecyl trimethyl ammonium bromide, cetyl trimethylammonium chloride (CTAC); cetylpyridinium chloride (CPC); polyethoxylated tallow amine (POEA); benzalkonium chloride (BAC); benzethonium chloride (BZT); 5-bromo-5-nitro-1,3-dioxane; dimethyldioctadecylammonium chloride; dioctadecyldimethylammonium bromide (DODAB). Some preferred surfactants also include zwitterionic (amphoteric) surfactants: such as CHAPS (3-[(3-Cholamidopropyl)dimethylammonio]-1-propanesulfonate); cocamidopropyl hydroxysultaine; amino acids; Imino acids; cocamidopropyl betaine; lecithin. Some preferred surfactants also include nonionic surfactants such as fatty alcohols: cetyl alcohol, stearyl alcohol, cetostearyl alcohol (consisting predominantly of cetyl and stearyl alcohols), (O)eyl alcohol; polyoxyethylene glycol alkyl ethers (Brij): $CH_3(CH_2)_{10-16}(OC_2H_4)_{1-25}OH$:

octaethylene glycol monododecyl ether, pentaethylene glycol monododecyl ether; Polyoxypropylene glycol alkyl ethers: $CH_3(CH_2)_{10-16}(OC_3H_6)_{1-25}OH$; Glucoside alkyl ethers: $CH_3(CH_2)_{10-16}$(O-Glucoside)$_{1-3}$OH; Decyl glucoside, Lauryl glucoside, Octyl glucoside; Polyoxyethylene glycol octylphenol ethers: $C_8H_{17}(C_6H_4)(OC_2H_4)_{1-25}OH$; Triton X-100; Polyoxyethylene glycol alkylphenol ethers: $C_9H_{19}(C_6H_4)(OC_2H_4)_{1-25}OH$: Nonoxynol-9; Glycerol alkyl esters: Glyceryl laurate; Polyoxyethylene glycol sorbitan alkyl esters: Polysorbates; Sorbitan alkyl esters: Spans; Cocamide MEA, cocamide DEA; Dodecyldimethylamine oxide; Block copolymers of polyethylene glycol and polypropylene glycol: Poloxamers.

Alternatively, or additionally, the substrate may be chemically, mechanically or chemomechanically polished prior to polymerization to reduce surface roughness, reduce the incidence and/or severity of cracks, pinholes and other structural defects in the substrate surface. For example, the substrate may be solvent polished by exposing the substrate to a vapor of a solvent such as chloroform, dioxane or tetrahydrofuran. After polishing the substrate surface preferably has a global average $R_{rms}$ surface roughness that is less than the global average $R_{rms}$ surface roughness of the unpolished substrate. By way of further example, in one embodiment the polished substrate surface has a global average $R_{rms}$ surface roughness that is no more than 90% of the global average $R_{rms}$ surface roughness of the unpolished substrate surface. By way of further example, in one embodiment the polished substrate surface has a global average $R_{rms}$ surface roughness that is no more than 75% of the global average $R_{rms}$ surface roughness of the unpolished substrate surface. By way of further example, in one embodiment the polished substrate surface has a global average $R_{rms}$ surface roughness that is no more than 50% of the global average $R_{rms}$ surface roughness of the unpolished substrate surface.

Alternatively, or additionally, in one embodiment the substrate is precoated prior to polymerization with any of the compositions identified herein as a precoating or undercoating compositions to cover physical defects and/or reduce the surface roughness of the substrate surface. In general, the precoat preferably has an average thickness that equals or exceeds the global average $R_{rms}$ surface roughness of the uncoated substrate. For example, in one embodiment, the precoat has an average thickness that is at least 110% of the global average $R_{rms}$ surface roughness of the uncoated substrate. By way of further example, in one embodiment, the precoat has an average thickness that is at least 200% of the global average $R_{rms}$ surface roughness of the uncoated substrate. By way of further example, in one embodiment, the precoat has an average thickness that is at least 300% of the global average $R_{rms}$ surface roughness of the uncoated substrate. By way of further example, in one embodiment, the precoat has an average thickness that is at least 400% of the global average $R_{rms}$ surface roughness of the uncoated substrate. In addition, the precoating preferably reduces the global average $R_{rms}$ surface roughness of the substrate surface. Stated differently, the precoated substrate surface preferably has an average thickness that equals or exceeds the global average $R_{rms}$ surface roughness of the uncoated substrate and a global average $R_{rms}$ surface roughness that is less than the global average $R_{rms}$ surface roughness of the substrate prior to the application of the precoat. For example, in one embodiment the precoated substrate surface has an average thickness that is at least 110% of the global average $R_{rms}$ surface roughness of the uncoated substrate and a global average $R_{rms}$ surface roughness that is no more than 90% of the global average $R_{rms}$ surface roughness of the substrate prior to the application of the precoat. By way of further example, in one embodiment the precoated substrate surface has an average thickness that is at least 110% of the global average $R_{rms}$ surface roughness of the uncoated substrate and a global average $R_{rms}$ surface roughness that is no more than 75% of the global average $R_{rms}$ surface roughness of the substrate prior to the application of the precoat. By way of further example, in one embodiment the precoated substrate surface has an average thickness that is at least 110% of the global average $R_{rms}$ surface roughness of the uncoated substrate and a global average $R_{rms}$ surface roughness that is no more than 50% of the global average $R_{rms}$ surface roughness of the substrate prior to the application of the precoat.

Regardless of the pre-treatment steps, or even whether pre-treatment steps are employed, the surface of the substrate from which the non-fouling material is to be grafted has a global average $R_{rms}$ surface roughness that is no more than 100 nm. In certain embodiments, the surface is even smoother. For example, the surface may have a global average $R_{rms}$ surface roughness of less than 50 nm. In some embodiments, the surface may have a global average $R_{rms}$ surface roughness of less than 20 nm.

Additionally, or alternatively, and regardless of the pre-treatment steps, or even whether pre-treatment steps are employed, the surface of the substrate from which the non-fouling material is to be grafted has a visually observable surface defect density (i.e., visually observable number over a field size of 20×20 micrometers) of defects having a size (i.e., a longest dimension) greater than about 0.5 micrometers that is less than 0.1 defects/$\mu m^2$. For example, the surface of the substrate from which the non-fouling material is to be grafted may have a surface defect density of defects having a size greater than about 0.5 micrometers that is less than 0.05 defects/$\mu m^2$. By way of further example, the surface of the substrate from which the non-fouling material is to be grafted may have a surface defect density of defects having a size greater than about 0.5 micrometers that is less than 0.01 defects/$\mu m^2$. By way of further example, the surface of the substrate from which the non-fouling material is to be grafted may have a surface defect density of defects having a size greater than about 0.5 micrometers that is less than 0.002 defects/$\mu m^2$. By way of further example, the surface of the substrate from which the non-fouling material is to be grafted may have a surface defect density of defects having a size greater than about 0.5 micrometers that is less than 0.001 defects/$\mu m^2$.

In one presently preferred embodiment, the substrate is precoated with any of the precoating or undercoating materials described elsewhere herein. In one such embodiment, the precoat typically has an average thickness of at least about 100 nm. In some embodiments, the precoat will be substantially thicker; for example, the precoat may have an average thickness of as much as 500 micrometers. In general, however, the precoat will be thinner. For example, the precoat may have an average thickness of about 1-50 micrometers. By way of further example, the precoat may have an average thickness of about 10-30 micrometers.

In some instances, the substrate will have a complex shape or geometry with inner and outer surfaces to be coated. For example, multi-lumen catheters have an exterior surface and two or more longitudinal lumens that may be coated. Polymeric primer coatings may be applied by simultaneously dipping the external portion in a polymer solution or dispersion to coat the external portion and flowing a polymer solution or dispersion through the intralumenal portion to coat the intralumenal portion. Coating application parameters utilized to effect coating control include the solvent system, percent solids and viscosity, and cure temperature and time. Suitable solvents for the polymer primer layer include, but are not limited to, alcohols, such as methanol or ethanol. Application and cure temperature can vary, for example between ambient and 50° C. so as not to affect physical properties of the underlying substrate, for example, a polyurethane substrate. Solids content can vary between 0.5-10%, with solution viscosity no higher than 12 cP for ease of handling and application.

The average thickness of a polymeric surface modification or coating on a substrate can be approximated using attenuated total reflectance (ATR) infrared spectrometry if the infrared spectra and refractive indices of the typical polymeric surface material and the typical substrate material can be determined independently and if the range of the modification or coating thickness is between 10 nm and 5000 nm. A matrix of synthetic infrared absorbance spectra can be constructed using the principal component spectra (those of the coating material and the substrate material) and Beer's law ($A=\varepsilon bC$) where b, the optical pathlength, is replaced by the exponentially decaying and wavelength dependent depth of penetration of the ATR evanescent wave. An empirically measured sample is then compared across all the synthetic spectra in the matrix and the closest match, determined by the minimum n-dimensional cosine statistical distance, is the one of the sample's polymeric surface modification or coating thickness.

In one embodiment, for example, the average thickness of a homopolymeric SBMA (N-(3-sulfpropyl)-n-methacryloxyethyl-n,n-dimethylammonium betaine) hydrogel surface modification or coating on a polyetherurethane plus 10% to 50% $BaSO_4$ substrate can be determined using attenuated total reflectance (ATR) infrared spectrometry if the range of the modification or coating thickness is between 10 nm and 5000 nm and the $BaSO_4$ content of the substrate is constant to within +/−5%. The value of the absorbance of the vibrational SO3 stretch at 1037.0 $cm^{-1}$ (point baseline corrected by subtracting the absorbance value at 994.7 $cm^{-1}$) divided by the value of the absorbance of the urethane peak at 1309.5 $cm^{-1}$ (point baseline corrected by subtracting the absorbance value at 1340.0 $cm^{-1}$) equals a value relative to the concentration of SBMA present. By taking the natural log of the relative value, adding 0.1641 and then multiplying by 500 yields a value that correlates to the thickness of the homopolymeric hydrogel surface modification or coating as determined by the synthetic ATR IR matrix described above.

By way of further example, the average thickness of a homopolymeric SBMA (N-(3-sulfpropyl)-n-methacryloxyethyl-n,n-dimethylammonium betaine) hydrogel surface modification or coating on a polyetherurethane substrate can be determined using attenuated total reflectance (ATR) infrared spectrometry if the range of the modification or coating thickness is between 10 nm and 5000 nm. The value of the absorbance of the vibrational SO3 stretch at 1037.0 $cm^{-1}$ (point baseline corrected by subtracting the absorbance value at 994.7 $cm^{-1}$) divided by the value of the absorbance of the urethane peak at 1309.5 $cm^{-1}$ (point baseline corrected by subtracting the absorbance value at 1340.0 $cm^{-1}$) equals a value relative to the concentration of SBMA present. By taking the natural log of the relative value, adding 0.9899 and then multiplying by 500 yields a value that correlates to the thickness of the homopolymeric hydrogel surface modification or coating as determined by the synthetic ATR IR matrix described above.

In a preferred embodiment, some consideration is given to the combined thickness of the undercoating and the grafted polymer layer. For example, it is generally preferred that the undercoating and the grafted polymer not materially change the dimensions of the components of a devices, such as lumen diameters. Thus, in some embodiments, the combined global average dry thickness of the undercoating and the grafted polymer layer is <1% of the diameter of a catheter lumen in which it is applied. In some embodiments, the global average dry thickness of the undercoating and the grafted polymer layer is <0.5% of the diameter of a catheter lumen in which it is applied. In some embodiments, the global average dry thickness of the undercoating and the grafted polymer layer is <0.25% of the diameter of a catheter lumen in which it is applied. In further embodiments, the global average dry thickness of the undercoating and the grafted polymer layer is <0.1% of the diameter of a catheter lumen in which it is applied. In certain embodiments, the global average dry thickness of the undercoating and the grafted polymer layer is <0.05% of the diameter of a catheter lumen in which it is applied. In further embodiments, the global average dry thickness of the undercoating and the grafted polymer layer is <0.01% of the diameter of a catheter lumen in which it is applied. In further embodiments, the global average dry thickness of the undercoating and the grafted polymer layer is <0.001% of the diameter of a catheter lumen in which it is applied.

To induce small polymerization initiator molecules to concentrate at or near the substrate surface, where polymerization is initiated and propagated, polymerization mixture solvent systems with surface tensions of a magnitude differing from the surface energy of the substrate and one or more polymerization initiators having limited solubility in the polymerization mixture solvent system are selected. The surfaces of the substrate from which the non-fouling material is to be grafted surfaces may be hydrophobic or hydrophilic, and the polymerization mixture solvent system may be aqueous, comprise polar organic solvents, aqueous mixtures of polar organic solvents, or aqueous mixtures of any organic compound designed to modify the surface tension of aqueous solutions. Optionally, for hydrophobic substrates, hydrophobic initiator(s) and hydrophilic solvent systems, e.g., aqueous media are selected. Preferably, if the substrate is hydrophilic, at least one hydrophilic initiator and a non-polar organic solvent system is selected.

Preferably, the substrate (or at least the portion of the substrate into which the polymerization initiator is incorporated) is not significantly swelled by the polymerization mixture (e.g., by the polymerization mixture solvent system, the polymerization monomers, or both) and the initiator(s) incorporated into the substrate has/have limited solubility in the solvent system. As a result, the interface between substrate surface and the polymerization mixture can have a relatively high local concentration of initiator(s) to initiate non-fouling polymer growth from or near the substrate surface and to (re)initiate polymer growth from the grafted non-fouling polymer. Without being bound to any particular theory, it is presently believed that this approach leads to the grafting of a relatively highly branched non-fouling polymer from the substrate.

In a preferred embodiment, the substrate polymer from which the non-fouling polymer will be grafted will not swell more than 30% by volume at 25° C. under equilibrium conditions in the polymerization mixture solvent system. In certain embodiments, the substrate polymer from which the non-fouling polymer will be grafted will not swell more than 15% by volume at 25° C. under equilibrium conditions in the polymerization mixture solvent system. In certain embodiments, the substrate polymer from which the non-fouling polymer will be grafted will not swell more than 5% by volume at 25° C. under equilibrium conditions in the polymerization mixture solvent system. In certain embodiments, the substrate polymer from which the non-fouling polymer will be grafted will not swell or may even shrink at 25° C. under equilibrium conditions in the polymerization mixture solvent system. As previously noted, the substrate may be a composite of materials. In such instances, it is preferred that the near-surface region of the substrate into which the polymerization initiator is incorporated satisfy the swelling criteria recited herein. For example, in those embodiments in which the substrate comprises a coating of a precoat material overlying a metal, ceramic, glass or semi-metallic material, it is preferred that the coating of the precoat material not swell more than 30% by volume at 25° C. under equilibrium conditions in the polymerization mixture solvent system.

The initiator(s) incorporated into the substrate preferably have limited solubility in the solvent system comprised by the polymerization mixture and include any of the initiators identified herein. In general, it is preferred that the incorporated initiator(s) have a 10 hour T½ decomposition temperature of 25-175° C. In one particular embodiment, the incorporated initiator(s) have a 10 hour T½ decomposition temperature of 70-130° C. Advantageously, having a 10 hour T½ decomposition temperature of 70-130° C. tends to increase the density of interfacial initiation events from the redox reaction and effectively outcompete thermal initiation.

As described elsewhere herein, the initiator may comprise a redox pair; in such embodiments, at least one member of such pair have such a limited solubility in the polymerization mixture solvent system. In one embodiment, both members of the redox pair have limited solubility in the polymerization mixture solvent system. In an alternative embodiment, one member of the pair is soluble in the polymerization mixture solvent system but the other has limited solubility in the polymerization mixture solvent system. Without being bound to any particular theory, it is presently believed that when one member of a redox pair is soluble in the polymerization mixture solvent system and the other has limited solubility in the polymerization mixture solvent system, the two are phase separated and initiation is enhanced at the interface of the two phases which tends to decrease solution polymerization and increase grafting at or near the substrate surface. Thus, for example, either member of the redox pair may be hydrophobic and either member of the pair may be hydrophilic, provided at least one of the members has limited solubility in the polymerization mixture solvent system. In one preferred embodiment, a hydrophobic oxidizer is paired with a hydrophilic reducing agent. In another preferred embodiment, a hydrophilic oxidizer is paired with a hydrophobic reducing agent. For example, in one embodiment, the redox pair comprises a peroxide and a reducing agent wherein the peroxide has limited solubility in the polymerization solvent system and the reducing agent has high solubility in the polymerization solvent system. By way of further example, in certain embodiments, the peroxide has a log P partition coefficient greater than or equal to 3 for hydrophobic substrates and phases and a log P partition coefficient less than 3 for hydrophilic substrates and phases. By way of further example, in certain embodiments, the peroxide has a log P partition coefficient greater than or equal to 5 for hydrophobic substrates and phases and a log P partition coefficient less than 1 for hydrophilic substrates and phases. By way of further example, in certain embodiments, the peroxide has a log P partition coefficient greater than or equal to 7 for hydrophobic substrates and phases and a log P partition coefficient less than −1 for hydrophilic substrates and phases. By way of further example, in certain embodiments, the peroxide has a log P partition coefficient greater than or equal to 9 for hydrophobic substrates and phases and a log P partition coefficient less than −3 for hydrophilic substrates and phases.

In one embodiment, an initiator is incorporated into the substrate by initially incorporating an initiator-precursor into the substrate and activating the initiator-precursor to an initiator.

In accordance with one aspect of the present invention, the polymerization initiator(s) may be incorporated into and/or onto the substrate by various techniques. In one such method, the substrate (including substrates having precoat or undercoat as previously described) is imbibed with the polymerization initiator; that is, the polymerization initiator is absorbed into the substrate. In one embodiment, the initiator(s), i.e., an initiator or a mixture of different initiators, is introduced into and/or onto the substrate's surface by physio-adsorption, wherein the initiator is dissolved in a solvent or combination of solvents and the substrate (with or without an undercoating layer) is submerged in the mixture for a time and at a temperature to achieve sufficient absorption by the substrate. The substrate is allowed to swell ultimately imbibing initiator into the substrate. In general, the amount of initiator incorporated into a substrate during the soak will, at least in part, be a function of the, solubility of the initiator in the solvent system, solubility of the initiator in the substrate as well as the soak time, temperature and concentration of the initiator in the solution, as well as the chemical composition of the substrate and the initiator.

In a preferred embodiment, the surface of the substrate to be imbibed with the polymerization initiator(s) comprises a polymer, natural or synthetic. In an alternative embodiment, the substrate is an imbibable material selected from among polymers, natural or synthetic, biological tissues, living or dead, woven non-woven fibers, and combinations thereof. Certain (uncoated) substrates such as a metal, ceramic, glass, and semi-metallic substrates lack the capacity to absorb sufficient initiator. In general, therefore, for these substrates it is preferred to precoat the surface of the metal, ceramic, glass or semi-metallic substrate with an undercoating or precoating, from which the polymeric material may be grafted. For example, metal, ceramic, glass, and semi-metallic substrates may be precoated with a polymer selected from polyamide, polyamine, polyanhydride, polyazine, poly(carbonate), polyester, polyether, polyetheretherketone (PEEK), polyguanidine, polyimide, polyketal, poly(ketone), polyolefin, poly(orthoester), polyphosphazine, polysaccharide, polysiloxane, polysulfone, polyurea, polyurethane, halogenated polymer, silicone, aldehyde cross-linked resin, epoxy resin, phenolic resin, latex, or a copolymer or blend thereof, and the precoated substrate is then imbibed as previously described.

The quantity of initiator introduced to the substrate can be controlled by changing the concentration of the initiator in the solvent solution and/or by changing the amount of time the substrate is allowed to soak in the initiator solution during one initiator imbibing period or by repeating any number of initiator imbibing periods as required. Temperature is not narrowly critical, with temperatures in the range of room temperature to elevated temperatures being typical. When utilizing multiple periods of initiator imbibing, the initiator used in the subsequent imbibing periods can be the same as, different from, or a mixture with the initiator used in the previous initiator imbibing period. In general, the substrate is immersed in the initiator-containing solution for at least several seconds before polymerization is initiated. In some embodiments, the substrate is immersed in the initiator-containing solution for longer times. For example, the substrate may be immersed in the initiator-containing solution for at least several minutes. By way of further example, the substrate may be immersed in the initiator-containing solution for at least about 15 minutes before polymerization is initiated. In some embodiments, the substrate will be immersed in the initiator-containing solution for at least 1 hour at room temperature or elevated temperatures for initiators having a 10 hour T½ decomposition temperature of 70-130° C. before polymerization is initiated. In further embodiments, the substrate will be immersed in the initiator-containing solution for at least 2 hour before polymerization is initiated. In yet further embodiments, the substrate will be immersed in the initiator-containing solution for at least 16 hour before polymerization is initiated. Depending upon the time, temperature and concentration of initiator in the initiator-containing solution, a concentration gradient of initiator in the substrate may be established. In some embodiments, it may be preferable to have a higher concentration of initiator in the substrate nearer to the surface. As noted, the initiator may be present in a range of concentrations in the initiator-containing solution. In general, the concentration of the initiator in the initiator-containing solution will be at least 0.01% by weight. For example, in some embodiments, the concentration of the initiator will generally be at least 0.1% by weight. In some embodiments, the concentration will be even greater, e.g., at least 0.5% by weight. In some embodiments, the concentration will be even greater, e.g., at least 1% by weight. In some embodiments, the concentration will be even greater, e.g., at least 10% by weight. In certain exemplary embodiments, the concentration of the initiator in the initiator-containing solution will be in the range of about 0.2 to about 1% by weight. In certain exemplary embodiments, the concentration of the initiator in the initiator-containing solution will be in the range of about 0.2 to about 10% by weight. In certain exemplary embodiments, the concentration of the initiator in the initiator-containing solution will be in the range of about 0.5 to about 5% by weight. In certain exemplary embodiments, the concentration of the initiator in the initiator-containing solution will be in the range of about 0.75 to about 3% by weight. In each of these embodiments, the initiator is preferably one of the UV, thermal or redox initiators described elsewhere herein.

As a result of the imbibing process, the imbibed substrate may contain about 0.001% by weight initiator. In some embodiments, the imbibed substrate will contain greater amounts of initiator, e.g., at least about 0.01% by weight. For example, in some embodiments the imbibed substrate will contain at least about 0.1% by weight. By way of further example, in some embodiments the imbibed substrate will contain about 0.05% to about 2% by weight initiator. By way of further example, in some embodiments the imbibed substrate will contain about 0.1% to about 1% by weight initiator. By way of further example, in some embodiments the imbibed substrate will contain about 0.2% to about 0.5% by weight initiator. By way of further example, in some embodiments the imbibed substrate will contain about 1% to about 10% by weight initiator. Typically, however, the imbibed substrate will contain less than about 20% by weight initiator. In each of these embodiments, the initiator is preferably one of the UV, thermal or redox initiators described elsewhere herein. The solvent used to imbibe the substrate with initiator may have the capacity to swell the substrate (or at least the portion of the substrate to be imbibed with initiator) to various degrees. Typically, the imbibing solvent has a capacity to swell the substrate (or at least the portion of the substrate to be imbibed with initiator) less than 900% by volume at room temperature and ambient pressure. For example, in one such embodiment, the imbibing solvent has a capacity to swell the substrate (or at least the portion of the substrate to be imbibed with initiator) less than 750% by volume. By way of further example, in one such embodiment, the imbibing solvent has a capacity to swell the substrate (or at least the portion of the substrate to be imbibed with initiator) less than 500% by volume. By way of further example, in one such embodiment, the imbibing solvent has a capacity to swell the substrate (or at least the portion of the substrate to be imbibed with initiator) less than 250% by volume. By way of further example, in one such embodiment, the imbibing solvent has a capacity to swell the substrate (or at least the portion of the substrate to be imbibed with initiator) less than 100% by volume. By way of further example, in one such embodiment, the imbibing solvent has a capacity to swell the substrate (or at least the portion of the substrate to be imbibed with initiator) less than 100% by volume. By way of further example, in one such embodiment, the imbibing solvent has a capacity to swell the substrate (or at least the portion of the substrate to be imbibed with initiator) less than 25% by volume.

In a preferred embodiment, the imbibed substrate is preferably washed using a solvent, optionally with a solvent that swells that substrate, and optionally dried. In other embodiments, the substrate is washed with solvents, which may be the same or different from the imbibing solvents, or the substrate may not be washed. For example, the wash solvent may swell the substrate, shrink the substrate, or neither. In one embodiment, the substrate is dried, partially dried or not dried. Optionally, there may be a solvent exchange.

In an alternative method, the initiator(s) is/are incorporated into the substrate by co-deposition of the initiator(s) as a component of a coating, i.e., a precoating or undercoating as described herein, on the surface of the substrate. For example, a thin film of polymer and initiator are deposited onto the substrate by dipping the substrate in a solution of initiator(s) and polymer. Alternatively, a precoat layer of a flowable mixture of the initiator(s) and a second material such as a polymeric material are deposited onto the surface of the substrate. The precoating may thus be applied to any of the substrates described herein, including metals, ceramics, glasses, polymers, biological tissues, living or dead, woven and non-woven fibers, semi-metals such as silicon. For example, the metal, ceramic, glass, polymer, biological tissue, fiber, or semi-metal may be precoated with a polymer and initiator mixture wherein the polymer is selected from polyamide, polyamine, polyanhydride, polyazine, poly(carbonate), polyester, polyether, polyetheretherketone (PEEK), polyguanidine, polyimide, polyketal, poly(ketone), polyolefin, poly(orthoester), polyphosphazine, polysaccharide, polysiloxane, polysulfone, polyurea, polyurethane, halogenated polymer, silicone, aldehyde crosslinked resin, epoxy resin, phenolic resin, latex, or a copolymer or blend thereof.

In one embodiment, the amount of initiator co-deposited with the polymer is relatively great. In certain embodiments, for example, the weight ratio of initiator to polymer co-deposited will be at least 1:1000, respectively. In some embodiments, the weight ratio of initiator to polymer co-deposited will be even greater, e.g., at least 1:100, 1:10, 1:1, 10:1, 100:1, or 1000:1 respectively. Typically, the ratio of initiator to polymer will be in the range of about 1:1 to about 20:1. In addition, the co-deposited layers (i.e., the layers containing co-deposited initiator and polymer) will have a thickness of at least 100 nm. For example, in one embodiment, the co-deposited layer will have a thickness of about 100 nm to about 500 micrometers. In each of these embodiments, the initiator is preferably one of the UV, thermal or redox initiators described elsewhere herein.

In certain preferred embodiments, the co-deposited layer will contain, as the co-deposited polymer, polyurethane, polystyrene, polyester, sol-gels, or a combination thereof. Thus, for example, in one embodiment, the co-deposited layer will have a thickness of about 100 nm to about 50 micrometers, and the weight ratio of initiator to polymer in the co-deposited layer will be at least 1:1000, respectively. In certain more specific embodiments, the co-deposited layer will contain polyurethane as the co-deposited polymer, will have a thickness of about 1-50 micrometers. By way of further example, the co-deposited layer may have an average thickness of about 10-30 micrometers. By way of further example, in each of these exemplary embodiments the co-deposited layer may have a weight ratio of initiator to polymer of about 1:1,000 to about 20:1, respectively. In addition, in each of these exemplary embodiments, the initiator is preferably one of the UV, thermal or redox initiators described elsewhere herein.

The solvent and/or solvent mixtures used to co-deposit the initiator(s) and the polymer as a precoat may have the capacity to swell the substrate to various degrees. Typically, the co-deposition solvent swells the substrate (or at least the portion of the substrate to be imbibed with initiator) less than 900% by volume at room temperature and ambient pressure. For example, in one such embodiment, the co-deposition solvent swells the substrate (or at least the portion of the substrate to be imbibed with initiator) less than 100% by volume. By way of further example, in one such embodiment, the co-deposition solvent swells the substrate (or at least the portion of the substrate to be imbibed with initiator) less than 100% by volume. By way of further example, in one such embodiment, the co-deposition solvent swells the substrate (or at least the portion of the substrate to be imbibed with initiator) less than 25% by volume. In a preferred embodiment, the co-deposited layer is preferably washed using a solvent and/or solvent mixture, optionally with a solvent that swells that substrate, and optionally dried. Alternatively, the co-deposited layer is preferably washed using a solvent and/or solvent mixture, optionally with a solvent and/or solvent mixture that has limited swelling of the substrate, and optionally dried. Alternatively, the co-deposited layer is not washed using a solvent and optionally dried.

In one exemplary embodiment, a solution containing 1% to 5% (wt/wt) urethane can be prepared by dissolving the appropriate weight of urethane pellets in a suitable organic solvent, such as tetrahydrofuran, and diluting the solution with a second solvent, such as methanol. The final methanol concentration is preferably between 10%-90%, more preferably between 15%-85%, most preferably 60%. One or more suitable initiator molecules, such as benzoyl peroxide or dicumyl peroxide, are added to the polymer solution at a concentration typically from about 0.25% to about 10%. However, concentrations below 0.25% and above 10% can be used. Any desired substrate can be exposed to the polymer/initiator solution once or multiple times until a desired coating thickness and/or initiator surface concentration has been achieved. The solvent is typically removed, for example by evaporation, from the coated substrate between each exposure to the solution, in a case where the substrate is exposed multiple times. After the final exposure, the substrate is optionally allowed to sit for at least 10 minutes to allow any residual solvent to evaporate, prior to placing in a polymerization reaction mixture.

In another alternative method, the initiator(s) is/are incorporated into and/or onto the substrate by means of a aerosol deposition or spray coating process. The initiator(s) is/are mixed with a monosolvent, co-solvent, or mixed solvent system and applied to the substrate surface by means of a directed, charged or non-charged aerosol deposition method. For example, the initiator(s) is/are mixed with organic solvent mixture and deposited onto the substrate surface as an aerosol by means of a compressed air spray. The amount of initiator physio-adsorbed into and/or onto the surface of the substrate can be controlled by varying the amount of time the aerosol stays on the surface of substrate before the solvent evaporates and thus affecting the amount of initiator absorbed into the bulk of the substrate (e.g., the longer the dwell time on the surface the more initiator can move into the substrate bulk and visa versa). The dwell time of the aerosol on the substrate can be controlled by varying the boiling point of the aerosol which is done by varying the proportion of low and high boiling point solvents in the solvent system. Additionally, the amount of initiator applied onto and/or into the substrate can be controlled by varying the aerosol flow rate, aerosol gas mixture, aerosol droplet size, aerosol charge, substrate charge, aerosol deposition environment (temperature, pressure, and/or atmosphere), and the amount of aerosol applied. The aerosol deposition may be applied to any of the substrates described herein, including metals, ceramics, glasses, polymers, biological tissues, living or dead, woven and non-woven fibers, semimetals such as silicon.

Regardless of the method of incorporation, initiator is incorporated into the substrate by imbibing the substrate or depositing a coating containing the initiator onto the substrate. The incorporated initiator may comprise one initiator species, or more than one initiator species. For example, one or more species of ultraviolet (UV) initiators, one or more species of thermal initiators, and/or one or more species of redox initiators may be incorporated into the substrate. More specifically, in one presently preferred embodiment, the initiator(s) are/is incorporated into the near-surface zone between its upper and lower boundaries as described elsewhere herein. Based upon experimental evidence to date, and without being bound to any particular theory, it appears that the incorporated initiator permits a grafting of the polymeric material from within the near-surface zone as well as the substrate surface.

Regardless of the theory, it is generally preferred that the amount of initiator incorporated into the substrate be sufficient to enable its detection in the substrate, prior to polymerization, and detection of it or a degradation product thereof in the substrate post-polymerization. In general, extractions can use both nonpolar and polar solvents. For example, extraction solvents such as water, acetone or ethanol; and/or other extraction solvents in which the solubility of the initiator and/or its degradation products is at least 1 mg/L. The extraction should be carried out for a sufficient time such that the change in concentration of the extract is not increasing more than 5% per hour. Alternatively, extraction until the amount of extracted material in a subsequent extraction is less than 10% of that detected in the initial extraction, or until there is no analytically significant increase in the cumulative extracted material levels detected. Exemplary extraction conditions include: 37° C. for 72 h; 50° C. for 72 h; 70° C. for 24 h; and 121° C. for 1 h.

Exemplary extraction ratio includes 6 cm²/mL surface area/volume and/or 0.2 g sample/mL. In some instances, complete dissolution of the substrate may be appropriate. Materials shall be cut into small pieces before extraction to enhance submersion in the extract media, for example, for polymeric substrates approximately 10 mm×50 mm or 5 mm×25 mm are appropriate.

Examples of the instrumentation used for analysis includes high-performance liquid chromatography-photodiode array detection-mass spectrometry (HPLC-PDA-MS) for organics analysis; gas chromatography-mass spectrometry (GC-MS) for organics analysis; inductively coupled plasma-optical emission spectroscopy or mass spectrometry (ICP-OES or ICP-MS) for metals analysis; and ion chromatography (IC) for inorganics and ion analysis. More advanced MS detectors such as time-of-flight (TOF) can also be used to obtain accurate mass information. Hexane and alcohol extractions are analyzed, for example by GC-MS and HPLC. Water and alcohol extractions are analyzed, for example by HPLC.

The initiator or its degradation products may be quantified and/or detected in the substrate or grafted polymer by the previously described methods. These include FTIR-ATR, electron spectroscopy for chemical analysis (ESCA, also called X-ray photoelectron spectroscopy, XPS), Secondary Ion Mass Spectrometry (SIMS), and surface-enhanced Raman spectroscopy (SERS). For example, peroxide may be detected spectrophotometically using any of the following three methods: the iodide method (oxidation of sodium iodide by peroxides in the presence of ferric chloride), the DPPH method (treatment with 1,1-diphenyl-2-picrylhydrazyl, a radical scavenger, to decompose the peroxides), or the peroxidase method (reduction with glutathione, catalyzed by glutathione peroxidase, followed by measuring the coupled oxidation of NADPH in the presence of glutathione reductase). See, for example, Fujimoto et al., Journal of Polymer Science Part A: Polymer Chemistry, Vol. 31, 1035-1043 (1993).

Similarly, the initiator(s) and/or the degradation products thereof may also be extracted from the substrate/grafted polymer using a suitable solvent such as water, acetone or ethanol and quantified and/or detected in the substrate or grafted polymer by the previously described methods. These include FTIR-ATR, electron spectroscopy for chemical analysis (ESCA, also called X-ray photoelectron spectroscopy, XPS), Secondary Ion Mass Spectrometry (SIMS), and surface-enhanced Raman spectroscopy (SERS). For example, peroxide may be detected spectrophotometically using any of the following three methods: the iodide method (oxidation of sodium iodide by peroxides in the presence of ferric chloride), the DPPH method (treatment with 1,1-diphenyl-2-picrylhydrazyl, a radical scavenger, to decompose the peroxides), or the peroxidase method (reduction with glutathione, catalyzed by glutathione peroxidase, followed by measuring the coupled oxidation of NADPH in the presence of glutathione reductase). See, for example, Fujimoto et al., Journal of Polymer Science Part A: Polymer Chemistry, Vol. 31, 1035-1043 (1993).

In another embodiment, quantification and/or detection of the initiator in the substrate pre-polymerization, or quantification and/or detection of the initiator or its degradation product(s) in the substrate post-polymerization may be accomplished by extraction followed by any of a range of analytical techniques. For example, quantifying and/or detecting the amount of initiator or its degradation product(s) in the extract can be accomplished using spectroscopy and chromatography; including, UV/VIS, FTIR, nuclear magnetic spectroscopy, thin layer chromatography, gas chromatography, and liquid chromatography.

Monomers can be selected such that their reactivity ratios give alternating copolymers, periodic copolymers with a pre-specified ratio of each monomer, random copolymers, block copolymers or homopolymers. Inclusion of more than two reactive groups on each monomer unit allows for the formation of star polymers, dendrimers, regularly branched polymers, randomly branched polymers, and brush polymers. In general, the monomer may be selected from any of the monomers disclosed herein. Thus, for example, the monomers may contain any of the pendant groups corresponding to Formulae ZI-1 to ZI-7. By way of further example, upon polymerization the monomers may provide the polymer with repeat units corresponding to any of Formula 1-12. In a preferred embodiment, the monomers are miscible with the polymerization mixture solvent system.

In processes for modification of the surface of a hydrophobic substrate, a hydrophilic solvent system preferably is employed. Aqueous solutions preferably are used as the solvent system, optionally containing ions or buffers, such as sodium, ammonium, potassium, chloride, phosphate, or acetate. In processes for modifying hydrophilic substrates, a hydrophobic solvent system preferably is used. In such processes, the preferred media is an organic solvent, typically a non-polar organic solvent, or a mixture thereof. Exemplary organic solvents include one or more of toluene, hexane, cyclohexane, benzene, xylene, tetrahydrofuran, and aliphatic alcohols. In a preferred embodiment, the solvent system does not swell the substrate (or at least that portion of the substrate from which the polymer will be grafted) by more than 25% by volume. For example, in one such embodiment, the solvent system does not swell the substrate (or at least that portion of the substrate from which the polymer will be grafted) by more than 10% by volume. In a preferred embodiment, the solvent system does not swell the substrate (or at least that portion of the substrate from which the polymer will be grafted) by more than 5% by volume. In one embodiment, the solvent system may even shrink the substrate (or at least that portion of the substrate from which the polymer will be grafted).

In one particularly preferred embodiment, the non-fouling polymeric materials are grafted from the substrate by chain growth addition polymerization. The polymerization conditions described herein are generally mild compared to other methods of polymerization and thus do not significantly alter the mechanical properties, flexibility, or dimensional properties of the underlying substrate. In one preferred embodiment, for example, polymerization is carried out at a temperature not in excess of 60° C. The polymerization may be carried out over a relatively wide pH range, e.g., about 0-10. In one embodiment, the polymerization reaction is carried out at a pH of about 2-8. For example, when DCP and ferrous gluconate are used as redox pair, the polymerization reaction may be carried out at a pH of about 6-8. By way of further example, when benzoyl peroxide and ferrous gluconate are used as redox pair, the polymerization reaction may be carried out at a pH of about 4-6. By way of further example, when O,O-t-Butyl-O-(2-ethylhexyl) mono-peroxycarbonate ("TBEC") and ferrous gluconate are used as redox pair, the polymerization reaction may be carried out at a pH of about 5-7.

Examples of radical polymerization processes include, but are not limited to, UV, thermal, and redox initiated processes. In particular embodiments, the polymer is grafted from the substrate, by first incorporating one or more initiators, such as an ultraviolet (UV), thermal, or redox initiator into the substrate and initiating polymerization of one or more monomers from the surface. Preferably, the initiator is incorporated into the substrate by imbibing the substrate with initiator or coating the substrate with a layer, e.g., an undercoating layer (sometimes referred to herein as the co-deposited layer), comprising the initiator. The polymerization is typically initiated by exposing the initiator-imbibed substrate with a solution or suspension of the monomer or monomers to be polymerized. The quantity of polymer introduced to the substrate can be controlled by changing the concentration of the polymer in the solvent solution, surface tension of the polymer solution, polymerization temperature, pH of the polymer solution, polymerization solution agitation or flow conditions, by changing the amount of time the substrate is allowed to be in the polymer solution during one polymerization period, and/or by repeating any number of polymerization periods as required. When utilizing multiple polymerization periods, the polymer(s) used in the subsequent polymerization periods can be the same as, different from, or a mixture with the polymer(s) used in the previous polymerization period.

Chain transfer agents can be added to the monomer solution to mediate the graft-from radical polymerization reaction kinetics. Chain transfer agents include, but are not limited to, molecules containing halocarbons, thiols, dithiocarbamates, trithiocarbonates, dithioesters, xanthates, primary or secondary alcohols. Examples of chain transfer agents are bromotrichloromethane, 4-methylbenzenethiol, benzyl alcohol, methanol, ethanol, ethyleneglycol, glycerol, and isopropanol. In one embodiment the radical polymerization graftings are mediated using 2,2,6,6-tetramethylpiperidinie-1-oxyl (TEMPO). In one embodiment the radical polymerization graftings are mediated using reversible addition fragmentation transfer (RAFT) agents. Examples of RAFT agents include 2-(Dodecylthiocarbonothioylthio)-2-methylpropionic acid, 2-Cyano-2-propyl benzodithioate, 2-Cyano-2-propyl dodecyl trithiocarbonate, 4-Cyano-4-(phenylcarbonothioylthio)pentanoic acid, 4-Cyano-4-[(dodecylsulfanylthiocarbonyl)sulfanyl]pentanoic acid, Bis(dodecylsulfanylthiocarbonyl) disulfide, Bis(thiobenzoyl) disulfide, Cyanomethyl dodecyl trithiocarbonate, Cyanomethyl methyl(phenyl)carbamodithioate, and their analogues and derivatives Oxygen can act as an inhibitor in free radical polymerization as it can react quickly with the free radicals generated by the initiator to form stable radical species, which in turn can react with other radical species to form unreactive species which terminate the polymerization. Therefore, creating an oxygen-free environment by degassing with nitrogen or argon or vacuum is typically used to remove oxygen before and during polymerization. However, for certain embodiments, it would preferable not to require such degassing steps in commercial production. In one preferred embodiment, the polymerization method is other than ATRP, which typically requires stringent control of oxygen levels that may be difficult to achieve during manufacturing.

Alternatively, oxygen in the system can be minimized by filling the reactor with the reaction mixtures thus physically displacing the oxygen in the reactor. In another embodiment, reagents which scavenge oxygen can be added to the reaction mixture. Suitable oxygen-scavenging reagents include, but are not limited to, sodium (meta) periodate, riboflavin, and ascorbic acid. These agents may improve the efficacy of the resulting polymer if the polymerization does not employ an inert atmosphere.

In addition to monomer and a solvent system, the polymerization mixture may optionally contain a free radical inhibitor to encourage surface grafting. Without being bound to any particular theory, it is presently believed that the addition of a free radical inhibitor, including, hydroquinone, hydroquinone monomethyl ether, phenothiazine, 3,7-bis(dimethylamino)phenazathionium chloride, triethylene diamine, t-butylcatechol, butylated hydroxytoluene, and 4-t-butylphenol to the grafting solution decreases solution polymerization, thereby allowing more monomer to be available for grafting at or near the substrate surface/polymerization mixture interface.

Plasticizers can be incorporated into the grafted polymer at any time during and/or subsequent to surface polymerization. In the preferred embodiment, a hydrophilic plasticizer (such as citrated esters, ethylene glycol, propylene glycol, and/or polyethylene glycol [<2000 $M_w$]) is incorporated into the grafted polymer in a post-polymerization aqueous wash period.

i. UV Initiators

In one embodiment, the initiator is an ultraviolet (UV) initiator. The substrate and initiator are typically placed into an aqueous, degassed, solution containing a zwitterionic monomer and exposed to UV light, initiating the radical polymerization. In one exemplary embodiment, the UV light has a peak wavelength of 365 nm, generated by a 100 W UV.

Examples of UV radical initiators include, but are not limited to, 1-Hydroxycyclohexyl phenyl ketone, 2,2-Diethoxyacetophenone, 2-Benzyl-2-(dimethylamino)-4'-morpholinobutyrophenone, 2-Hydroxy-2-methylpropiophenone, 2-Hydroxy-4'-(2-hydroxyethoxy)-2-methylpropiophenone, 2-Methyl-4'-(methylthio)-2-morpholinopropiophenone, 3'-Hydroxyacetophenone, 4'-Ethoxyacetophenone, 4'-Hydroxyacetophenone, 4'-Phenoxyacetophenone, 4'-tert-Butyl-2',6'-dimethylacetophenone, Diphenyl(2,4,6-trimethylbenzoyl)phosphine oxide/2-hydroxy-2-methylpropiophenone, 2,2-Dimethoxy-2-phenylacetophenone, 4,4'-Dimethoxybenzoin, 4,4'-Dimethylbenzil, Benzoin ethyl ether, Benzoin isobutyl ether, Benzoin methyl ether, Benzoin, 2-Methylbenzophenone, 3,4-Dimethylbenzophenone, 3-Hydroxybenzophenone, 3-Methylbenzophenone, 4,4'-Bis(diethylamino)benzophenone, 4,4'-Dihydroxybenzophenone, 4,4'-Bis[2-(1-propenyl)phenoxy]benzophenone, 4-(Diethylamino)benzophenone, 4-Benzoylbiphenyl, 4-Hydroxybenzophenone, 4-Methylbenzophenone, Benzophenone-3,3',4,4'-tetracarboxylic dianhydride, Benzophenone, Methyl benzoylformate, Michler's ketone, Sulfoniums, iodiums, 2-(4-Methoxystyryl)-4,6-bis(trichloromethyl)-1,3,5-triazine, Diphenyliodonium p-toluenesulfonate, N-Hydroxy-5-norbornene-2,3-dicarboximide perfluoro-1-butanesulfonate, N-Hydroxynaphthalimide triflate, 2-tert-Butylanthraquinone, 9,10-Phenanthrenequinone, Anthraquinone-2-sulfonic acid sodium salt monohydrate, Camphorquinone, Diphenyl (2,4,6-trimethylbenzoyl)phosphine oxide, 10-Methylphenothiazine, thioxanthones, and IRGRCURE 2959.

ii. Thermal Initiators

In another embodiment a heat activated (thermal) initiator is used, in place of the UV initiator described above, and the graft-from polymerization is initiated by heating the aqueous monomer solution temperature to a desired temperature and holding the temperature constant until the desired degree of polymerization is achieved.

Suitable thermal initiators include, but are not limited to, tert-Amyl peroxybenzoate, 4,4-Azobis(4-cyanovaleric acid), 2,2'-Azobis[(2-carboxyethyl)-2-methylpropionamidine], 2,2'-Azobis(4-methoxy-2,3,-dimethylvaleronitrile), 1,1'-Azobis(cyclohexanecarbonitrile), 2,2'-Azobisisobutyronitrile (AIBN), Benzoyl peroxide, 2,2-Bis(tert-butylperoxy)butane, 1,1-Bis(tert-butylperoxy)cyclohexane, 2,5-Bis(tert-butylperoxy)-2,5-dimethylhexane, 2,5-Bis(tert-Butylperoxy)-2,5-dimethyl-3-hexyne, Bis(1-(tert-butylperoxy)-1-methylethyl)benzene, 1,1-Bis(tert-butylperoxy)-3,3,5-trimethylcyclohexane, tert-Butyl hydroperoxide, tert-Butyl peracetate, tert-Butyl peroxide, tert-Butyl peroxybenzoate, tert-Butylperoxy isopropyl carbonate, Cumene hydroperoxide, Cyclohexanone peroxide, Dicumyl peroxide, Lauroyl peroxide, 2,4-Pentanedione peroxide, Peracetic acid, Potassium persulfate.

The temperature to which the solution is heated is dependent, among other things, on the monomer and/or the initiator, and/or the substrate. Examples of thermal radical initiators include, but are not limited to, azo-compounds such as azobisisobutyronitrile (AIBN) and 1,1'-Azobis(cyclohexanecarbonitrile) (ABCN). Preferable grafting temperatures are near the 10 hour T½ of the initiator selected. The graft-from radical polymerization reaction can be thermally quenched by heating beyond the initiators half life.

iii. Redox Initiators

In another embodiment, a redox initiator system is used to initiate polymerization from the surface of the substrate. The redox initiator system typically includes a pair of initiators: an oxidant and a reducing agent. The redox chemistry described herein can be modified to prepare non-fouling polymeric materials, for example, such as zwitterionic polymeric materials. Redox initiation is regarded as a one-electron transfer reaction to effectively generate free radicals under mild conditions. Suitable oxidants include, but are not limited to, peroxide, hydroperoxide, persulfates, peroxycarbonates, peroxydisulfates, peroxydiphosphate, permanganate, salts of metals such as Mn(III), Ce(IV), V(V), Co(III), Cr(VI) and Fe(III).

Suitable reducing agents include, but are not limited to, metal salts such as Fe(II), Cr(II), V(II), Ti(III), Cu(II), and Ag(I) salts, and oxyacids of sulfur, hydroxyacids, alcohols, thiols, ketones, aldehydes, amine, and amides. For example, in some embodiments, the reducing agent is an iron(II) salt, such as iron(II) L-ascorbate, ferrous sulfate, iron(II) acetate, iron(II) acetylacetonate, iron(II) ethylenediammonium sulfate, iron(II) gluconate, iron(II) lactate, iron(II) oxalate, or iron(II) sulfate.

Polymerization can be initiated by radicals formed directly from the redox reaction and/or by macroradicals formed by the abstraction of a hydrogen atom from the substrate by the transient radicals formed during the redox reaction.

In one embodiment, the substrate is coated with a undercoating coating and the non-fouling material is grafted from the undercoating layer by redox polymerization. The undercoating coating contains oxidants or reducing agents. In a preferred embodiment, the undercoating layer contains one or more reducing agents, such as acids, alcohol, thiols, ketones, aldehydes, amines and amides. An oxidant is used to react with one or more functional groups of the undercoating layer to form radicals which initiate the graft-from polymerization.

In a particular embodiment, the undercoating layer is a copolymer with pendant groups of aliphatic chains containing silanol and/or hydroxyl groups. Such materials can be used to form a undercoating layer on polymeric substrates, such as polyurethane (PU). An oxidant, such as a salt of Ce(IV), reacts with the hydroxyl group under mild conditions to form hydroxyl radicals in the undercoating layer to grow the zwitterionic polymers.

In still another embodiment, a pair of peroxides and metal salts (such as Fe(II) as used in the Fenton Reaction) is used in the redox polymerization to graft zwitterionic polymers from polymers such as polyurethane. Peroxides for use in the redox polymerization include diacyl peroxides, dialkyl peroxides, diperoxyketals, hydroperoxides, ketone peroxides, peroxydicarbonates, and peroxyesters. Exemplary diacyl peroxides include decanoyl peroxide, lauroyl peroxide, succinic acid peroxide, and benzoyl peroxide, Exemplary dialkyl peroxides include dicumyl peroxide, 2,5-di(t-butylperoxy)-2,5-dimethylhexane, t-butyl cumyl peroxide, a,a'-bis(t-butylperoxy)diisopropylbenzene mixture of isomers, di(t-amyl) peroxide, di(t-butyl) peroxide and 2,5-di(t-butylperoxy)-2,5-dimethyl-3-hexyne. Exemplary diperoxyketals include 1,1-di(t-butylperoxy)-3,3,5-trimethylcyclohexane, 1,1-di(t-butylperoxy)cyclohexane, 1,1-di(t-amylperoxy)cyclohexane, n-butyl 4,4-di(t-butylperoxy)valerate, ethyl 3,3-di-(t-amylperoxy)butanoate and ethyl 3,3-di-(t-butylperoxy)butyrate. Exemplary hydroperoxides include cumene hydroperoxide and t-butyl hydroperoxide. Exemplary ketone peroxides include methyl ethyl ketone peroxide mixture and 2,4-pentanedione peroxide. Exemplary peroxydicarbonates include di(n-propyl)peroxydicarbonate, di(sec-butyl)peroxydicarbonate, and di(2-ethylhexyl)peroxydicarbonate. Exemplary peroxyesters include 3-hydroxy-1,1-dimethylbutyl peroxyneodecanoate alpha-cumyl peroxyneodecanoate, t-amyl peroxyneodecanoate, t-butyl peroxyneodecanoate, t-amyl peroxypivalate, t-butyl peroxypivalate, 2,5-di(2-ethylhexanoylperoxy)-2,5-dimethylhexane, t-amyl peroxy-2-ethylhexanoate, t-butyl peroxy-2-ethyl hexanoate, t-amyl peroxyacetate, t-butyl peroxyacetate, t-butyl peroxyacetate, t-butyl peroxybenzoate, OO-(t-amyl) O-(2-ethylhexyl) monoperoxycarbonate, OO-(t-butyl)-O-isopropyl monoperoxycarbonate, OO-(t-butyl)-O-(2-ethylhexyl) monoperoxycarbonate, polyether poly-t-butylperoxy carbonate, and t-butyl peroxy-3,5,5-trimethylhexanoate.

Any of the aforementioned peroxides such as benzoyl peroxide, lauroyl peroxide, hydrogen peroxide, or dicumyl peroxide are imbibed into the polymer such as polyurethane by dipping the polymer into a peroxide solution in an organic solvent for a predetermined period of time and dried. The peroxide containing polymer is put into a solution of monomer. The redox polymerization is initiated by the addition of a reducing agent, for example salts of Fe(II), such as Fe(II) chloride, Fe(II) sulfate, ammonium Fe(II) sulfate, or Fe(II) gluconate, at room temperature or elevated temperature, to the monomer solution.

For modifying the surface of an article and/or surface graft polymerization, it has been found particularly useful to use hydrophobic-hydrophilic redox initiator pairs. For example, in one embodiment the hydrophobic member of a hydrophobic-hydrophilic redox initiator pair is incorporated into a hydrophobic substrate as previously described. The substrate surface is then treated with an aqueous polymerization mixture containing monomers, typically hydrophilic monomers, and the hydrophilic member of the redox pair. This method offers particular advantages when polymers are being grafted from components having exposed external and internal surfaces to be modified (such as catheters) and any substrate that cannot readily be exposed to light. Additionally, such a system tends to minimize the extent of non graft polymerization in the bulk polymerization mixture away from the polymerization mixture/substrate surface interface.

In a preferred embodiment, the hydrophilic-hydrophobic redox pair is a hydrophobic oxidizing agent/hydrophilic reducing agent pair wherein (i) the hydrophobic oxidizing agent is tert-amyl peroxybenzoate, O,O-t-Butyl-O-(2-ethylhexyl) mono-peroxycarbonate, benzoyl peroxide, 2,2-bis(tert-butylperoxy)butane, 1,1-bis(tert-butylperoxy)cyclohexane, 2,5-bis(tert-butylperoxy)-2,5-dimethylhexane, 2,5-Bis(tert-Butylperoxy)-2,5-dimethyl-3-hexyne, bis(1-(tert-butylperoxy)-1-methylethyl)benzene, 1,1-bis(tert-butylperoxy)-3,3,5-trimethylcyclohexane, tert-butyl hydroperoxide, tert-butyl peracetate, tert-butyl peroxide, tert-butyl peroxybenzoate, tert-butylperoxy isopropyl carbonate, cumene hydroperoxide, cyclohexanone peroxide, dicumyl peroxide, lauroyl peroxide, 2,4-pentanedione peroxide, 4,4-azobis(4-cyanovaleric acid), or 1,1'-Azobis(cyclohexanecarbonitrile), 2,2'-Azobisisobutyronitrile (AIBN) and (ii) the hydrophilic reducing agent is $Fe^{2+}$, $Cr^{2+}$, $V^{2+}$, $Ti^{3+}$, $Co^{2+}$, $Cu^+$, or an amine; transition metal ion complexes, e.g., copper (II) acetylacetonate, $HSO_3^-$, $SO_3^{2-}$, $S_2O_3^{2-}$, or $S_2O_5^{2}$. Exemplary combinations include any of the aforementioned peroxides and $Fe^{2+}$. In some preferred embodiments, benzoyl peroxide, dicumyl peroxide, or O,O-t-Butyl-O-(2-ethylhexyl) mono-peroxycarbonate are used in combination with $Fe^{2+}$.

In an alternative embodiment, the hydrophilic-hydrophobic redox pair is a hydrophilic oxidizing agent/hydrophobic reducing agent pair wherein (i) the hydrophilic oxidizing agent is peracetic acid, a persulfate such as potassium persulfate, $Fe^{3+}$, $ClO^{3-}$, $H_2O_2$, $Ce^{4+}$, $V^{5+}$, $Cr^{6+}$, or $Mn^{3+}$, or their combinations; and (ii) the hydrophobic reducing agent is an alcohol, carboxylic acid, amine, or a boronalkyl or their combinations.

Other suitable redox systems include (1) organic-inorganic redox pairs, such as oxidation of an alcohol by $Ce^{4+}$, $V^{5+}$, $Cr^{6+}$, $Mn^{3+}$; (2) monomers which can act as a component of the redox pair, such as thiosulfate plus acrylamide, thiosulfate plus methacrylic acid, and N,N-dimethylaniline plus methyl methacrylate, and (5) boronalkyl-oxygen systems.

iv. Exemplary Initiators

Exemplary initiators include, but are not limited to, diacyl peroxides such as benzoyl peroxide, dichlorobenzoyl peroxide, dilauroyl peroxide, didecanoyl peroxide, diacetyl peroxide succinic acid peroxide, disuccinic peroxide and di(3,5,5-trimethylhexanoyl) peroxide. In a preferred embodiment, the diacyl peroxide is an aromatic diacyl peroxide, such as benzoyl peroxide.

Other exemplary initiators include, but are not limited to, peroxydicarbonates such as diethyl peroxydicarbonate, di-n-butyl peroxydicarbonate, diisobutyl peroxydicarbonate, di-4-tert-butylcyclohexyl peroxydicarbonate, di-sec-butyl peroxydicarbonate, di-2-ethylhexyl peroxydicarbonate, di-n-propyl peroxydicarbonate and diisopropyl peroxydicarbonate; peroxyesters, such as t-butyl perneodecanoate, t-butyl and t-amyl peroxy 2-ethyl hexanoate, and t-butyl peroxybenzoate; monoperoxycarbonates based on t-butyl and t-amyl monoperoxy 2-ethylhexyl carbonates; persulfates, such as potassium persulfate, ammonium persulfate, and sodium persulfate; cumene hydroxide, tert-butyl hydroperoxide, di(tert-amyl) peroxide, tert-butyl peroxide, 2,5-Bis(tert-butylperoxy)-2,5-dimethylhexane, 1,1-Bis(tert-butylperoxy)-3,3,5-trimethylcyclohexane; 1,1-Bis(tert-amylperoxy)cyclohexane, 1,1-Bis(tert-butylperoxy)-3,3,5-trimethylcyclohexane, 1,1-Bis(tert-butylperoxy)cyclohexane, 2,2-Bis(tert-butylperoxy)butane, 2,4-Pentanedione peroxide, 2,5-Bis(tert-butylperoxy)-2,5-dimethylhexane, 2,5-Di(tert-butylperoxy)-2,5-dimethyl-3-hexyne, 2-Butanone peroxide, cumene hydroperoxide, di-tert-amyl peroxide, dicumyl peroxide, lauroyl peroxide, tert-butyl peracetate, tert-butyl peroxide, tert-butyl peroxybenzoate, tert-butylperoxy 2-ethylhexyl carbonate, tert-Butylperoxy isopropyl carbonate, 4-nitro-benzenecarboperoxoic acid t-butyl ester, cyclohexanone peroxide, [(methylperoxy)(diphenyl)methyl]benzene, bis(t-butylcyclohexyl)peroxydicarbonate, and 2,4,6-triphenylphenoxyl dimer.

For substrates requiring coating on both internal and external surfaces, additional considerations are required for initiating polymerization. Thermal initiators can be used; however, the elevated temperature typically required can adversely affect the substrate material. UV based approaches must be designed such that they can penetrate through the material or can be applied intralumenally, for instance from a fiber optic source threaded into the lumen. This may be achieved by selecting a photoactive initiator which is labile at a UV wavelength not absorbed by the substrate polymer. Generally, lower wavelength UV irradiation is less absorbed and penetrates more readily than higher wavelength UV.

In contrast, redox chemistries generally do not require a direct line of sight to a light source to initiate polymerization since polymerization is not initiated photolytically and therefore may be advantageous for coating substrates that have one or more surfaces that are difficult to expose to the UV source, such as catheter lumens. Further, redox polymerization typically can be done at low temperatures, for example less than 60° C., less than 55° C., less than 50° C., less than 45° C., less than 40° C., less than 35° C., or less than 30° C.

The graft-from polymerization can propagate through a cationic or anionic reaction, where the substrate surface acts as the cation or anion initiator or a cationic or anionic initiator is immobilized on the substrate and the monomer contains a reactive olefin. Examples of anionic polymerization are anionic ring opening, as in the case of synthesizing polycaprolactone or polycaprolactam, where the polymerization proceeds through a lactone or lactam moiety in a ring structure containing a pendant zwitterion group. Alternatively, an organic ring containing one or more units of unsaturation and a pendant zwitterionic group are polymerized. In one embodiment a pendant olefin is included in the monomer unit and is used for crosslinking, such as in ring opening metathesis polymerization (ROMP).

Methods of Use

The materials described above may be in the form of a medical device or other article to which the non-fouling material is grafted. Suitable devices include, but are not limited to, surgical, medical or dental instruments, ophthalmic devices, wound treatments (bandages, sutures, cell scaffolds, bone cements, particles), appliances, implants, scaffolding, suturing material, valves, pacemaker, stents, catheters, rods, implants, fracture fixation devices, pumps, tubing, wiring, electrodes, contraceptive devices, feminine hygiene products, endoscopes, wound dressings and other devices, which come into contact with tissue, especially human tissue.

In one embodiment, the non-fouling materials are grafted directly from a fibrous material, incorporated into a fibrous material or grafted indirectly from a fibrous material (e.g., coated on a different surface coating). These include wound dressings, bandages, gauze, tape, pads, sponges, including woven and non-woven sponges and those designed specifically for dental or ophthalmic surgeries (See, e.g., U.S. Pat. Nos. 4,098,728; 4,211,227; 4,636,208; 5,180,375; and 6,711,879), paper or polymeric materials used as surgical drapes, disposable diapers, tapes, bandages, feminine products, sutures, and other fibrous materials.

Fibrous materials are also useful in cell culture and tissue engineering devices. Bacterial and fungal contamination is a major problem in eukaryotic cell culture and this provides a safe and effective way to minimize or eliminate contamination of the cultures, The non-fouling agents are also readily bound to particles, including nanoparticles, microparticles, millimeter beads, or formed into micelles, that have uses in a variety of applications including cell culture, as mentioned above, and drug delivery. Non-fouling, biocompatible, polymeric micelles would prevent protein denaturation preventing activation of the immune response allowing for a more stealthy delivery of the desired therapeutic.

The non-fouling material can also be applied directly to, or incorporated in, polymeric, metallic, or ceramic substrates. Suitable devices include, but are not limited to surgical, medical or dental instruments, blood oxygenators, pumps, tubing, wiring, electrodes, contraceptive devices, feminine hygiene products, endoscopes, grafts, stents, pacemakers, implantable cardioverter-defibrillators, cardiac resynchronization therapy devices, ventricular assist devices, heart valves, catheters (including vascular, urinary, neurological, peritoneal, interventional, etc.), shunts, wound drains, dialysis membranes, infusion ports, cochlear implants, endotracheal tubes, guide wires, fluid collection bags, sensors, wound treatments (dressings, bandages, sutures, cell scaffolds, bone cements, particles), ophthalmic devices, orthopedic devices (hip implants, knee implants, spinal implants, screws, plates, rivets, rods, intramedullary nails, bone cements, artificial tendons, and other prosthetics or fracture repair devices), dental implants, breast implants, penile implants, maxillofacial implants, cosmetic implants, valves, appliances, scaffolding, suturing material, needles, hernia repair meshes, tension-free vaginal tape and vaginal slings, tissue regeneration or cell culture devices, or other medical devices used within or in contact with the body or any portion of any of these. Preferably, the non-fouling coating herein does not significantly adversely affect the desired physical properties of the device including, but not limited to, flexibility, durability, kink resistance, abrasion resistance, thermal and electrical conductivity, tensile strength, hardness, and burst pressure.

In one embodiment, the substrate is a vascularly inserted catheter such as a peripherally inserted central catheter (PICC), central venous catheter (CVC) or hemodialysis catheter, venous valves, punctual plugs, and intra-ocular devices and implants.

In another embodiment, the substrate is a vascularly inserted catheter formed from a medical grade polyurthethane or CARBOTHANE® or formed from a material coated with a medical grade polyurethane.

In one specific embodiment, the catheter comprises an elongated catheter body containing multiple lumens. For example, the catheter may be a double-lumen or a triple-lumen catheter. The lumens may be coaxial or side-by-side. In one exemplary embodiment, the catheter body has two side-by-side lumens, each having a "D" shape and the catheter body has a length that is greater than 5 cm; typically the catheter body of such catheters have a length of at least 11 cm. In one particularly preferred embodiment, the catheter body is a medical-grade polycarbonate-based aliphatic and aromatic polyurethane.

The non-fouling materials can also be added to paints and other coatings and filters to prevent mildew, bacterial contamination, and in other applications where it is desirable to prevent fouling, such as marine applications (ship hull coatings), contact lenses, dental implants, coatings for in vivo sensors, devices for separations, such as membranes for microbial suspension, biomolecule separation, protein fractionation, cell separation, waste water treatment, bioreactors, and food processing.

Other applications include the treatment of fibers, particulates and films for applications in textiles, additives, electric/optical appliances, carbon nanotubes, packaging materials and colorants/inks.

Having described the invention in detail, it will be apparent that modifications and variations are possible without departing from the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Radio-Labeling Method for all Examples

The test samples are placed in a suitable sized container, which may be a 96-well manifold, microcentrifuge tube, or other container. The volumes in the following are appropriate for a 96-well plate, but may be scaled to properly cover a device being tested. The samples are sterilized with 70% ethanol solution for thirty minutes and the test groups run with an n per run of 3-4. The sample container is blocked with 20 mg/mL Bovine Serum Albumin in 1×PBS for 1 hour at 4° C., followed by three rinses with 1×PBS before samples are added. The sample is exposed to 300 µL of a 70 µg/mL unlabeled fibrinogen solution containing 1.4 µg/mL I-125 radiolabeled fibrinogen. The samples is incubated for one hour at 37° C. and put on an orbital shaker at 150 RPM. The test solution is then removed and four 1-minute rinses with a 10 mM NaI and one 1-minute rinse with 1×PBS is performed. The samples are be loaded into a gamma counter. The counter measures the radioactivity in I-125 counts per minute for each sample and this data is used to calculate a percent reduction of the non-fouling polymer layer samples versus the reference substrates, that is the same or an otherwise functionally equivalent substrate lacking the non-fouling polymer layer. The percent reduction is equal to: (1−non-fouling sample CPM/Average CPM of the Reference Substrate)*100%.

Example 1—Ti Substrates

Titanium coupons (99.5%, 0.25 mm thick, 1×0.5 cm) were first washed with acetone under sonication for 10 min and dried in the air, then treated with piranha solution for 30 min. After clean and drying, the samples were coated with 1% polyurethane (Tecoflex)/THF solution with 0.1% BP, and air-dried in dark for 30 min. Then coupons were dip-coated for another three times and dried in dark over 3 nights. The solution was flushed with nitrogen for 30 min before the reaction, and reacted under a UV reactor for 14 h. The samples were rinsed with PBS. A determination of fibrinogen adsorption using the radiolabeling method shows fibrinogen adsorption was reduced 75%.

Example 2—Polycarbonate Substrates

Polycarbonate central posts were imbibed with 10 wt. % BP/acetone solution for 6 hours. The sample was kept in dark at RT overnight. The samples were washed with water before reaction. The reaction was performed in a reaction tube and 10 wt. % carboxybetaine acrylamide solution was added into the tube. A 30-min degassing was applied by bubbling with argon before the reaction. The reaction was exposed to UV light for 6 hours (peak wavelength of 365 nm, generated by a 100 W UV lamp). After washing with PBS, the samples exhibited a fibrinogen deduction of 92.7% by ELISA.

In the ELISA assay, the samples were incubated for 90 minutes at 37° C. in 10% (v/v) fetal bovine serum to block the areas unoccupied by fibrinogen. The samples were rinsed, transferred to clean wells, and incubated for 1 hour with 5.5 µg/mL horseradish peroxidase conjugated anti-fibrinogen in 10% (v/v) fetal bovine serum. Again the samples were rinsed and transferred to clean wells with 0.1M phosphate-citrate buffer containing 1 mg/mL chromogen of o-phenylenediamine and 0.02% (v/v) hydrogen peroxide. Incubating at 37° C. for 20 minutes produces an enzyme-induced color reaction, which is terminated by the addition of 2.0N sulfuric acid. The absorbance of light intensity was then be measured using a microplate reader to determine the protein adsorption relative to controls (i.e., reference substrates). For mixed protein solutions, such as whole plasma, surface plasmon resonance (SPR) or optical waveguide lightmode spectroscopy (OWLS) can be utilized to measure surface protein adsorption without necessitating the use of individual antigens for each protein present in solution.

Example 3—Polypropylene Substrates

Polypropylene coupons (0.4" thick, 1×0.5 cm) were imbibed with 5% BPO/toluene solution for 2 hours, and then reacted with 20 wt % SBMA solution and 5 mM Fe(II) gluconate in a 20 mL vial, at 40° C. for 5 hours. A determination of fibrinogen adsorption using the radiolabeling method shows fibrinogen adsorption was reduced by 94±1% after grafting. Absolute adsorption of fibrinogen was 14 ng/cm$^2$ in a fibrinogen adsorption assay in which samples are incubated for 60 minutes at 37° C. in 70 µg/mL fibrinogen derived from human plasma.

Example 4—Silicone Substrates

Silicone tubes were imbibed with 5% dicumyl peroxide (DCP)/heptanes solution for 2 hours and dried overnight. Then the tubes were reacted with 20 wt % SBMA solution and 5 mM Fe(II) gluconate at 37° C. shaking at 100 rpm for 24 hours. A determination of fibrinogen adsorption using the radiolabeling method shows fibrinogen adsorption was reduced by 73±4% after grafting.

Example 5—MPC Monomer

Polyurethane (Carbothane®) rods were imbibed with 1 wt. % TBEC/acetone solution for 3 hours. Redox reaction was performed in 10% methacryloyloxyethyl phosphorylcholine (MPC) solution with 5 mM ferrous gluconate in a 20-mL vial. The reaction was kept at 60° C. under shaking at 150 rpm overnight. Then the samples were washed with 20 mL PBS three times with shaking at 150 rpm overnight. With adjustment made for non-modified ends of the sample, the absolute adsorption of fibrinogen was 33 ng/cm$^2$ on modified samples and the reduction from control was 96% using a fibrinogen adsorption assay in which samples are incubated for 60 minutes at 37° C. in 70 µg/mL fibrinogen derived from human plasma.

Example 6—Polyampholyte/Mixed Charge

Polyurethane (Carbothane®) rods (3 cm) were imbibed with 1 wt. % benzoyl peroxide (BPO)/acetone solution for 3 hours. Redox reaction was performed in 10% mixed monomers (sulfopropyl methacrylate potassium salt ("SMP") and [2-(Methacryloyloxy)ethyl] trimethylammonium chloride methacrylate ("META")) with 5 mM ferrous gluconate in a 250 mL round bottom flask. The reaction was kept at 60° C. under stirring for 5 hours. Then the samples were washed with PBS three times. Fibrinogen reduction on the surfaces was measured by the radiolabeling method and is reported in the following table. With adjustment made for non-modified ends of the sample, absolute adsorption of fibrinogen and reductions from control are shown in the table below using a fibrinogen adsorption assay in which samples are incubated for 60 minutes at 37° C. in 70 µg/mL fibrinogen derived from human plasma.

| Sample description | Fibrinogen Adsorption (ng/cm$^2$) | Fibrinogen Reduction |
|---|---|---|
| Carbo-Ba/1% BPO/10%/SMP:META = 40:60 | 91 | 89 ± 5% |
| Carbo-Ba/1% BPO/10%/SMP:META = 45:55 | 92 | 88 ± 3% |
| Carbo-Ba/1% BPO/10%/SMP:META = 50:50 | 85 | 89 ± 2% |
| Carbo-Ba/1% BPO/10%/SMP:META = 55:45 | 81 | 90 ± 3% |
| Carbo-Ba/1% BPO/10%/SMP:META = 60:40 | 59 | 93 ± 6% |

Example 7—Surface Contact Angle Measurement

Flat silicone samples (Sylgard 184, Dow Corning, Mich.) and silicone tubes (TYGON 3350, Cole-Parmer Instrument Company, IL) were modified with SBMA as described in example 4. Additionally, flat polyurethane films (Tecoflex, SG93A, Lubrizol) were modified with SBMA as described in example 4. The samples were first soaked with pure ethanol for 5 minutes and washed with PBS for three times. The samples were then soaked within PBS (150 mM, pH 7.4) for 24 hours and washed three times with purified water. Then the samples were dried under a flow of air for 5 min before testing. The contact angle was measured using a video contact angle system (VCA 2000, AST Inc.). A drop of purified water (1 µL) was deposited on the test surface. Then the shape of the droplet was taken by a microscope with a CCD camera, and the contact angle was determined using VCA Optima XE. Following are the resulting contact angle measurements.

| Description | Contact Angle (degree) |
|---|---|
| SBMA modified flat silicone | 10.5 |
| Unmodified flat silicone | 117.9 |
| SBMA modified silicone tube | 23.4 |
| Unmodified silicone tube | 95.7 |
| SBMA modified Tecoflex film | 5.3 |
| Unmodified Tecoflex film | 73.3 |

Example 8—Coating Dryand Humidified Thickness Measurement

Polyurethane (Carbothane®) with barium sulfate DD tube samples (25 cm) for swelling analysis were taken from dry storage (rinsed in 1×PBS post reaction then air dried overnight and stored in sterilization bag) and put directly into 4% aqueous osmium tetroxide. All modified samples were cut from a large 25 cm treated tube. Two modified samples were stained with osmium tetroxide while a third repetition was left unstained. Samples were left in osmium tetroxide overnight and then rinsed thoroughly with distilled water. Any wet stained samples were ethanol dehydrated (submerged for two minutes each in solutions of 50, 60, 70, 80, 90 & 95% ethanol) and then let air dry.

All of the samples were freeze fractured for imaging by being submerged in liquid nitrogen then cracked with an ultra microtome blade (Leica Ultracut UCT Ultramicrotome). One half of the freeze fractured samples were put in distilled water while the other half were prepared for dry imaging under high vacuum. The dry samples were sputter coated in gold for 90 seconds using a sputter coater (Cressington 208HR) and then imaged under high vacuum at 5 kV using an SE2 detector under a Scanning Electron Microscope (SEM) (Supra55VP FESEM, Zeiss). The thickness of dried coating was measured along the interfaces (Ldry).

The wet samples were first imaged after soaking in water for approximately 4 hours. They were submerged wet into liquid nitrogen and then fixed to a cold stage set to −8° C. The samples were then imaged using a VPSE detector at the highest resolvable humidity (approximately 26% or 81 Pa) under a Scanning Electron Microscope (SEM) (Supra55VP FESEM, Zeiss) with an Environmental Scanning Electron Microscope (E-SEM) (Zeiss EVO 55). When the samples were warmed and removed from the cold stage it was ensured that they were still wet. The final measurements were taken after the samples were soaking in 1×PBS for at least 1 hr (before going into 1×PBS they were soaking in distilled water overnight). Immediately before imaging, the samples were rinsed quickly with water to remove any surface salts and then submerged in liquid nitrogen and fixed to the cold stage. The thickness of hydrated samples was measured along the interfaces (Lhyd).

The linear swellability of the coating was calculated by, $$LSW=(L_{hyd}-L_{dry})/L_{dry}\times100\%$$

The results of the thickness and the linear swellability are listed in the following table.

| | Thickness ± SD (nm) | LSW |
|---|---|---|
| $L_{dry}$ (n = 7) | 668 ± 170 | — |
| $L_{hyd}$ (H$_2$O) (n = 7) | 801 ± 287 | 20% |
| $L_{hyd}$ (PBS) (n = 12) | 905 ± 262 | 36% |

Example 9—Initiator Penetrating Measurement

Polyurethane rod (10 French Carbothane® rods with 20% BaSO$_4$) imbibed with different initiators (10% dicumyl peroxide and 1% benzoyl peroxide) after reaction were cross-sectioned with a razor blade. The cross-sectional surface was analyzed under a Nicolet iN-10 IR microscope (Thermo Scientific) FTIR. The IR spectrum from an attenuated total reflection (ATR) tip was used to detect the penetrating depth of imbibed initiator from the edge of the samples. The ATR-FTIR spectra on the center of the polyurethane rod imbibed with 10% dicumyl peroxide ("DCP") showed a strong peak at ca. 700 cm-1 (characteristic peak of DCP) and the ATR-FTIR spectra on the center of the polyurethane rod imbibed with 1% benzoyl peroxide ("BPO") showed a strong peak at ca. 700 cm$^{-1}$ (characteristic peak of BPO)

Example 10—Comparative Performance SBMA and OEGMA

Polyurethane (Carbothane®) rods (3 cm) were imbibed with either 10 wt. % dicumyl peroxide (DCP)/acetone, or 1 wt % O,O-t-Butyl-O-(2-ethylhexyl) mono-peroxycarbonate ("TBEC")/acetone solution for 2 h. Modification was performed on the imbibed samples using 10% SBMA or 1% OEGMA with 5 mM ferrous gluconate. The reaction was kept at 60° C. under stirring for 5 hours. Then the samples were washed with PBS three times.

The results depict a difference between the Standard Redox 10% SBMA and the 1% OEGMA monomer. The 1% OEGMA exhibited inferior performance (log reduction=0.86) when tested in the mCDC *E. coli* as compared to the Standard Redox 10% SBMA (log reduction=2.24).

Example 11—Protein Resistance—Catheter Walls

Catheters (613.7±1.8 mm body length) were imbibed with O,O-t-Butyl-O-(2-ethylhexyl) mono-peroxycarbonate ("TBEC") and modified with SBMA monomer and Fe(II) reaction solution. The modified samples (Lots "A" and "B") were washed and dried.

Protein resistance of the outside portion of the shaft of the samples was determined using the radiolabeling method and the results appear in the following table.

| Lot | Estimated Modification Thickness by IR | % Reduction | Std Dev | Fg (ng/cm2) |
|---|---|---|---|---|
| A | 1654 ± 299 (n = 6) | 87% | 2% (n = 4) | 47 |
| B | 1630 ± 201 (n = 5) | 90% | 2% (n = 4) | 37 |

Example 12—Contact Angle

Polyurethane (Tecothane®)-30% BaSO$_4$-5FR DD lumen catheters (562.2±0.9 mm body length) were imbibed with O,O-t-Butyl-O-(2-ethylhexyl) mono-peroxycarbonate ("TBEC") and modified with SBMA monomer and Fe(II) reaction solution. Contact angle of the outside portion of the shaft of these devices and for unmodified controls are shown below.

| Sample | Estimated Modification Thickness by IR | Contact Angle (degrees) | St Dev |
|---|---|---|---|
| Unmodified catheter | Not applicable | 79.7 | 2.4 |
| Modified catheter | 3589 (n = 1) | 20.9 | 1.5 |

Example 13—Surface Roughness

5FR double D lumen tubing samples (3 cm in length) of polyurethane (Tecothane®)-30% BaSO$_4$ were imbibed with a solution of TBEC, washed, and dried. The imbibed samples were then modified with an aqueous solution of SBMA and iron(II) gluconate for 2 hours for some samples and for 3 hours for others, and washed with PBS. The estimated thickness by IR analysis, and the roughness as determined from LEXT confocal microscopy were determined and is shown in the table below. Roughness ($R_{rms}$) was 0.259 μm for the unmodified, 0.162 μm for the sample modified for 2 hours, and 0.107 μm for the sample modified for at 3 hours. Modification thickness was 677 nm for the sample modified for 2 hours and 1218 nm for the sample modified for 3 hours.

| Reaction Time | Modification thicness (nm) | Roughness (Rq) (um) |
|---|---|---|
| Control (not modified) | Not modified | 0.259 |
| 2 h | 677 ± 157 | 0.162 |
| 3 h | 1218 ± 237 | 0.107 |

Example 14—Residual Initiator Visualization

In the presence of an oxidant such as peroxide, iodide is converted to iodine. The relative amount of peroxide can be qualitatively determined by treating a test article with an iodide salt solution and comparing the presence and/or intensity of the resulting orange-brown iodine stain. Iodide solutions were prepared by adding 3-6 g NaI salt to 10 mL EtOH (reagent alcohol, 95%), vortexing the mixture for 10 seconds, allowing the vortexed mixture to rest for 10 minutes to dissolve the salt, and then filtering the mixture through a PTFE filter (0.45 μm) to remove any undissolved particles. Each test article (e.g., 1.5 cm in length) was soaked with, for example, 1 mL of the ethanolic NaI solution prepared above in a test tube for one minute. Then, the test article was taken out and dried by a flow of air for one minute to remove solvent. The test article was then put in an 8 mL scintillation vial with cap tightened, and placed in a 60° C. oven for 45 min to develop the color on the surface. The presence of stain was then recorded and could be compared with a yellow tone chart (ranging from 0 to 10) to get a darkness number.

Four sets of test articles were immersed in a solution of sodium iodide, rinsed, and heated in a 60° C. oven as described. The first set was untreated polyurethane (Tecothane® 97A)-30% BaSO$_4$ 5FR double D lumen tubing. The second set was polyurethane (Tecothane®) 97A-30% BaSO$_4$ 5FR double D lumen tubing, imbibed with TBEC, but no surface modification was grown. The third and fourth sets were polyurethane (Tecothane 97A®)-30% BaSO$_4$ 5FR double D lumen tubing, imbibed with TBEC and surface modified with SBMA. Iodine staining was not observed for the first set, but was for the other three sets.

Example 15—Residual Initiator Determination by Extraction

Test articles (polyurethane (Tecothane®) 97A-30% BaSO$_4$ 5FR double D lumen tubing) were imbibed with TBEC and surface modified with SBMA. The extraction conditions are summarized in the following table and the results demonstrate that the initiator was extracted with 95% ethanol.

| Extraction condition | Iodine stain observed (yes/no) |
|---|---|
| 95% Ethanol 37° C. for 2 h | no |
| 70% Ethanol 37° C. for 2 h | yes |
| 10% tween 37° C. for 2 h | yes |
| PBS 37° C. for 2 h | yes |

Example 16—Residual Initiator Determination by IR

IR analysis of a 25 cm polyurethane (Carbothane®)-BaSO$_4$ 14FR double lumen tube that was imbibed with dicumyl peroxide and surface modified with SBMA in the presence of iron(II) gluconate, washed and dried, showed a peak at 699 cm$^{-1}$ indicating the presence of the cumyl group.

Example 17—Residual Initiator Quantitation by GCMS

Polyurethane (Tecothane®)-30% BaSO$_4$-5FR DD lumen catheters were imbibed with O,O-t-Butyl-O-(2-ethylhexyl) mono-peroxycarbonate ("TBEC") and some of the imbibed samples were surface modified with SBMA monomer and Fe(II) reaction solution. The imbibed only and surface modified samples were washed and dried. Some of the modified samples were washed with isopropanol prior to washing and drying.

Quantification of peroxides and their decomposition products: Quantification of TBEC (OO-tert-butyl O-(2-ethylhexyl)monoperoxycarbonate), using GCMS. The quantity of TBEC was determined based on GCMS analysis of methanolic sample extracts. The samples were cryogenically ground to a fine powder before extraction. A 5 ml aliquot of methanol was added to approximately 370 mg of each sample. The extraction was allowed to continue with gentle agitation. The samples were filtered through a 0.2 μm PTFE syringe filter prior to analysis by GCMS. Because the compound of interest is prone to degradation, resulting in a series of decomposition products as observed by GCMS, quantitation was based on ethyl hexanol, the major degradation product observed in analysis of TBEC standards (assuming there are no other sources of ethyl hexanol in the samples). A series of dilutions was prepared of a TBEC standard in methanol and a calibration curve was prepared based on the ethyl hexanol peak. Concentration of TBEC was calculated based on the calibration prepared and the percent composition in each sample was calculated using the following equation: % TBEC Composition=concentration (mg/mL)×5 mL mass sample extracted (mg)×100%. A summary of the average percent TBEC composition values calculated for the sample extracts is provided in the table below.

| Sample | % TBEC Composition | St. Dev. |
|---|---|---|
| Surface modified samples* | 0.208 | 0.020 |
| Imbibed only samples* | 0.304 | 0.007 |
| Surface modified samples, with additional isopropanol wash** | 0.00524 | 0.00106 |

*This data represents the average of three replicate sample injections.
**This data represents the average of four replicates of thee samples.

Example 18—Surface Modification Thickness Variation

Thrombogenicity of modified polyurethane (Tecothane® 97A)-30% BaSO$_4$ 5FR double D lumen tubing with different SBMA modification thicknesses.

(a) Tecothane-BaSO4 5FR, DD lumen tubing, was imbibed with TBEC and modified with SBMA from an iron(II) gluconate aqueous solution. Modifications of different grafted SBMA thickness on the outside of the tubing as estimated by IR analysis, were obtained by adjusting the grafting time. These are summarized in the table below.

(b) The in-vitro evaluation of catheters using the flow model described herein, with the following distinctions: the ends of the catheter tubing were sealed with 5 minute epoxy, and 20 cm of catheter tubing body was inserted into the loop. The flow rate was 200 mL/min for 60-90 minutes. The catheter tubing test articles were then rinsed with saline, photographed, and sectioned (1 cm at distal (tip), 2 cm at insertion), and the adhered radio labeled platelets were counted using a gamma counter. The results are summarized in the table below.

| Thickness Estimation of SBMA modification from IR analysis | Average Radiolabeled Platelet adherence (% Control) |
|---|---|
| 0 | 100 |
| 91 ± 74 | 6.5 |
| 620 ± 231 | 2 |
| 3353 ± 726 | 1 |

Example 19—Surface Roughness Evaluation

Polyurethane (Tecothane®)-30% BaSO$_4$-5FR DD lumen catheters (562.2±0.9 mm body length) were imbibed with O,O-t-Butyl-O-(2-ethylhexyl) mono-peroxycarbonate ("TBEC") and modified with SBMA monomer and Fe(II) reaction solution. The modified samples were washed and dried. The surface roughness of the modified samples was compared to unmodified samples by LEXT Confocal Microscope Imaging and Roughness Analysis. Samples were mounted on a glass slide by double-sided tape. Digital 3-D images were taken with the Olympus LEXT OLS4000 laser confocal microscope ("LEXT") under an Olympus MPLAPON 50× objective lens. The digital images taken in this way have a 256×256 μm field area. The Z-direction repeatability for this LEXT machine has been certified by Olympus to be less than 0.012 μm. To measure the roughness, at least three images were taken from each sample and the Rrms roughness calculated using a 9 μm cut-off length. As measured, the un-modified substrate had an $R_{rms}$ of 0.321 μm, whereas the modified substrate had an $R_{rms}$ of 0.199 μm.

What is claimed is:

1. A process for grafting a polymer from an article comprising a substrate having a surface, a bulk beneath the surface, and a near-surface zone lying between the surface and the bulk, the process comprising incorporating a polymerization initiator into the near-surface zone and graft polymerizing a polymer from the substrate surface to form a grafted polymer layer comprising the grafted polymer, the grafted polymer layer having a global average dry thickness that is at least equal to the global average $R_{rms}$ surface roughness of the substrate surface and at least about 50 nanometers.

2. The process of claim 1 wherein the grafted polymer is a zwitterionic polymer.

3. The process of claim 1 wherein the grafted polymer is a chain growth addition polymer.

4. The process of claim 1 wherein the grafted polymer comprises repeat units corresponding to Formula 1

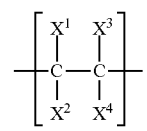

Formula 1 wherein
$X^1$ and $X^2$ are independently hydrogen, hydrocarbyl, substituted hydrocarbyl, heterocyclo, or substituted carbonyl, provided, however, $X^1$ and $X^2$ are not each selected from the group consisting of aryl, heteroaryl, and heterosubstituted carbonyl,
$X^3$ is hydrogen, alkyl or substituted alkyl,
$X^4$ is —O$X^{40}$, —N$X^{41}X^{42}$, —N+$X^{41}$ $X^{42}X^{43}$, —S$X^{40}$, aryl, heteroaryl or acyl,
$X^{40}$ is hydrogen, hydrocarbyl, substituted hydrocarbyl, heterocyclo or acyl,
and
$X^{41}$, $X^{42}$ and $X^{43}$ are independently hydrogen, hydrocaryl, substituted hydrocarbyl or heterocyclo.

5. The process of claim 1 wherein the grafted polymer comprises at least one repeat unit corresponding to Formula 2:

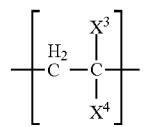

Formula 2 wherein
$X^3$ is hydrogen, alkyl or substituted alkyl, and
$X^4$ is a pendant group comprising an oxylated alkylene moiety, a zwitterionic moiety, an anionic moiety, or a cationic moiety.

6. The process of claim 1 wherein the polymer comprises repeat units corresponding to Formula 4:

Formula 4

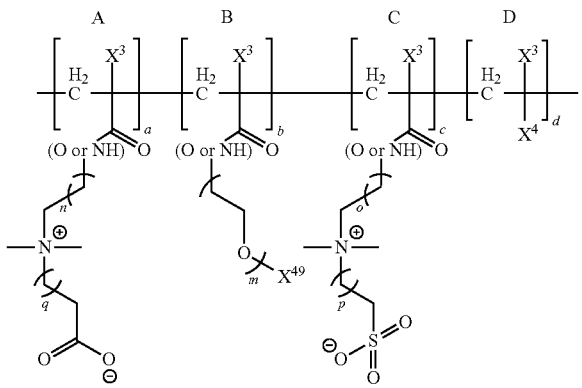

wherein
a is 0-1;
b is 0-1;
c is 0-1;
d is 0-1;
m is 1-20
n and o are independently 0-11;
p and q are independently 0-11;
$X^3$ is hydrogen, alkyl or substituted alkyl;
$X^4$ is —$OX^{40}$, —$NX^{41}X^{42}$, —$SX^{40}$ aryl, heteroaryl or acyl;
$X^{40}$ is hydrogen, hydrocarbyl, substituted hydrocarbyl, heterocyclo or acyl;
$X^{41}$ and $X^{42}$ are independently hydrogen, hydrocarbyl, substituted hydrocarbyl or heterocyclo; and
$X^{49}$ is hydrogen, hydrocarbyl or substituted hydrocarbyl, provided the sum of a, b, c and d is greater than 0 and $X^4$ of repeat unit D differs from the corresponding pendant group of repeat units A, B and C.

7. The process of claim 1 wherein the grafted polymer comprises repeat units corresponding to Formula 5, Formula 6, Formula 7, Formula 8, or Formula 9:

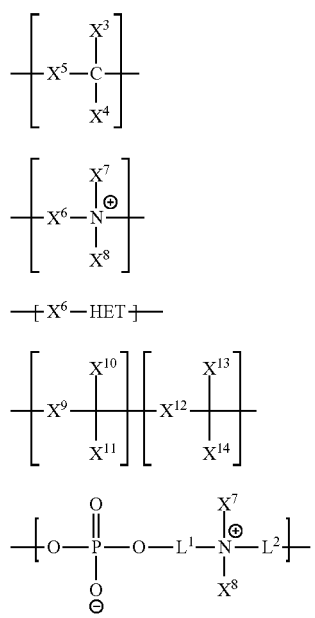

Formula 5

Formula 6

Formula 7

Formula 8

Formula 9 wherein
HET is part of a heterocyclic structure,
$X^3$ is hydrogen, alkyl or substituted alkyl,
$X^4$ is —$OX^{40}$, —$NX^{41}X^{42}$, —$SX^{40}$, aryl, heteroaryl or acyl,
$X^5$ is ester, anhydride, imide, amide, ether, thioether, thioester, hydrocarbylene, substituted hydrocarbylene, heterocyclo, urethane, or urea;
$X^6$ is hydrocarbylene, substituted hydrocarbylene, heterocyclo, amide, anhydride, ester, imide, thioester, thioether, urethane, or urea;
$X^7$ is hydrogen, alkyl or substituted alkyl;
$X^8$ is an anionic moiety;
$X^9$ is hydrocarbylene, substituted hydrocarbylene, heterocyclo, amide, anhydride, ester, imide, thioester, thioether, urethane, or urea;
$X^{10}$ is hydrogen, alkyl or substituted alkyl;
$X^{11}$ is a cationic moiety;
$X^{12}$ is hydrocarbylene, substituted hydrocarbylene, heterocyclo, amide, anhydride, ester, imide, thioester, thioether, urethane, or urea;
$X^{13}$ is hydrogen, alkyl or substituted alkyl;
$X^{14}$ is an anionic moiety;
$L^1$ and $L^2$ are independently hydrocarbylene, substituted hydrocarbylene, heterocyclo, amide, anhydride, ester, imide, thioester, thioether, urethane, or urea; and
$X^{40}$ is hydrogen, hydrocarbyl, substituted hydrocarbyl, heterocyclo or acyl,
and
$X^{41}$ and $X^{42}$ are independently hydrogen, hydrocarbyl, substituted hydrocarbyl or heterocyclo.

8. The process of claim 1, wherein the graft polymerizing includes graft polymerizing the grafted polymer in a polymerization mixture comprising polymerization monomers and a solvent system.

9. The process of claim 8 wherein at least the portion of the substrate into which the polymerization initiator is incorporated is not significantly swelled by the polymerization mixture.

10. The process of claim 8 wherein the polymerization monomers and the initiator(s) incorporated into the substrate has/have limited solubility in the solvent system.

11. The process of claim 8 wherein the substrate is a composite of materials, the substrate comprises a coating of a precoat material overlying a metal, ceramic, glass or semi-metallic material, and the coating of the precoat material does not swell more than 30% by volume at 25° C. under equilibrium conditions in the polymerization mixture solvent system.

12. The process of claim 8 wherein the initiator comprises a redox pair.

13. The process of claim 12 wherein one member of the pair is soluble in the polymerization mixture solvent system but the other has limited solubility in the polymerization mixture solvent system.

14. The process of claim 12 wherein the redox pair comprises a peroxide and a reducing agent wherein the peroxide has limited solubility in the polymerization solvent system and the reducing agent has high solubility in the polymerization solvent system.

* * * * *